(12) United States Patent
Amano et al.

(10) Patent No.: US 12,183,442 B2
(45) Date of Patent: Dec. 31, 2024

(54) MEDICINE SORTING DEVICE

(71) Applicant: YUYAMA MFG. CO., LTD., Osaka (JP)

(72) Inventors: Hirokazu Amano, Osaka (JP); Tomohiro Sugimoto, Osaka (JP); Tasuku Kono, Osaka (JP); Shinki Kojima, Osaka (JP); Hiromichi Tsuda, Osaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 784 days.

(21) Appl. No.: 17/059,250

(22) PCT Filed: Jun. 12, 2019

(86) PCT No.: PCT/JP2019/023215
§ 371 (c)(1),
(2) Date: Nov. 26, 2020

(87) PCT Pub. No.: WO2019/244729
PCT Pub. Date: Dec. 26, 2019

(65) Prior Publication Data
US 2021/0205179 A1    Jul. 8, 2021

(30) Foreign Application Priority Data

Jun. 19, 2018  (JP) .................................. 2018-116206
Aug. 24, 2018  (JP) .................................. 2018-157492
Dec. 14, 2018  (JP) .................................. 2018-234914

(51) Int. Cl.
*G16H 20/10*    (2018.01)
*A61J 7/00*    (2006.01)
(Continued)

(52) U.S. Cl.
CPC ............ *G16H 20/10* (2018.01); *A61J 7/0084* (2013.01); *B07C 5/3425* (2013.01); *B65B 3/003* (2013.01);
(Continued)

(58) Field of Classification Search
CPC ........ A61J 3/00; A61J 1/03; A61J 3/06; A61J 3/07; A61J 3/10; A61J 7/0084;
(Continued)

(56) References Cited

U.S. PATENT DOCUMENTS 7,044,306 B2 *  5/2006  Deppermann ........... A01C 1/04
                                                    221/254
9,846,077 B2 * 12/2017  Hofmeister ........... G01J 3/0237
(Continued)

FOREIGN PATENT DOCUMENTS

CN    105188637 A   12/2015
CN    107072881 A    8/2017
(Continued)

OTHER PUBLICATIONS

Office Action in JP Application No. 2021-069967, mailed Mar. 7, 2023, 10 pp.
(Continued)

*Primary Examiner* — Patrick H MacKey
(74) *Attorney, Agent, or Firm* — HAUPTMAN HAM, LLP

(57) ABSTRACT

Drugs can be sorted irrespective of whether or not drug data is registered. A drug sorting device includes a conveying/sorting unit configured to: accommodate drugs determined to have drug data corresponding to image data into a confirmed area of a second accommodating portion for each type; and accommodate drugs determined to have no drug data corresponding to the image data into a temporarily determined area.

4 Claims, 40 Drawing Sheets

(51) Int. Cl.
*B07C 5/342* (2006.01)
*B65B 3/00* (2006.01)
*B65B 57/14* (2006.01)
*B65G 1/137* (2006.01)
*G06F 18/2431* (2023.01)
*G06V 20/52* (2022.01)
*G16H 20/13* (2018.01)
*G16H 70/40* (2018.01)

(52) U.S. Cl.
CPC ............ *B65B 57/14* (2013.01); *B65G 1/1371* (2013.01); *G06F 18/2431* (2023.01); *G06V 20/52* (2022.01); *G16H 20/13* (2018.01); *G16H 70/40* (2018.01); *B65G 2203/0208* (2013.01); *B65G 2203/041* (2013.01); *G06V 2201/03* (2022.01)

(58) Field of Classification Search
CPC ......... B07C 5/02; B07C 5/3425; B07C 5/342; B07C 5/36; B65G 1/137; B65G 1/1371; B65G 2203/0208; B65G 2203/041; G06T 1/0007; G06T 7/00; H04N 7/18; G16H 20/10; G16H 20/13; G16H 70/40; B65B 3/003; B65B 57/14; G06F 18/2431; G06V 20/52

See application file for complete search history.

(56) References Cited

U.S. PATENT DOCUMENTS

| | | | |
|---|---|---|---|
| 9,940,439 B2* | 4/2018 | Royaee | G16Z 99/00 |
| 10,565,545 B2* | 2/2020 | Yonaha | G06Q 10/087 |
| 10,872,688 B2* | 12/2020 | Swarvar | G16H 20/13 |
| 2006/0058726 A1 | 3/2006 | Handfield et al. | |
| 2011/0060448 A1 | 3/2011 | Gotou et al. | |
| 2015/0178674 A1 | 6/2015 | Yonaha et al. | |
| 2015/0266604 A1 | 9/2015 | Amano et al. | |
| 2015/0302255 A1* | 10/2015 | Gershtein | G06T 3/60 |
| | | | 382/128 |
| 2017/0140601 A1 | 5/2017 | Kohama et al. | |
| 2017/0246083 A1 | 8/2017 | Amano et al. | |
| 2017/0301087 A1 | 10/2017 | Yuyama et al. | |
| 2017/0305589 A1* | 10/2017 | Yuyama | G06Q 20/4014 |
| 2020/0010224 A1 | 1/2020 | Koike et al. | |
| 2020/0156120 A1 | 5/2020 | Amano et al. | |

FOREIGN PATENT DOCUMENTS

| | | |
|---|---|---|
| EP | 3141237 A1 | 3/2017 |
| JP | 201355970 A | 3/2013 |
| JP | 2013215343 A | 10/2013 |
| JP | 201467342 A | 4/2014 |
| JP | 201554115 A | 3/2015 |
| JP | 201842820 A | 3/2018 |
| JP | 2021-28033 A | 2/2021 |
| KR | 1020170007247 A | 1/2017 |
| WO | 2005065627 A1 | 7/2005 |
| WO | 2010113436 A1 | 10/2010 |
| WO | 2014054447 A1 | 4/2014 |
| WO | 2015170761 A1 | 11/2015 |
| WO | 2015170762 A1 | 11/2015 |
| WO | 2016047295 A1 | 3/2016 |
| WO | 2016047569 A1 | 3/2016 |
| WO | 2017159819 A1 | 9/2017 |
| WO | 2017183533 A1 | 10/2017 |
| WO | 2017217366 A1 | 12/2017 |
| WO | 2018190394 A1 | 10/2018 |

OTHER PUBLICATIONS

International Search Report in PCT/JP2019/023215, mailed Sep. 17, 2019. 10pp.
Office Action in JP Application No. 2019-556717, mailed Jul. 7, 2020. 9pp.
Partial Supplementary European Search Report in EP Application No. 19822845.4, dated Feb. 10, 2022. 24pp.
Office Action in JP Application No. 2020-196343, mailed Feb. 2, 2021. 6pp.
Office Action in JP Application No. 2020-196343, mailed Dec. 15, 2020. 8pp.
Office Action in TW Application No. 108114243, dated Jan. 5, 2023, 15pp.
Office Action in KR Application No. 10-2020-7032495, mailed Dec. 6, 2023, 8pp.

* cited by examiner

FIG. 19

SORTING CONDITION (LAST PACKAGING DATE) — Ar81
SETTING [USE]  DO NOT SORT DRUG HAVING LAST PACKAGING DATE BEING [30] DAYS AGO OR EARLIER.

SORTING CONDITION (DRUG PRICE) — Ar82
SETTING [USE]  DO NOT SORT DRUG HAVING PRICE EQUAL TO OR LESS THAN [300] YEN.

SORTING CONDITION (DRUG NAME) — Ar83
SETTING [USE]  DO NOT SORT DRUG HAVING DRUG NAME CONTAINING ANY ONE OF

SORTING CONDITION (METHOD)
- SORTING OF DRUG HAVING NO INSCRIPTION [SORT]
- SORTING OF SEMI-TABLET DRUG [SORT]
- MASTER-LESS SORTING [SORT]  NUMBER OF CONTAINERS FOR MASTER-LESS SORTING (1-30) [30]

SORTING CONDITION (DRUG FLAG)
SETTING [USE]

| | | |
|---|---|---|
| POISON [COLLECT] | PSYCHOTROPIC DRUG [COLLECT] | BLOOD PRODUCT [COLLECT] | INVESTIGATIONAL DRUG [COLLECT] |
| NARCOTICS [COLLECT] | THYROID DRUG [COLLECT] | DIABETES DRUG [TO BE SORTED] | STUDY DRUG [COLLECT] |
| POWERFUL DRUG [COLLECT] | ANTIBIOTICS [TO BE SORTED] | ANTICANCER DRUG [COLLECT] | CHINESE HERBAL DRUG [TO BE SORTED] |
| MANAGEMENT UNDER COLD PLACE [TO BE SORTED] | LIGHT-PROOF MANAGEMENT [TO BE SORTED] | | |

[CONFIRM]   ← 2/2 →   [CLOSE]

Im8

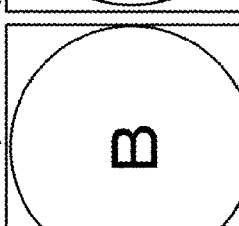

Co1  Co2

Co2  Co1

MEDICINE SORTING DEVICE

RELATED APPLICATIONS

The present application is National Phase of International Application Number PCT/JP2019/023215 filed Jun. 12, 2019, which claims priority of Japanese Application Nos. 2018-116206, filed Jun. 19, 2018, 2018-157492, filed Aug. 24, 2018 and 2018-234914, filed Dec. 14, 2018.

TECHNICAL FIELD

This disclosure relates to a drug sorting device configured to sort drugs and the like.

BACKGROUND ART

Hitherto, a plurality of types of returned drugs have been sorted by type manually by a pharmacist or a doctor. The returned drugs are dispensed drugs that are to be prescribed or have been prescribed to various patients. Therefore, there are an extremely larger number of types of drugs that have been prescribed to a plurality of patients and are then returned together than types of drugs used in drug dispensing work of organizing (packaging) drugs (tablets) (of one or a plurality of types) in units of timings of administration based on prescription information per patient from a drug type group (drug cassettes) organized in advance in, for example, a drug dispensing device in units of drug types. Therefore, it is highly useful to automatically sort the returned drugs for reuse thereof. The drugs to be dispensed for one timing of administration generally have about 2 or 3 types, and at most about 10 types.

In some pharmacies or hospitals (to be exact, in-hospital pharmaceutical departments), the returned drugs are discarded as they are in order to avoid time and labor required for sorting work or a risk of misadministration due to erroneous sorting (erroneous returning to the drug cassette).

In Patent Literature 1, there is disclosed a drug sorting device configured to automatically recognize and store a returned ampoule or vial. This drug sorting device recognizes an orientation and a posture of an ampoule or vial and properties (for example, shape, size, type, and expiration date) of the ampoule or vial. Then, the drug sorting device individually arranges ampoules or vials based on the recognized sizes of the ampoules or vials by associating a storage area set for each ampoule or vial at a time of storage with identification information on each ampoule or vial, to thereby store the individual ampoules or vials in a removable manner.

CITATION LIST

Patent Literature

[PTL 1] WO 2015/170761 A1 (laid opened on Nov. 12, 2015)

SUMMARY OF INVENTION

Technical Problem

However, an object to be returned in Patent Literature 1 is an ampoule or vial, but is not per se a tablet, a capsule, or another such drug that is not accommodated in a container or the like or a drug that is not subjected to packaging or the like. Therefore, in Patent Literature 1, even such drugs (for example, tablets or capsules) themselves are not assumed to be identified and automatically sorted.

In addition, in Patent Literature 1, there are not disclosed details of processing relating to data registration in a drug database (drug master) for managing drug data relating to a plurality of types of drugs.

One aspect of this disclosure has an object to achieve a drug sorting device capable of recognizing a drug itself and automatically sorting the drug. One aspect of this disclosure has another object to achieve a drug sorting device capable of sorting a drug irrespective of whether or not its drug data has been registered.

Solution to Problem

According to one aspect of this disclosure, there is provided a drug sorting device including: a first accommodating portion configured to accommodate a plurality of types of drugs; a second accommodating portion configured to accommodate at least a part of the drugs in a state of being sorted by type; an image pick-up unit configured to pick up an image of the drugs; a determination unit configured to determine whether drug data corresponding to the image picked up by the image pick-up unit is present in drug data relating to a plurality of types of drugs registered in advance; and a sorting unit configured to: accommodate a drug determined to have drug data corresponding to the image into a first area of the second accommodating portion for each type; and accommodate a drug determined to have no drug data corresponding to the image into a second area different from the first area.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of the drugs; a discriminating unit configured to discriminate the type of the drug based on the image picked up by the image pick-up unit; a sorting unit configured to store the drug into the second accommodating portion for each type based on a discrimination result obtained by the discriminating unit; a drug loading stage on which the drug is to be placed in an image pick-up area of the image pick-up unit; and a swinging mechanism configured to swing the drug loading stage based on a size and a shape of the drug placed on the drug loading stage.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of the drugs; a discriminating unit configured to discriminate the type of the drug by comparing a feature of the drug extracted from the image picked up by the image pick-up unit with drug data relating to drugs that have been packaged by a packaging machine within a predetermined period in registered drug data relating to a plurality of types of drugs; and a sorting unit configured to store the drug into the second accommodating portion for each type based on a discrimination result obtained by the discriminating unit.

Further, according to one aspect of this disclosure, there is provided a drug sorting device including: a first accommodating portion configured to accommodate a plurality of types of drugs; a second accommodating portion configured to accommodate the drugs in a state of being sorted by type;

a temporary accommodating portion configured to temporarily accommodate a drug that has failed to be accommodated into the second accommodating portion; an image pick-up unit configured to pick up an image of the drugs; a discriminating unit configured to discriminate the type of the drug by comparing the image picked up by the image pick-up unit with registered drug data relating to a plurality of types of drugs; a sorting control unit configured to: determine a sorting position of the drug based on a discrimination result obtained by the discriminating unit; and store the determined sorting position and the drug data that has been used for comparison by the discriminating unit into a storage unit in association with each other; and a second discriminating unit configured to discriminate, when a drug accommodated in the temporary accommodating portion is to be accommodated into the second accommodating portion, the type of the drug by comparing the image of the drug taken out from the temporary accommodating portion, which has been picked up by the image pick-up unit, with the drug data associated with the temporary accommodating portion being the determined sorting position.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of the drugs; a discriminating unit configured to discriminate the type of the drug by: identifying, as a result of comparing a feature of the drug extracted from the image picked up by the image pick-up unit with registered drug data relating to a plurality of types of drugs, drug data having a matching degree with the feature equal to or higher than a predetermined value, as a data candidate for identifying the type of the drug; and comparing a feature of the drug extracted from an image of the drug picked up again by the image pick-up unit with the data candidate; and a sorting unit configured to store the drug into the second accommodating portion for each type based on a discrimination result obtained by the discriminating unit.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of a drug taken out from the first accommodating portion; a discriminating unit configured to discriminate the type of the drug based on the image picked up by the image pick-up unit; a sorting unit configured to store the drug into the second accommodating portion for each type based on a discrimination result obtained by the discriminating unit; a packaging unit configured to package drugs stored in the second accommodating portion; a drug feeding portion, which is connected to the packaging unit, and into which a drug to be packaged, which has been sorted by the sorting unit, is to be fed; and a drug drop prevention unit including a shutter, which functions as a bottom portion of the drug feeding portion, and is configured to open when the drug to be packaged is fed into the drug feeding portion, to thereby prevent a drug other than the drug to be packaged from dropping into the packaging unit.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of a drug taken out from the first accommodating portion; a discriminating unit configured to discriminate the type of the drug based on the image picked up by the image pick-up unit; a sorting unit configured to store the drug into the second accommodating portion for each type based on a discrimination result obtained by the discriminating unit; a packaging unit configured to package the drug sorted by the sorting unit; a drug feeding portion, which is connected to the packaging unit, and into which the drug sorted by the sorting unit is to be fed; and a drug holding unit, which includes a shutter being provided between the drug feeding portion and a pre-packaging drug placement area in the packaging unit and being openable and closable, and is configured to temporarily hold drugs fed from the drug feeding portion until all drugs to be included in one package created by the packaging unit have been fed from the drug feeding portion.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of a drug taken out from the first accommodating portion; a discriminating unit configured to discriminate the type of the drug based on the image picked up by the image pick-up unit; a sorting unit configured to store the drug into the second accommodating portion for each type based on a discrimination result obtained by the discriminating unit; a sorting container, which is attachably and detachably arranged in the second accommodating portion, and is configured to store the drug sorted by the sorting unit; and an object detection unit configured to detect, by being moved in a horizontal direction, an object that is present in an upper space above the sorting container placed in the second accommodating portion in a defined state.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of a drug taken out from the first accommodating portion; a discriminating unit configured to discriminate the type of the drug based on the image picked up by the image pick-up unit; a sorting unit configured to store the drug into the second accommodating portion for each type based on a discrimination result obtained by the discriminating unit; a packaging unit configured to package drugs stored in the second accommodating portion; a drug feeding portion, which is connected to the packaging unit, and into which the drug sorted by the sorting unit is to be fed; a feeding image pick-up unit configured to pick up an image of an inside of the drug feeding portion; a number determination unit configured to determine a number of drugs fed into the drug feeding portion based on the image picked up by the feeding image pick-up unit; and a drug movement determination unit configured to determine to move the drug from the drug feeding portion to the packaging unit when the number determination unit determines that the number of drugs fed into the drug feeding portion is one, wherein the number determination unit is configured to determine, in a case where the number determination unit has determined that the image includes a plurality of drugs, that the number of drugs fed into the drug feeding portion is one when no drug is included in an image picked up again by the feeding image pick-up unit under a state in which the drug fed into the drug feeding portion has been taken out.

Further, according to one aspect of this disclosure, there is provided a drug sorting device including: a first accommodating portion configured to accommodate a plurality of types of drugs; a second accommodating portion configured to accommodate the drugs in a state of being sorted by type; an image pick-up unit configured to pick up an image of a drug taken out from the first accommodating portion; a discriminating unit configured to discriminate the type of the drug based on the image picked up by the image pick-up unit; a sorting unit configured to store the drug into the second accommodating portion for each type based on a discrimination result obtained by the discriminating unit; a sorting container, which is attachably and detachably arranged in the second accommodating portion, and is configured to store the drug sorted by the sorting unit; a container image pick-up unit configured to pick up an image of an inside of an unused sorting container exhibited before the sorting unit sorts the drug or an inside of a sorting container exhibited after all drugs stored in the sorting container have been dispensed to a packaging unit configured to package the drugs; a storage determination unit configured to determine whether the drug is stored in the sorting container based on the image picked up by the container image pick-up unit; and an information storage control unit configured to store, when the storage determination unit has determined that the drug is stored in the sorting container, storage information indicating that the drug is stored in the sorting container in association with container identification information for identifying the sorting container.

Advantageous Effects of Invention

According to the drug sorting device of one aspect of this disclosure, it is possible to recognize the drug itself and automatically sort the drug. In addition, it is possible to sort the drug irrespective of whether or not the drug data has been registered.

BRIEF DESCRIPTION OF DRAWINGS

FIGS. 2A and 2B are views for illustrating a configuration example of the drug sorting device, in which FIG. 2A is a perspective view of the drug sorting device, and FIG. 2B is a perspective view for illustrating a basic configuration of a drug sorting area.

FIGS. 16A to 16D are views for illustrating an example of a packaging machine, in which FIG. 16A is a front view of the packaging machine, FIG. 16B is a view for illustrating an example of a cassette storage mechanism, and FIG. 16C and FIG. 16D are views for illustrating a use example of a replenishment table.

FIG. 19 is a diagram for illustrating an example of a user setting image.

FIGS. 24A and 24B are views for illustrating an example of a drug having an elongated shape, in which FIG. 24A is a plan view, and FIG. 24B is a side view.

FIGS. 34A to 34E are views for illustrating a configuration example of a packaging mechanism, in which FIG. 34A is a view for schematically illustrating a configuration example of a part of the packaging mechanism, FIG. 34B and FIG. 34C are views for illustrating an opening and closing operation in a upper shutter mechanism, and FIG. 34D and FIG. 34E are views for illustrating an opening and closing operation in a lower shutter mechanism.

FIG. 37A is a diagram for illustrating an example of a similar drug registration image, and FIG. 37B is a diagram for illustrating an example of a similar drug selection image.

DESCRIPTION OF EMBODIMENTS

First Embodiment

[Overview of Drug Sorting Device 1]

Figure 1:
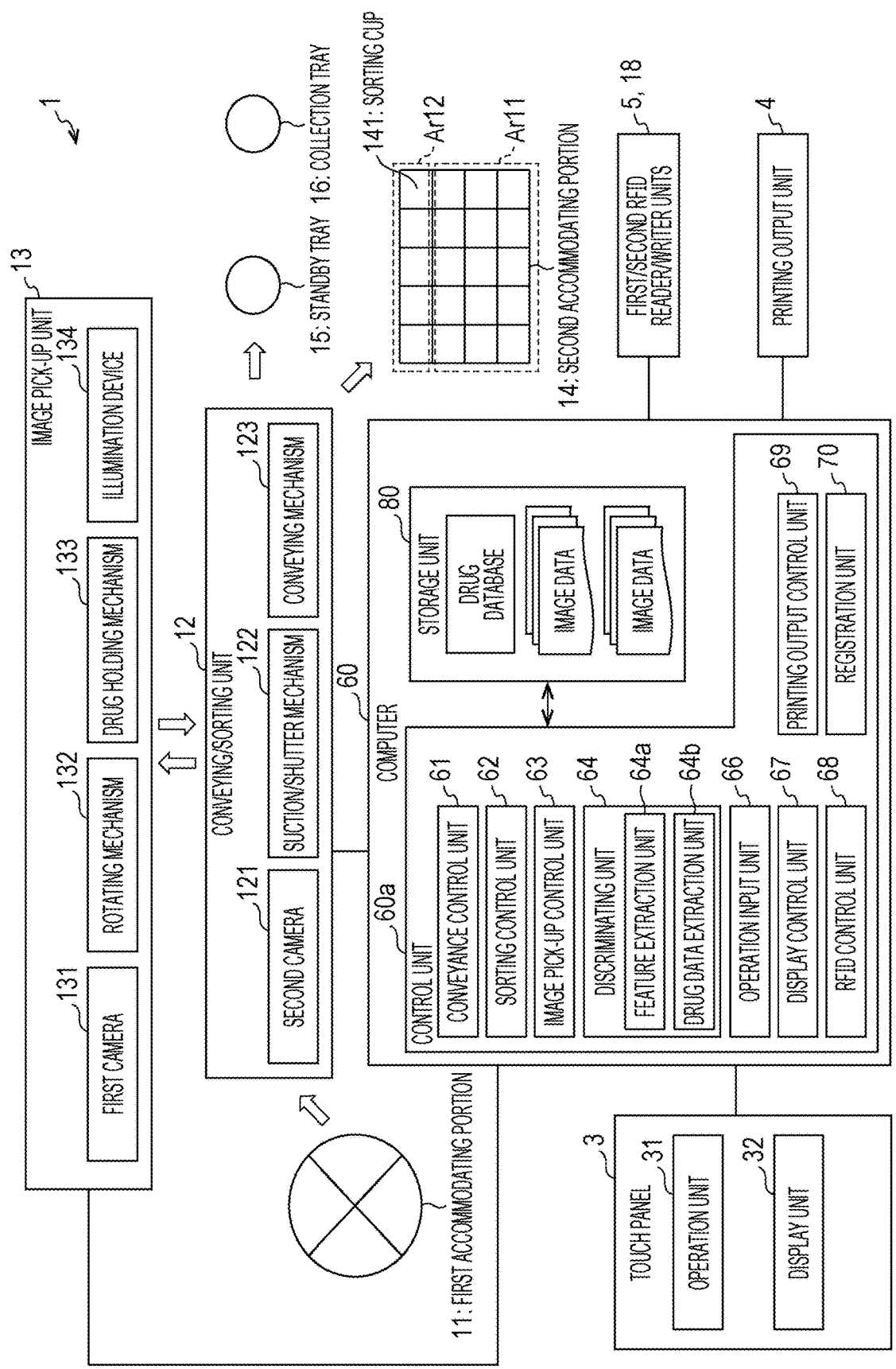
FIG. 1 is a block diagram for illustrating an overall configuration of a drug sorting device.
Figure 2B:
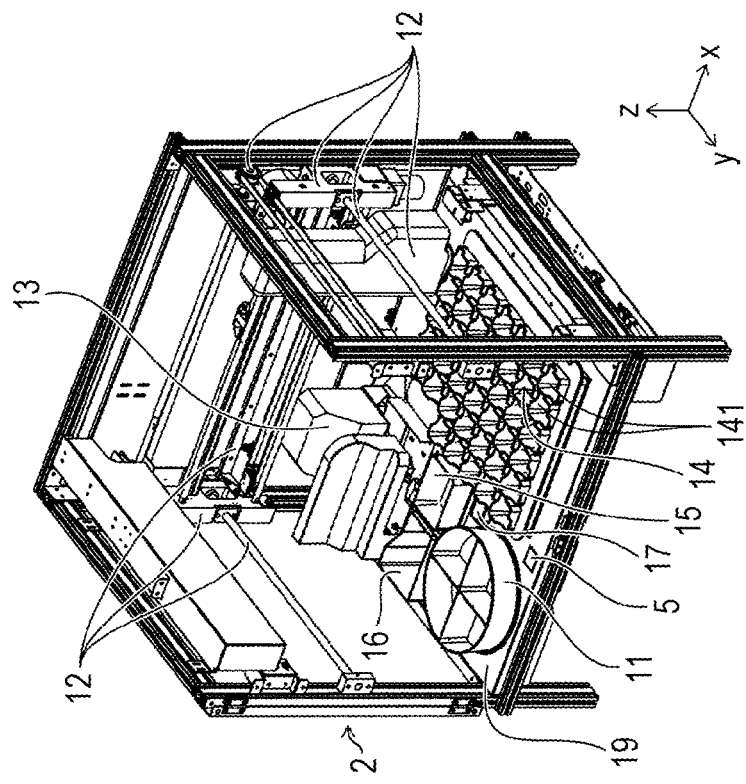
Figure 2A:
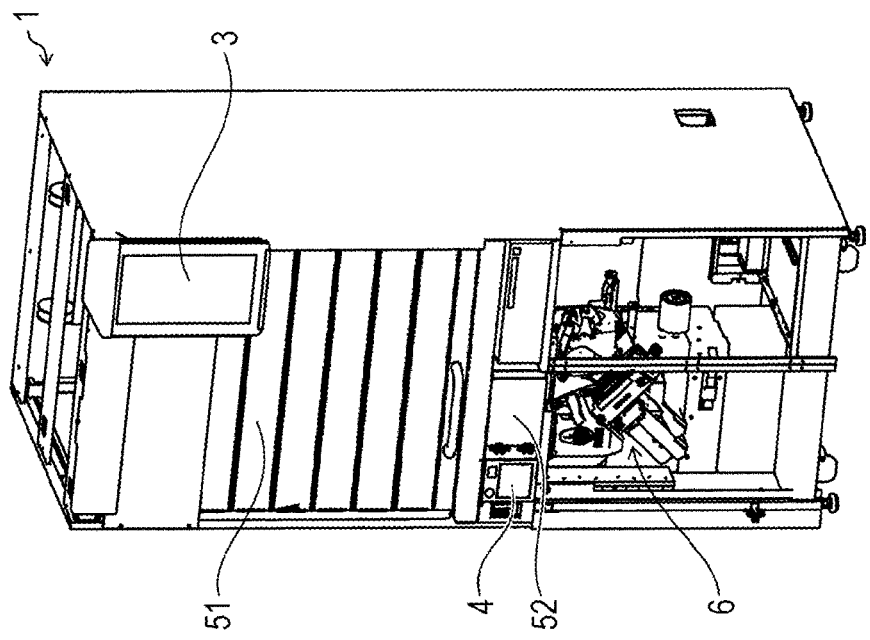

First, an overview of the drug sorting device 1 is described with reference to FIG. 1 and FIGS. 2A and 2B. FIG. 1 is a block diagram for illustrating an overall configuration of the drug sorting device 1. FIGS. 2A and 2B are views for illustrating a configuration example of the drug sorting device 1, in which FIG. 2A is a perspective view of the drug sorting device 1, and FIG. 2B is a perspective view for illustrating a basic configuration of a drug sorting area 2. As illustrated in FIG. 1, FIG. 2A, and FIG. 2B, the drug sorting device 1 includes the drug sorting area 2, a touch panel 3, a printing output unit 4, and a packaging mechanism 6.

The drug sorting device 1 is configured to pick up an image of each of a plurality of types of drugs and discriminate the type of a drug based on an image obtained as a result of the image pick-up to sort the drugs by type. Specifically, this processing is performed in the drug sorting area 2. The drug sorting area 2 (internal configuration of the drug sorting device 1) is described later. The drugs sorted by type are visually inspected by a user, and are then packaged or returned to a drug shelf or a packaging machine.

In an embodiment of this disclosure, the plurality of types of drugs are drugs that are not accommodated in a container or the like or drugs that are not subjected to packaging or the like. This embodiment is described by taking tablets or capsules as an example of the plurality of types of drugs. This embodiment is also described on the assumption that a plurality of types of drugs are returned drugs. The returning of a drug includes a case in which an adopted drug at a pharmacy or a hospital is returned as a "return drug" at this pharmacy or this hospital and a case in which not this adopted drug but a "brought drug" that can include a drug issued at another pharmacy or another hospital is returned to this pharmacy or this hospital. In other words, the returned drug has a concept including at least one of the "return drug" and the "brought drug" which are described above. The drug sorting device 1 can automatically perform processing from the image pick-up to the sorting after a drug is returned.

The touch panel 3 is configured to cause an operation unit 31 to receive various user inputs, and cause a display unit 32 to display various images (for example, image indicating progress of drug sorting and an image for visual inspection).

The printing output unit 4 is configured to print a journal representing drug data (for example, data indicating a drug name, a manufacturer, or components thereof) relating to a drug subjected to the visual inspection based on the user input after the visual inspection. The drug data may include image data representing a drug-specific image.

The packaging mechanism 6 is configured to package the sorted drugs. The packaging mechanism 6 is an optional mechanism. When the packaging mechanism 6 is provided to the drug sorting device 1, the drug sorting device 1 can collectively perform processing from the sorting of the returned drug to the packaging after the visual inspection. In particular, when drugs are fed into the packaging mechanism 6 by a conveying/sorting unit 12, the above-mentioned processing from the sorting to the packaging can be automatically performed except for the visual inspection.

As the packaging mechanism 6, it is possible to adopt a packaging unit of a tablet packaging machine or powdered drug packaging machine, which has hitherto been adopted. In this case, for example, the drugs in a sorting cup 141 sorted by the same drug type can be packaged in one package or a plurality of packages.

The drug sorting device 1 also includes a first radio frequency identifier (RFID) reader/writer unit 5. As illustrated in FIG. 2B, the first RFID reader/writer unit 5 is provided on a pedestal 19 on a drug take-out side.

The first RFID reader/writer unit 5 is configured to read data relating to drugs stored in each sorting cup 141, which is stored in an RFID tag (not shown) provided on a bottom portion of each sorting cup 141 of a second accommodating portion 14. Examples of the data to be read include the number of stored drugs, drug data, and image data acquired by an image pick-up unit 13. The data to be read may include drug data (drug data after the visual inspection) determined through the visual inspection. In addition, the drug data after the visual inspection may be written to the above-mentioned RFID tag. The drug data after the visual inspection is used when the drug stored in the corresponding sorting cup 141 is to be (1) packaged by the packaging mechanism 6 or a packaging machine different from the drug sorting device 1 or (2) returned to the drug shelf.

As illustrated in FIG. 2A, the drug sorting device 1 also includes an opening/closing shutter 51 and an opening/closing door 52, which allow the drug take-out side to be opened and closed. In order to move a drug accommodated in the second accommodating portion 14 to the packaging mechanism 6, the drug sorting device 1 includes, for example, a package hopper (not shown) configured to temporarily hold this drug and a movement passage (not shown) for moving the drug held in the package hopper to the packaging mechanism 6. In addition, at least the movement passage is removable. Through the opening of the opening/closing door 52, the movement passage can be taken out to the outside of the drug sorting device 1.

[Basic Configuration of Drug Sorting Area 2]

Next, the basic configuration of the drug sorting area 2 (internal configuration of the drug sorting device 1) is described with reference to FIG. 1 and FIG. 2B.

As illustrated in FIG. 1 and FIG. 2B, the drug sorting area 2 mainly includes, as hardware, a first accommodating portion 11, the conveying/sorting unit 12 (sorting unit), the image pick-up unit 13, the second accommodating portion 14, a standby tray 15, a collection tray 16, a drug feeding port 17, and a second RFID reader/writer unit 18. Each member except the conveying/sorting unit 12 is provided on the pedestal 19. Main functions of the conveying/sorting unit 12, the image pick-up unit 13, and the second RFID reader/writer unit 18 are described in detail in description of their corresponding processing procedures described later.

The first accommodating portion 11 is configured to accommodate a plurality of types of drugs, which have been returned by the user, in a mixed state. In this embodiment, the first accommodating portion 11 is divided into a plurality of accommodating portions. In this case, for example, when all the drugs accommodated in one accommodating portion have been conveyed by the conveying/sorting unit 12, the drugs accommodated in an accommodating portion adjacent to the above-mentioned accommodating portion become objects to be conveyed. In addition, the first accommodating portion 11 may be provided so as to be pivotable with respect to a Z-axis (center of a cylindrical shape). In this case, a control unit 60a of a computer 60 may pivot the first accommodating portion 11 so that the conveying/sorting unit 12 can easily acquire the drug at, for example, a timing at which one accommodating portion becomes vacant.

The second accommodating portion 14 includes a plurality of sorting cups 141 configured to accommodate the drugs in a state of being sorted by type. The control unit 60a discriminates the type of a drug based on the image of the drug picked up by the image pick-up unit 13, and determines the sorting cup 141 to be used for storing this drug based on a result of the discrimination. This drug is conveyed to and stored into the determined sorting cup 141 by the conveying/sorting unit 12.

The standby tray 15 is an accommodating portion for temporarily placing drugs. For example, when drugs are stored in all the sorting cups 141, a drug discriminated as having a type other than the types of those stored drugs by the control unit 60a is temporarily placed in the standby tray 15. In this case, after drugs are removed from a sorting cup 141, the drug may be conveyed from the standby tray 15 to this sorting cup 141.

In this embodiment, an estimated drug (described later) estimated to be a drug may be temporarily placed in the standby tray 15. When the estimated drug is temporarily placed, the estimated drug is conveyed to a predetermined area of the second accommodating portion 14 depending on the discrimination result obtained by the control unit 60a.

The collection tray 16 is an accommodating portion for storing items (for example, foreign matter other than drugs) having a type that has failed to be discriminated by the control unit 60a. Examples of foreign matter other than drugs include a fragment of a press through pack (PTP) sheet. The fragment of the PTP sheet may get mixed into the first accommodating portion 11 when the drug is returned. In addition, the control unit 60a stores a drug registered in the drug database as a drug to be discarded or a drug wished to be discarded by the user (for example, drug having an old manufacturing date) into the collection tray 16.

The drug feeding port 17 is used for conveying the drug stored in the second accommodating portion 14 to the packaging mechanism 6 by the conveying/sorting unit 12 when the drug sorting device 1 includes the packaging mechanism 6. It is to be understood that the drug feeding port 17 is not required when the drug sorting device 1 does not include the packaging mechanism 6.

As illustrated in FIG. 1, the drug sorting device 1 also includes the computer 60 configured to collectively control the above-mentioned members (pieces of hardware) of the drug sorting device 1. The computer 60 mainly includes, as the control unit 60a (software), a conveyance control unit 61, a sorting control unit 62, an image pick-up control unit 63, a discriminating unit 64, an operation input unit 66, a display control unit 67, an RFID control unit 68, a printing output control unit 69, and a registration unit 70. The conveyance control unit 61, the sorting control unit 62, the image pick-up control unit 63, the discriminating unit 64, and the registration unit 70 are described in detail in description of their corresponding processing procedures described later.

The operation input unit 66 and the display control unit 67 are configured to control the operation unit 31 and the display unit 32 of the touch panel 3, respectively. The RFID control unit 68 is configured to control the first RFID reader/writer unit 5 and the second RFID reader/writer unit 18. The printing output control unit 69 is configured to control the printing output unit 4 based on the user input received by the operation input unit 66. When the drug sorting device 1 includes the packaging mechanism 6, the control unit 60a includes a packaging control unit configured to control the packaging mechanism 6.

The computer 60 also includes a storage unit 80. The storage unit 80 stores, for example, a drug database (drug master) for managing the drug data relating to a plurality of types of drugs and image data representing an image picked up by a first camera 131. The various kinds of data stored in the storage unit 80 are not required to be managed by the storage unit 80, and may be managed by, for example, an external device. In this case, the control unit 60a may acquire the above-mentioned various kinds of data from this external device through a communication line, for example, the Internet, as the requirement arises. In addition, the drug database may be updated by adding new drug data.

[Overview of Processing in Drug Sorting Device 1]

In the drug sorting device 1, the conveying/sorting unit 12 conveys each drug returned to the first accommodating portion 11 to the image pick-up unit 13. The image pick-up unit 13 sequentially picks up an image of each of the conveyed drugs. The control unit 60a discriminates the type of each drug based on the picked-up image, and at the same time, determines a sorting position of each drug subjected to the discrimination in the second accommodating portion 14. The conveying/sorting unit 12 conveys each drug to the determined sorting position. Then, information on the drug stored in the second accommodating portion 14 is written to the RFID tag of the sorting cup 141, stored in the storage unit 80, or displayed on the touch panel 3. In addition, after the sorting of the drugs is completed or midway through the sorting, the user operates the touch panel 3 to perform the visual inspection, the packaging, or other such processing. Each processing step is described in detail below.

[Drug Conveying Processing to Image Pick-Up Unit 13]

First, drug conveying processing from the first accommodating portion 11 to the image pick-up unit 13 is described with reference to FIG. 1 and FIG. 2A.

Specifically, the conveying/sorting unit 12 is configured to convey a drug accommodated in the first accommodating portion 11 to a receiving area Ar1 (see FIG. 3B) in which the image pick-up unit 13 receives the drug. The conveyance control unit 61 controls this conveying processing performed by the conveying/sorting unit 12.

The conveying/sorting unit 12 includes a second camera 121, a suction/shutter mechanism 122, and a conveying mechanism 123.

The second camera 121 successively picks up an image of the first accommodating portion 11 in order to identify a drug to be set as an object to be conveyed. The image pick-up control unit 63 controls the image pick-up processing of the second camera 121. The second camera 121 is provided at an end portion of the conveying/sorting unit 12 (specifically, at least in a casing including the suction/shutter mechanism 122) on a side opposed to the pedestal 19. The second camera 121 may be provided at a tip end portion of a suction mechanism described later. The image pick-up control unit 63 analyzes the picked-up image to determine whether or not this image includes a drug. When the conveyance control unit 61 determines that a drug is included, for example, the conveyance control unit 61 brings the above-mentioned tip end portion closer to the first accommodating portion 11, and identifies the drug included in the image picked up at that time as the drug to be conveyed.

The suction/shutter mechanism 122 includes the suction mechanism for sucking a drug identified as an object to be conveyed and a shutter mechanism for preventing the drug sucked by the suction mechanism from dropping. The suction mechanism is provided so as to be movable in a Z-axis direction. The shutter mechanism is provided so as to be movable in substantially parallel to the XY-plane toward a front side of the above-mentioned end portion.

At a time of drug acquisition, the suction mechanism extends from the above-mentioned end portion, sucks the identified drug at its tip end portion, and then returns to a position of the above-mentioned end portion. In this state, the conveyance control unit 61 moves the shutter mechanism to a position opposed to the above-mentioned end portion, and maintains the position of the shutter mechanism (brings the shutter mechanism to a closed state) during drug conveyance. When the conveyance control unit 61 moves the suction/shutter mechanism 122 to a position opposed to a drug loading stage 133a (see FIG. 3B) of a drug holding mechanism 133 arranged in the receiving area Ar1, the conveyance control unit 61 moves the shutter mechanism to a position that does not face the above-mentioned end portion (brings the shutter mechanism to an open state). Then, after the suction mechanism is extended from the above-mentioned end portion, the drug is placed on the drug loading stage 133a by canceling a sucked state.

The conveying mechanism 123 moves the suction/shutter mechanism 122 in X-axis and Y-axis directions under control of the conveyance control unit 61. The conveying mechanism 123 enables the movement of the suction/shutter mechanism 122 at a time of searching for a drug to be conveyed above the first accommodating portion 11 or the drug conveyance from the first accommodating portion 11 to the drug loading stage 133a. In addition, in drug sorting processing described later, the drug can be conveyed from the drug loading stage 133a to the second accommodating portion 14, the standby tray 15, or the collection tray 16.

[Drug Image Pick-Up Processing]

Figure 3A:
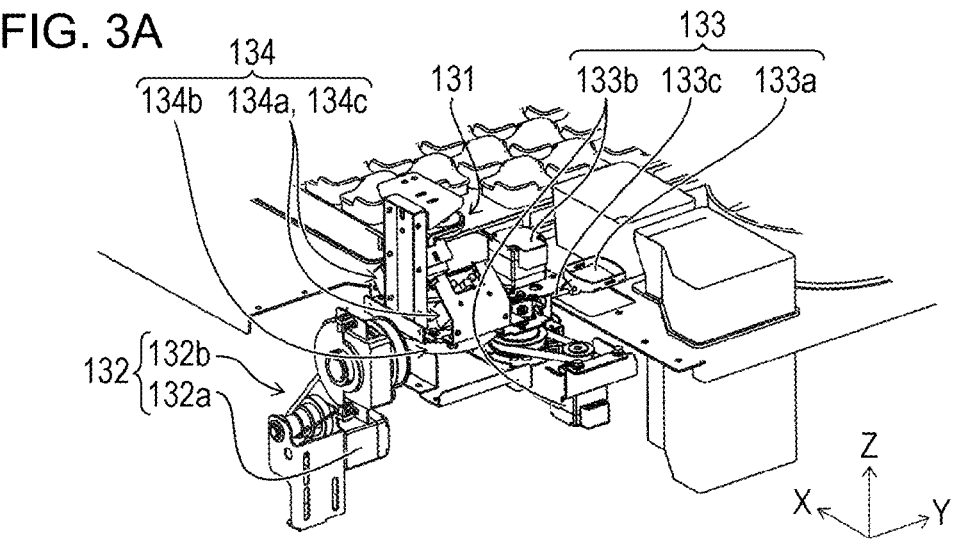
FIG. 3A and FIG. 3B are perspective views for illustrating an overall configuration of an image pick-up unit.
Figure 3B:
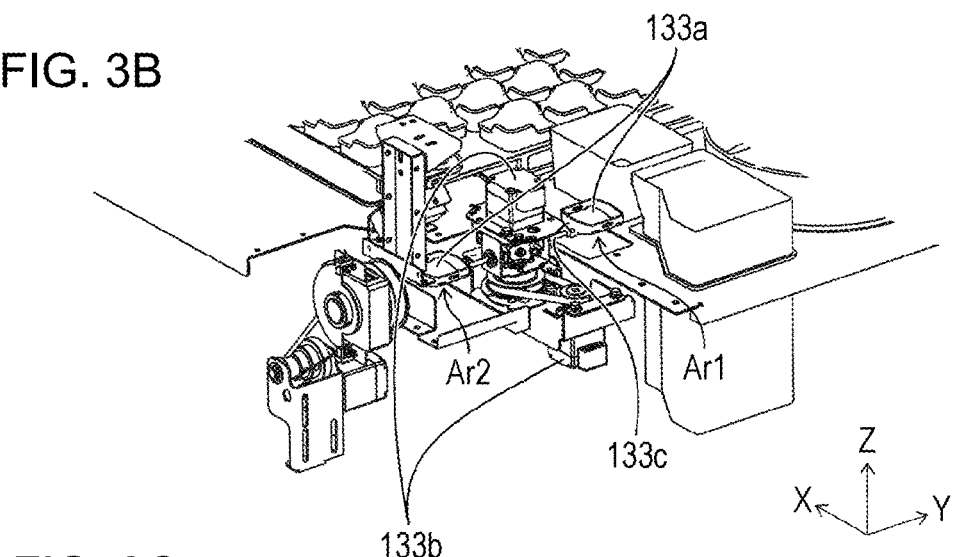
Figure 3C:
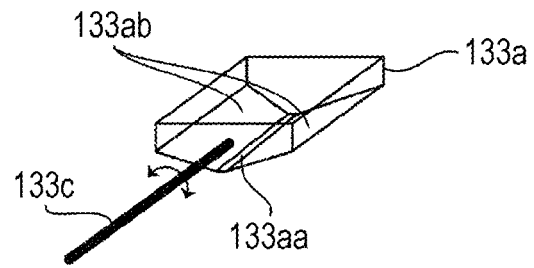
FIG. 3C is a perspective view for illustrating an example of a drug loading stage.
Figure 4A:
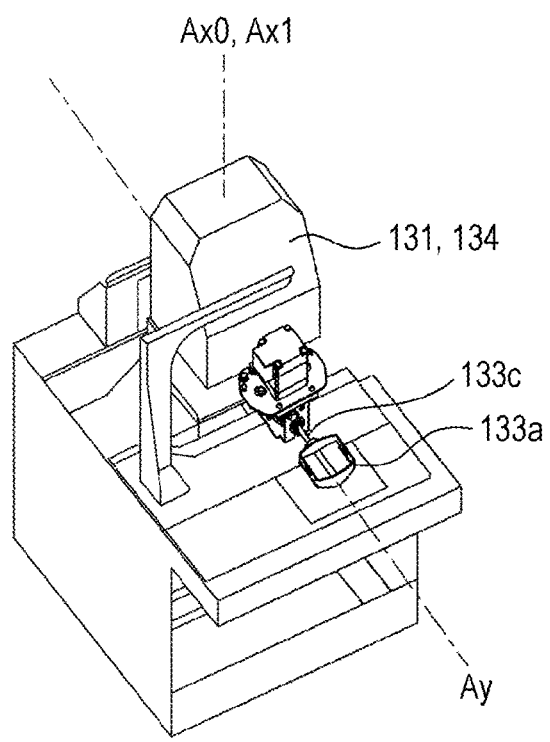
FIG. 4A and FIG. 4B are views for illustrating swiveling of the image pick-up unit.
Figure 4B:
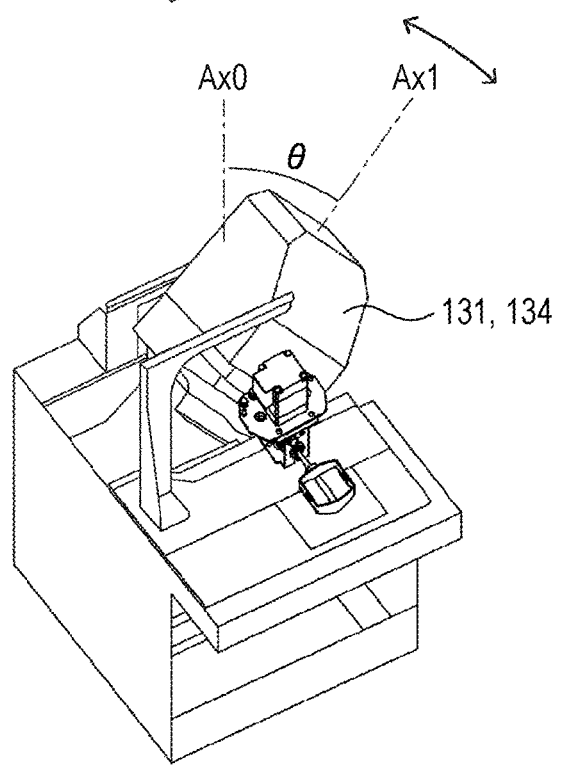

Next, the drug image pick-up processing performed by the image pick-up unit 13 is described with reference to FIG. 1, FIG. 2B, FIGS. 3A to 3C, and FIGS. 4A and 4B. FIG. 3A and FIG. 3B are perspective views for illustrating an overall configuration of the image pick-up unit 13, and FIG. 3C is a perspective view for illustrating an example of the drug loading stage 133a. FIG. 4A and FIG. 4B are views for illustrating swiveling of the image pick-up unit 13. The above-mentioned drug image pick-up processing is mainly performed by the image pick-up unit 13 and the image pick-up control unit 63.

Specifically, the image pick-up unit 13 is configured to pick up an image of a drug placed on the drug loading stage 133a and arranged in an arrangement area Ar2 (image pick-up area) for arranging a drug whose image is to be picked up, which is illustrated in FIG. 3B. The image pick-up control unit 63 controls this image pick-up processing performed by the image pick-up unit 13, swiveling movement of the first camera 131 and an illumination device 134, and movement of the drug holding mechanism 133. As illustrated in FIG. 1 and FIGS. 3A to 3C, the image pick-up unit 13 includes the first camera 131 (image pick-up unit), a rotating mechanism 132 (pivoting unit), the drug holding mechanism 133 (drug loading stage and moving mechanism), and the illumination device 134 (ultraviolet light irradiation unit and visible light irradiation unit).

The first camera 131 is configured to pick up an image of a drug arranged in the arrangement area Ar2 opposed to the first camera 131 in order to discriminate the type of the drug in the discriminating unit 64 described later. The drug holding mechanism 133 is a mechanism for holding a drug, and as illustrated in FIG. 3A and FIG. 3B, includes the drug loading stage (petri dish) 133a, a swiveling mechanism 133b (moving mechanism), and a shaft portion 133c for connecting the drug loading stage 133a and the swiveling mechanism 133b. The drug loading stage 133a is used for placing the drug whose image is to be picked up. The swiveling mechanism 133b is configured to move the drug loading stage 133a. Specifically, the swiveling mechanism 133b is configured to swivel the drug loading stage 133a with respect to the XY-plane and swivel the shaft portion 133c in a circumferential direction of the shaft portion 133c.

When the drug conveyed from the first accommodating portion 11 is placed on the drug loading stage 133a, the image pick-up control unit 63 drives the swiveling mechanism 133b to move this drug loading stage 133a from the receiving area Ar1 to the arrangement area Ar2. After that, the image pick-up control unit 63 controls at least the first camera 131 and the illumination device 134 to pick up an image of the drug arranged in the arrangement area Ar2. The picked-up image is stored in the storage unit 80 as image data. For example, after the image pick-up is completed, the image pick-up control unit 63 drives the swiveling mechanism 133b to move the drug loading stage 133a on which the drug whose image has been picked up is placed, from the arrangement area Ar2 to the receiving area Ar1.

In this embodiment, two drug loading stages 133a are provided to a tip end portion (end portion) of the shaft portion 133c. The swiveling mechanism 133b swivels the shaft portion 133c so that, when one drug loading stage 133a is arranged in the arrangement area Ar2, the other drug loading stage 133a is arranged in the receiving area Ar1. At a time of the image pick-up of the drug in the arrangement area Ar2, the drug is conveyed from the first accommodating portion 11 to the drug loading stage 133a present in the receiving area Ar1 by the conveying/sorting unit 12, to thereby enable continuous drug image pick-up processing. It is premised that no drug is placed on this drug loading stage 133a after, for example, the drug sorting processing with respect to the second accommodating portion 14.

In addition, in this embodiment, the drug loading stage 133a has transparency. Therefore, the first camera 131 can pick up images of the drug placed on the drug loading stage 133a from various directions through the drug loading stage 133a.

As illustrated in FIG. 3C, the drug loading stage 133a may also have a substantially V-shaped cross section with its bottom portion being recessed. In addition, as illustrated in FIG. 3B and FIGS. 4A and 4B, when the drug loading stages 133a are arranged in the receiving area Ar1 and the arrangement area Ar2, a groove direction of the substantially V-shaped cross section (extending direction of the shaft portion 133c) is substantially parallel to a swivel axis Ay of an image pick-up mechanism (described later) employed by the rotating mechanism 132. The bottom portion of the drug loading stage 133a is not required to have an acute V-shape. As illustrated in FIG. 3C, the bottom portion may include a bottom surface portion 133aa and slope surface portions 133ab sloped from two opposed spots of the bottom surface portion 133aa. It suffices that the bottom portion has such a shape as to enable information (inscribed information or printed information) indicated by an inscription or a print on a drug to be recognized even when the bottom portion is viewed from a back side of the drug loading stage 133a (even when an image of the bottom portion is picked up) and as to fix the drug.

In a case where the drug is a capsule or a deformed tablet (for example, rugby ball shape), when the bottom portion of the drug loading stage 133a is flat, there is a possibility that the drug may not be oriented in the same direction on the XY-plane and it is difficult to acquire a clear image (inscribed information or printed information) of the drug. When the cross section is substantially V-shaped, the capsule or the deformed tablet can be fitted into a lowermost end portion to fix this drug. Therefore, it becomes easier to acquire a clear image of the drug. In a case of a tablet, for example, the shaft portion 133c may be swiveled in the circumferential direction of the shaft portion 133c to cause a flat surface portion (slope surface portion 133ab) of the drug loading stage 133a to be opposed to the first camera 131, to thereby reliably immobilize this drug.

The swiveling mechanism 133b may be further configured to vibrate (subtly move or shake) the drug loading stage 133a. In this case, for example, the capsule placed on the drug loading stage 133a can be vibrated and rolled to orient a printed portion of the capsule toward a predetermined direction (for example, this portion can be opposed to the first camera 131 arranged at an initial position described later). In addition, for example, even when a cylindrical-shaped tablet (having a circular bottom portion) is placed while standing on the above-mentioned flat surface portion, the above-mentioned vibration enables the tablet to be tilted sideways (to be arranged so that the bottom portion of the tablet is opposed to this flat surface portion).

The illumination device 134 is configured to emit light emitted to the drug at the time of the image pick-up of the drug under control of the image pick-up control unit 63. As illustrated in FIG. 3A, the illumination device 134 includes the visible light irradiation unit (first irradiation unit 134a and second irradiation unit 134b) configured to irradiate the drug with visible light and an ultraviolet light irradiation unit 134c configured to irradiate the drug with ultraviolet light.

The first irradiation unit 134a and the second irradiation unit 134b are configured to irradiate the drug with white light as the visible light. The first irradiation unit 134a is a bar-shaped visible light source (bar illumination), and the second irradiation unit 134b is a ring-shaped visible light source (ring illumination). The first camera 131 receives visible light emitted from the first irradiation unit 134a or the second irradiation unit 134b and reflected by the drug, to thereby acquire an image (visible light image) based on the visible light. The image pick-up control unit 63 outputs image data indicating the visible light image acquired by the first camera 131 to the discriminating unit 64.

The ultraviolet light irradiation unit 134c is configured to irradiate the drug with ultraviolet light (for example, light having a peak wavelength of 365 nm or more and 410 nm or less), to thereby excite the components included in the drug. Thus, fluorescence (for example, light having a peak wavelength of 410 nm or more and 800 nm or less) is extracted from the drug. The first camera 131 receives the fluorescence emitted from the drug, to thereby acquire an image (ultraviolet light image) based on ultraviolet light. The image pick-up control unit 63 outputs image data indicating the ultraviolet light image acquired by the first camera 131 to the discriminating unit 64.

As illustrated in FIGS. 3A to 3C and FIGS. 4A and 4B, the rotating mechanism 132 pivots the first camera 131 so as to swivel the first camera 131 around the arrangement area Ar2 (drug loading stage 133a arranged at this position) in which the drug whose image is to be picked up is arranged. The first camera 131 picks up images of the drug arranged in the arrangement area Ar2 from a plurality of positions to which the pivoting has been performed by the rotating mechanism 132. Specifically, the image pick-up mechanism including the first camera 131 and the illumination device 134 is pivoted so as to be swiveled around the arrangement area Ar2. Therefore, the first camera 131 can pick up images of the drug from a plurality of directions while maintaining a positional relationship between the first camera 131 and the illumination device 134 with respect to the arrangement area Ar2.

As illustrated in FIG. 3A, the rotating mechanism 132 includes an image pick-up mechanism drive unit 132a and a power transmission mechanism 132b. The image pick-up mechanism drive unit 132a is configured to generate power for swiveling the image pick-up mechanism around the arrangement area Ar2. The power transmission mechanism 132b is configured to transmit the power generated by the image pick-up mechanism drive unit 132a to the image pick-up mechanism. The image pick-up mechanism drive unit 132a is driven by the control of the image pick-up control unit 63 to change a position of the image pick-up mechanism around the arrangement area Ar2.

The rotating mechanism 132 swivels the image pick-up mechanism between an initial position and a position opposed to the initial position. The initial position is a position in a direction substantially perpendicular to the arrangement area Ar2 and is also a position above the arrangement area Ar2. The position opposed to the initial position is a position in a direction substantially perpendicular to the arrangement area Ar2, and is also a position below the arrangement area Ar2. This position can also be expressed as a position in which the first camera 131 is opposed to the bottom portion of the drug loading stage 133a present in the arrangement area Ar2.

As illustrated in FIGS. 4A and 4B, an axis passing through a center of the arrangement area Ar2 in parallel to the Z-axis is set as an axis Ax0, and an axis passing through the center of the arrangement area Ar2 and a center of the image pick-up mechanism is set as an axis Ax1. In addition, an angle formed by the axis Ax0 and the axis Ax1 is set as $\theta$. In this embodiment, the rotating mechanism 132 arranges the image pick-up mechanism at any one of positions of $\theta=0°$ (initial position), 45°, 135°, and 180°. FIG. 4A is an illustration of a case in which the image pick-up mechanism is arranged at the position of θ=0°, and FIG. 4B is an illustration of a case in which the image pick-up mechanism is swiveled from the initial position to be arranged at the position of θ=45°.

Through the swiveling of the image pick-up mechanism around the arrangement area Ar2 in this manner, the images of the drug can be picked up from the plurality of directions while the drug is fixed in the arrangement area Ar2. In addition, even when the drug (tablet) is standing even after the drug loading stage 133a has been shaken, the information indicated by, for example, an inscription attached to the drug can be acquired through the image pick-up from an oblique direction (θ=45° or 135°).

The images of this drug may be picked up from a plurality of directions by fixing the image pick-up mechanism and pivoting the drug.

(Image Pick-Up Position Control)

Next, an example of position control of the image pick-up mechanism is described. The image pick-up control unit 63 first sets the image pick-up mechanism at an initial position, and causes the first camera 131 to pick up an image of the drug arranged in the arrangement area Ar2 at this initial position. At this time, the first camera 131 acquires visible light images (two visible light images) based on visible light from the first irradiation unit 134a and visible light from the second irradiation unit 134b, and at the same time, acquires an ultraviolet light image based on ultraviolet light from the ultraviolet light irradiation unit 134c.

Subsequently, the image pick-up control unit 63 sets the image pick-up mechanism at the position opposed to the initial position, and causes the first camera 131 to pick up an image of the drug arranged in the arrangement area Ar2 at this position to acquire two visible light images and an ultraviolet light image. The discriminating unit 64 discriminates the type of the drug by analyzing those six images. When the type of the drug cannot be identified as one type, the image pick-up control unit 63 causes the first irradiation unit 134a and the second irradiation unit 134b to emit visible light at the positions of θ=45° and 135°, and causes the first camera 131 to pick up an image of the drug. The discriminating unit 64 analyzes the visible light image at this time to discriminate the type of the drug.

The position control of the image pick-up mechanism is not limited to the above, and various methods can be employed. For example, the image pick-up may be performed from the initial position after the image is picked up from the position opposed to the initial position. In another example, discrimination processing may be performed on the drug based on a visible light image picked up from the position of θ=45°, and only when the type of the drug cannot be identified as one, a visible light image may be acquired from the position of θ=135°. In another example, only ultraviolet light images may be acquired at the initial position and the position opposed to the initial position, and after the discrimination processing for the drug is performed based on this ultraviolet light image, a visible light image may be acquired at this position. In another example, visible light images and ultraviolet light images may be acquired at all positions.

[Image Processing/Discrimination Processing]

Next, image processing for the image picked up by the image pick-up unit 13 and discrimination processing for the drug based on a result of the image processing are described with reference to FIG. 1. The above-mentioned image processing is mainly performed by the image pick-up control unit 63, and the above-mentioned discrimination processing is mainly performed by the discriminating unit 64.

The discriminating unit 64 discriminates the type of the drug based on the image of the drug picked up by the first camera 131. Specifically, the discriminating unit 64 discriminates the type of the drug based on an image pick-up result (visible light image) of the drug whose image has been picked up under a state of being irradiated with the visible light from the first irradiation unit 134a or the second irradiation unit 134b. In addition, the discriminating unit 64 discriminates the type of the drug based on an image pick-up result (ultraviolet light image) of the drug whose image has been picked up under a state of being irradiated with the ultraviolet light.

The discriminating unit 64 executes image analysis on each of the visible light image and/or the ultraviolet light image, to thereby extract a feature of the drug included in each of those images. In other words, the discriminating unit 64 includes a feature extraction unit 64a (identification information extraction unit) configured to extract the feature of the drug. Examples of the feature of the drug include a size, a shape, an inscription, a print, a division line, and a representative color (color of an inscribed or printed area). When, for example, optical character recognition (OCR) is performed, identification information (identification information for identifying a drug) representing a drug name (for example, identification code) or a manufacturer indicated by an inscription or a print and other information including an expiration date are extracted as the features of the drug. In a case of an ultraviolet light image, the feature of the drug includes a representative color of the drug in the image. The discriminating unit 64 stores the extracted feature of each drug in the storage unit 80 in association with the image data of the drug. The feature of the drug may be extracted by a known technology.

The discriminating unit 64 discriminates the type of the drug by comparing the feature of each drug against the drug database. In other words, the discriminating unit 64 includes a drug data extraction unit 64b configured to narrow down candidates for drug data relating to the drug whose image has been picked up from within the drug database through use of, for example, pattern matching based on the extracted feature of the drug. In this case, for example, at least one of the above-mentioned size, shape, inscription, print, division line, and representative color is used to narrow down drug data candidates. After that, the discriminating unit 64 performs, for example, the OCR to read, for example, the identification information indicated on the inscription or the print, and further narrows down types of the drug from the above-mentioned candidates through use of, for example, the pattern matching.

In addition, even in a case where the feature (target feature) of the drug extracted through use of, for example, the pattern matching is not included in the drug database, when the drug is estimated to be a drug (tablet or capsule) based on at least a part of the target feature, the discriminating unit 64 discriminates the type of the drug as the estimated drug. In this case, the estimated drug can also be set as an object to be sorted into the second accommodating portion 14 or the standby tray 15. In this embodiment, the estimated drug may first be temporarily placed in the standby tray 15.

In this manner, the discriminating unit 64 (determination unit) determines whether or not the drug data corresponding to the image (image data) picked up by the first camera 131 is present in the drug data (drug database) relating to a plurality of types of drugs registered in advance.

The discriminating unit 64 outputs the discrimination result of the type of the drug to the sorting control unit 62.

For example, when the type of the drug can be identified as one or when the number of candidates is narrowed down to within a predetermined number, drug data relating to this drug is output as the discrimination result. In this case, the discriminating unit 64 stores the drug data relating to this drug in the storage unit 80 in association with the image data on this drug.

When the type of the drug is discriminated as the estimated drug, the discriminating unit 64 outputs the feature of the drug (feature of an object estimated as the estimated drug) as the discrimination result. Meanwhile, when the discriminating unit 64 discriminates that the drug is registered as a drug to be discarded in the drug database or when the discriminating unit 64 discriminates that the object accommodated in the first accommodating portion 11 is foreign matter other than the drug, the discriminating unit 64 outputs, as the discrimination result, a fact that the drug is not to be subjected to the sorting.

[Drug Sorting Processing]

Figure 5:
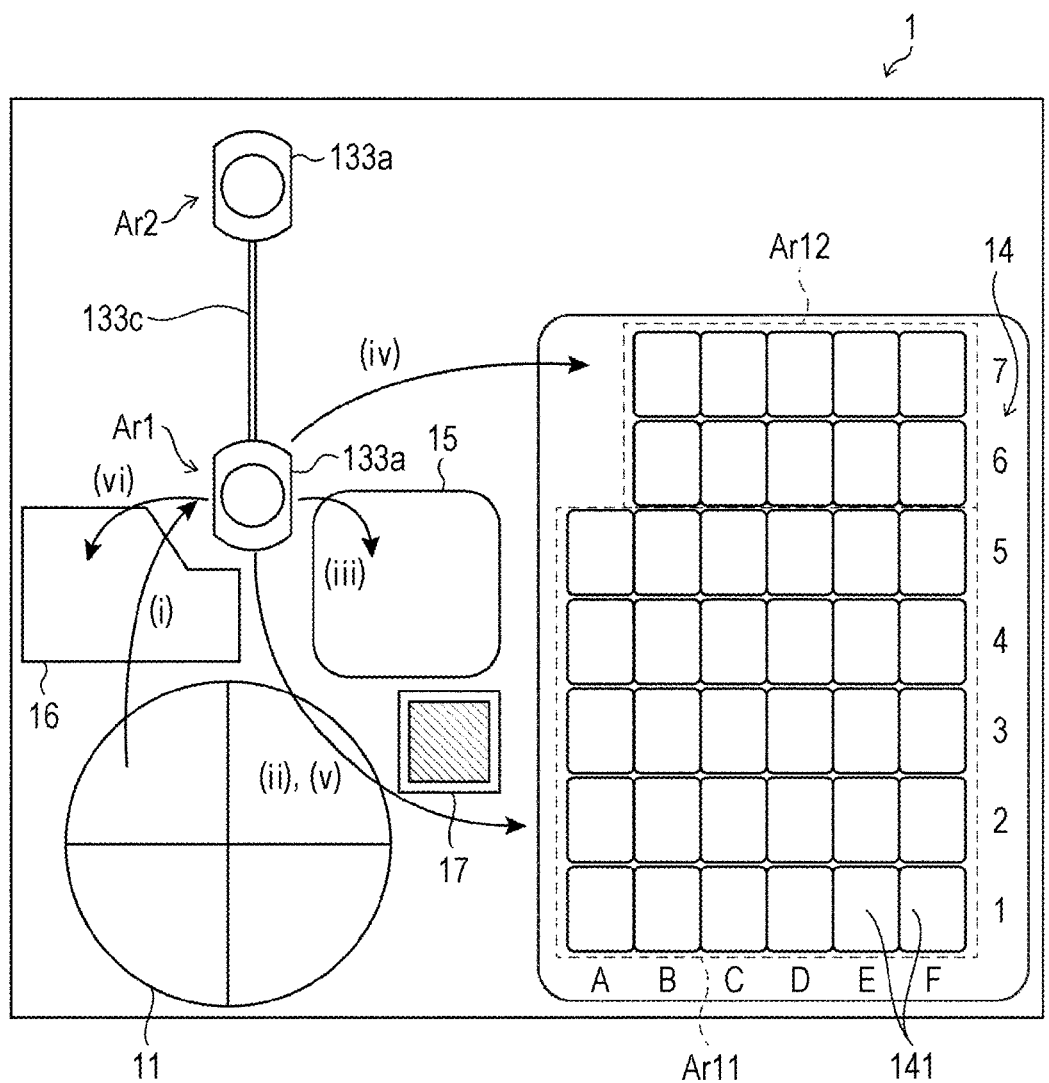
FIG. 5 is a view for illustrating an example of drug sorting processing.
Figure 6:
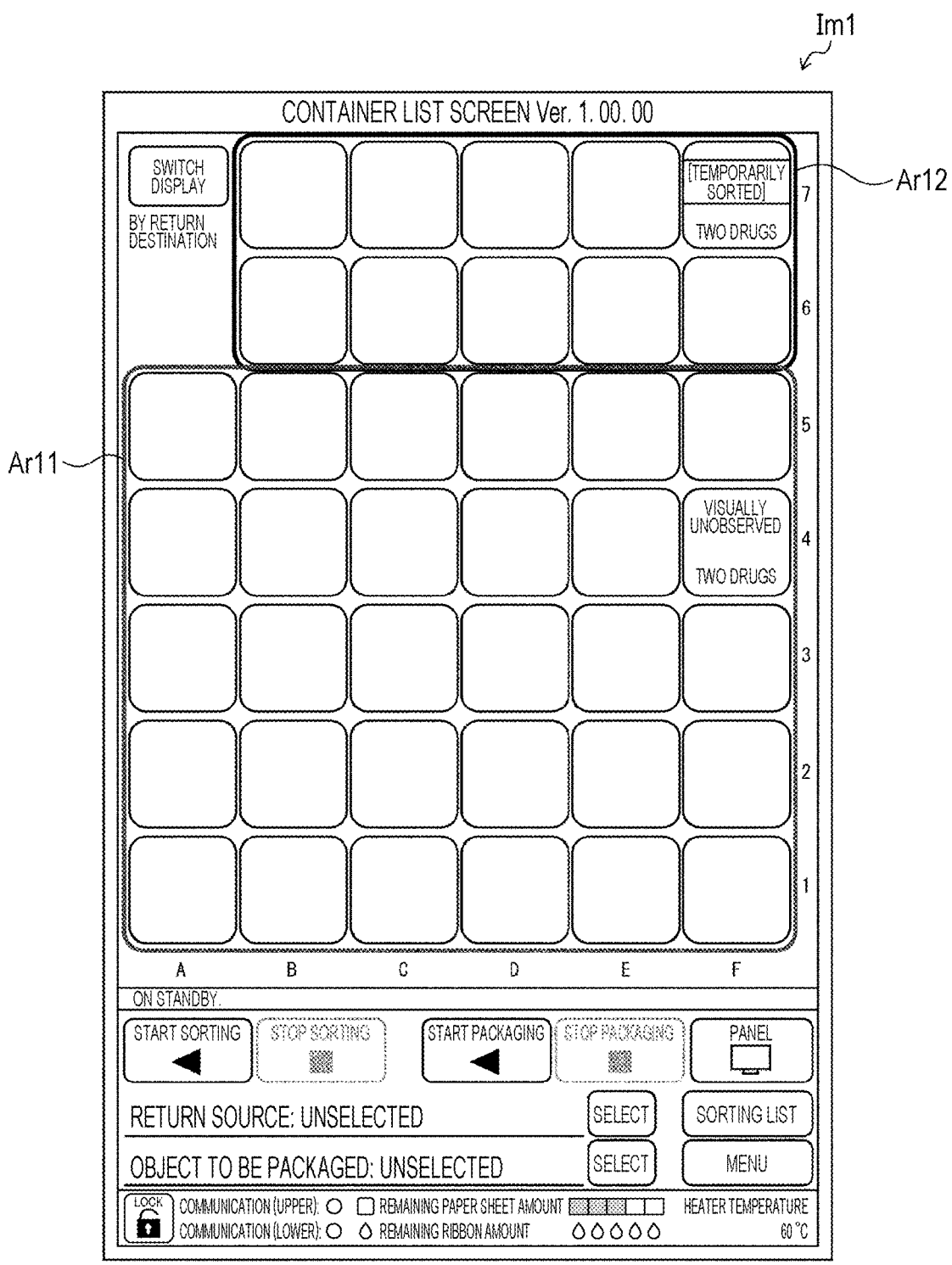
FIG. 6 is a diagram for illustrating a display example of a sorting image.
Figure 7:
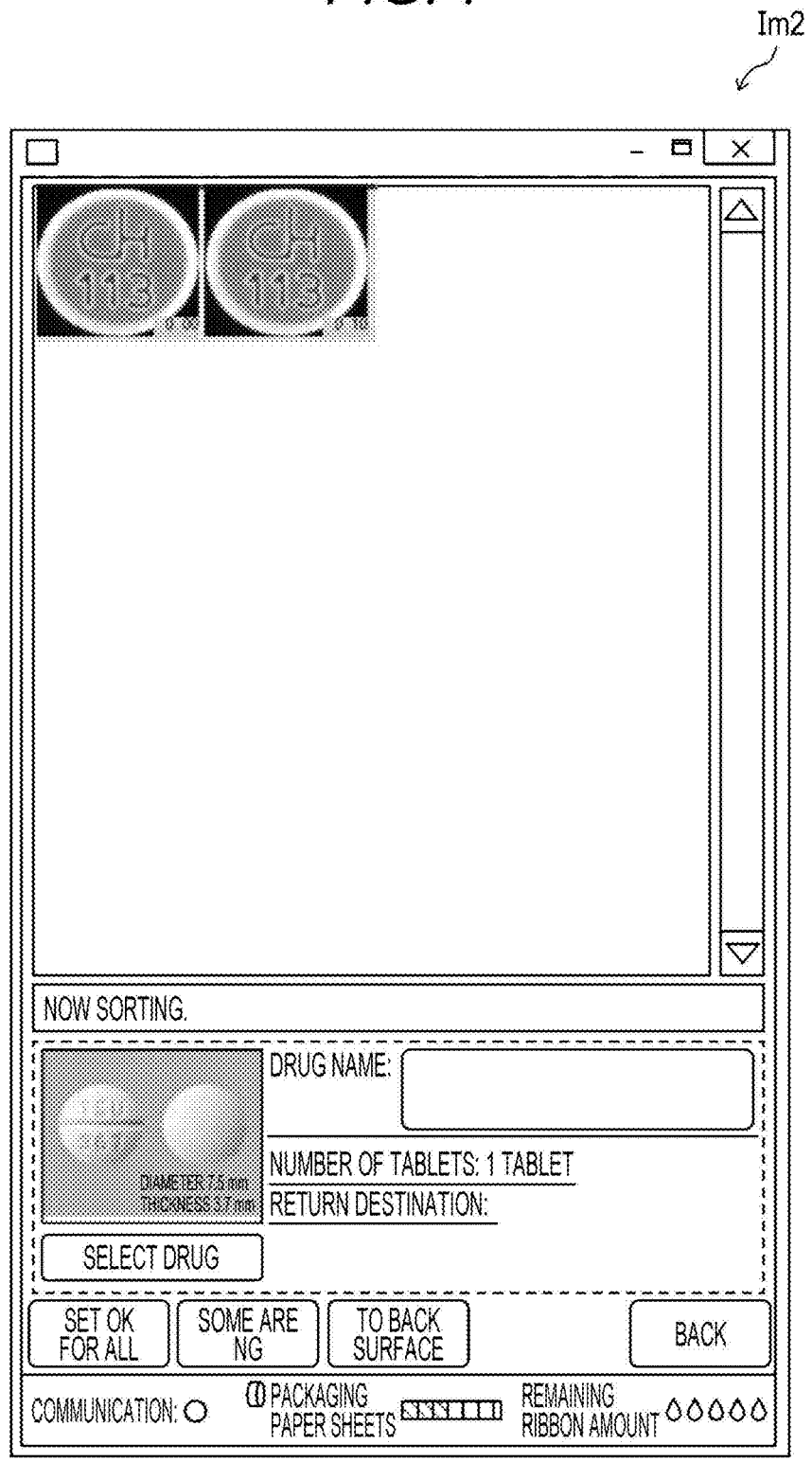
FIG. 7 is a diagram for illustrating a display example of an inspection image.
Figure 8:
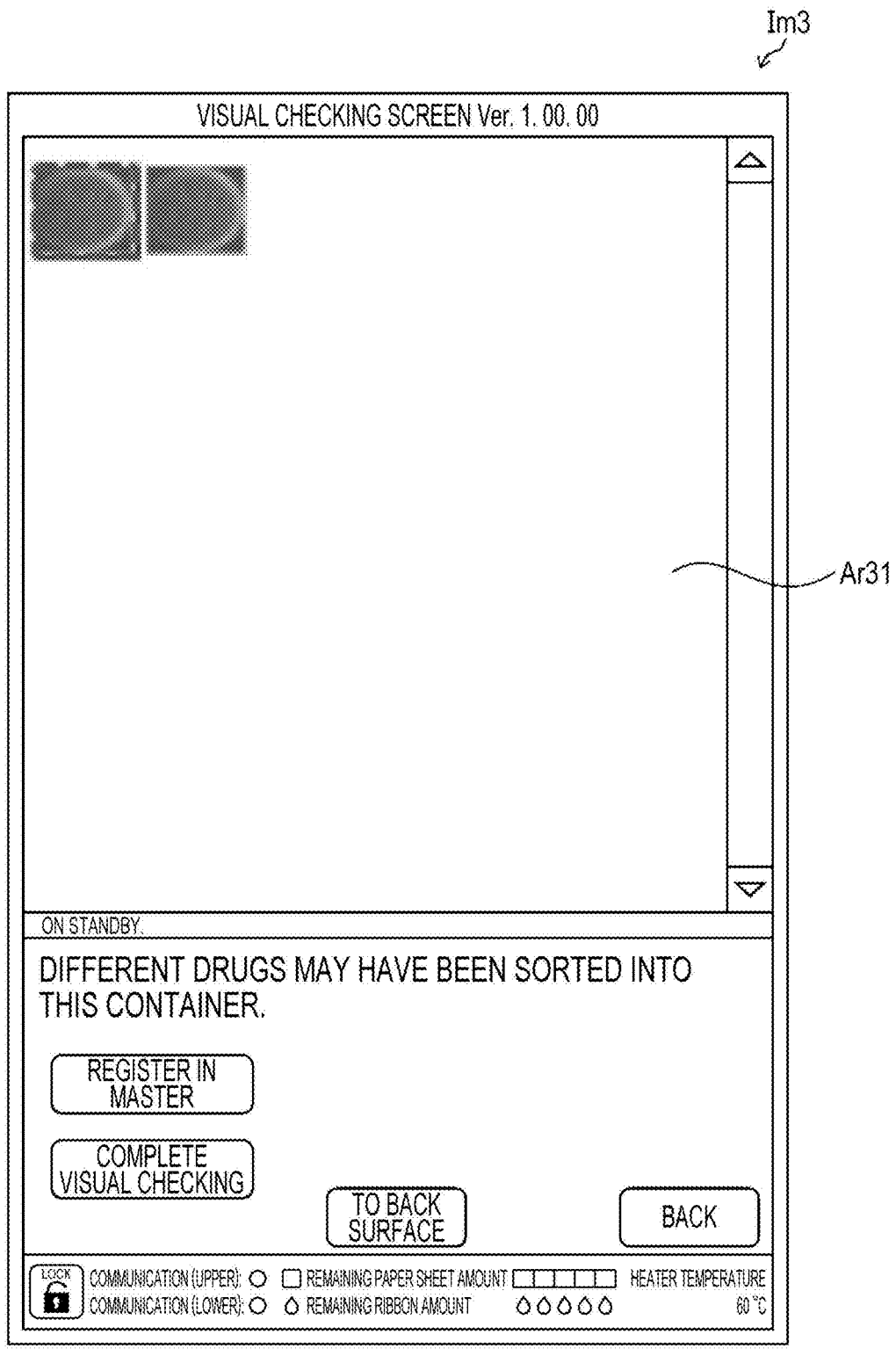
FIG. 8 is a diagram for illustrating a display example of a checking image.

Next, the drug sorting processing based on the result of the above-mentioned discrimination processing is described with reference to FIG. 1 and FIG. 5 to FIG. 8. FIG. 5 is a view for illustrating an example of the drug sorting processing. FIG. 6 is a diagram for illustrating a display example of a sorting image Im1 (sorting screen). FIG. 7 is a diagram for illustrating a display example of an inspection image Im2 (inspection screen). FIG. 8 is a diagram for illustrating a display example of a checking image (checking screen) Im3. The above-mentioned drug sorting processing is mainly performed by the conveying/sorting unit 12 and the sorting control unit 62.

In FIG. 5, for the sake of convenience, reference symbols A to F and reference numerals 1 to 7 for identifying the positions of the sorting cups 141 that can be placed on the second accommodating portion 14 are indicated. In addition, the sorting cups 141 are each a sorting container into which sorted drugs are to be accommodated, and can be removably placed in the second accommodating portion 14.

As described above, a drug accommodated in the first accommodating portion 11 is conveyed from the first accommodating portion 11 to the receiving area Ar1 (see (i) in FIG. 5), and is then moved to the arrangement area Ar2. After having the image picked up by the first camera 131, the drug is moved from the arrangement area Ar2 back to the receiving area Ar1. After that, in this embodiment, the drug is conveyed through a route indicated by (ii), (iii) to (v), or (vi) of FIG. 5 based on the discrimination result obtained by the discriminating unit 64.

Specifically, the conveying/sorting unit 12 stores the drug into the second accommodating portion 14 or into the standby tray 15 for each type based on the discrimination result obtained by the discriminating unit 64 (see (ii) and (iii) of FIG. 5). The sorting control unit 62 controls the conveying/sorting unit 12 to convey the drug arranged in the receiving area Ar1 after the image pick-up and the discrimination processing to a predetermined sorting cup 141 of the second accommodating portion 14 or the standby tray 15 based on the discrimination result.

As illustrated in FIG. 1 and FIG. 5, in this embodiment, a confirmed area Ar11 (first area) and a temporarily determined area Ar12 (second area) are set in the second accommodating portion 14. The confirmed area Ar11 is an area for accommodating a drug determined to have drug data corresponding to the image data by the discriminating unit 64. Meanwhile, the temporarily determined area Ar12 is an area, which is set at a position different from the confirmed area Ar11, for accommodating the drug determined to have no drug data corresponding to the image data by the discriminating unit 64.

In the example of FIG. 5, the confirmed area Ar11 is set in A-1 to F-5 on the drug take-out side, and the temporarily determined area Ar12 is set in B-6 to F-7 at positions apart from the drug take-out side. However, the positions and ranges for setting the confirmed area Ar11 and the temporarily determined area Ar12 are not limited thereto, and can be changed depending on the user's convenience.

As in the example of FIG. 5, when the confirmed area Ar11 is set wider than the temporarily determined area Ar12, the drug sorting device 1 may be referred to as being set to the "confirmed area effective utilization mode" of effectively utilizing the confirmed area Ar11 in the second accommodating portion 14.

The conveying/sorting unit 12 accommodates drugs determined to have drug data corresponding to the image data into the confirmed area Ar11 for each type (see (ii) or (v) of FIG. 5). Meanwhile, the conveying/sorting unit 12 accommodates the drugs determined to have no drug data corresponding to the image data into the temporarily determined area Ar12 (see (iv) of FIG. 5).

(Case of (ii) of FIG. 5)

When the sorting control unit 62 receives the drug data relating to the drug as the discrimination result, the sorting control unit 62 assumes that the discriminating unit 64 has determined that the drug data corresponding to the image data is present, and determines the sorting position (sorting cup 141) for storing this drug in the confirmed area Ar11. The sorting control unit 62 also stores this discrimination result (drug data) and the determined sorting position in the storage unit 80 in connection with each other.

When the sorting control unit 62 determines the sorting position, the sorting control unit 62 controls the conveying mechanism 123 in the same manner as the conveyance control unit 61 to move the conveying/sorting unit 12 to a position above the receiving area Ar1. In the same manner as the conveyance control unit 61, the sorting control unit 62 controls the second camera 121 and the suction/shutter mechanism 122 to suck the drug arranged in the receiving area Ar1. After that, the conveying mechanism 123 conveys the drug to the determined sorting cup 141. After the conveyance, the drug is stored into this sorting cup 141 by canceling the suction. The sorting control unit 62 also counts the number of drugs stored in the sorting cup 141, and stores the number in the storage unit 80 in association with the sorting position.

(Case of (iii) of FIG. 5)

When the sorting control unit 62 receives the discrimination result indicating that the type of the drug is the estimated drug, the sorting control unit 62 assumes that the discriminating unit 64 has determined that no drug data corresponding to the image data is present, and determines the standby tray 15 as the sorting position. Then, the sorting control unit 62 controls the conveying/sorting unit 12 to convey the drug from the receiving area Ar1 to the standby tray 15.

For example, in the above-mentioned "confirmed area effective utilization mode," after the sorting (sorting to the confirmed area Ar11, the standby tray 15, or the collection tray 16) of the drugs accommodated in the first accommodating portion 11 is completed, the drugs accommodated in the standby tray 15 are again subjected to the discrimination processing by the discriminating unit 64. That is, in the above-mentioned "confirmed area effective utilization mode," the drugs whose types have been discriminated are sorted into the confirmed area Ar11, and the estimated drugs are temporarily placed in the standby tray 15. Then, after the drugs whose types have been discriminated are sorted into the confirmed area Ar11, re-sorting is executed on the estimated drugs accommodated in the standby tray 15. Specifically, the sorting control unit 62 controls the conveying/sorting unit 12 to convey the drug from the standby tray 15 to the receiving area Ar1. After that, this drug is moved from the receiving area Ar1 to the arrangement area Ar2, and then the above-mentioned drug image pick-up processing and image processing/discrimination processing are performed on this drug.

As a result, when the discriminating unit 64 determines that the drug data corresponding to the image data is present, the sorting control unit 62 determines the drug-unstored sorting cup 141 (sorting cup 141 whose sorting position is undetermined) in the confirmed area Ar11, as the sorting position. After that, as described above, the sorting control unit 62 controls the conveying/sorting unit 12 to convey the drug from the receiving area Ar1 to the sorting cup 141 in the confirmed area Ar11, which has been determined as the sorting position (see (v) of FIG. 5). The sorting control unit 62 also stores the drug data identified in the drug database and the determined sorting position in the storage unit 80 in association with each other.

Meanwhile, when the discriminating unit 64 again determines that no drug data corresponding to the image data is present, the sorting control unit 62 determines the drug-unstored sorting cup 141 in the temporarily determined area Ar12 as the sorting position. Then, the sorting control unit 62 stores the feature of the drug relating to the estimated drug and the determined sorting position in the storage unit 80 in association with each other.

The sorting control unit 62 determines the sorting position in the temporarily determined area Ar12 based on at least one of the features of the drug (estimated drug) included in the image. For example, the sorting control unit 62 determines the sorting position in the temporarily determined area Ar12 based on at least one of the color and the shape of the estimated drug and the information attached to this drug in the image. Specifically, the sorting control unit 62 determines the sorting position so that the estimated drugs regarded as matching each other in at least one of the color and the shape of the drug and the information attached to this drug have the same sorting position. The information attached to the drug refers to, for example, at least a part of the identification information attached to the drug. When at least parts of the identification information are substantially match (when there is a similar part in two pieces of identification information to be compared), the drugs attached with this piece of identification information may be accommodated into the same sorting cup 141. Meanwhile, the sorting control unit 62 determines the drug-unstored sorting cup 141 in the temporarily determined area Ar12 as the sorting position for the estimated drug to be sorted first into the temporarily determined area Ar12 and for the estimated drug to be sorted having a feature that does not match the feature of the estimated drug that has already been sorted.

After that, the sorting control unit 62 controls the conveying/sorting unit 12 to convey the drug to the sorting cup 141 in the temporarily determined area Ar12, which has been determined as the sorting position (see (iv) of FIG. 5). Specifically, the conveying/sorting unit 12 sorts the estimated drug into each position (each sorting cup 141) in the temporarily determined areas Ar12 based on at least one of the color and the shape of the drug and the information attached to this drug, which are included in the image.

Even in a case where the sorting control unit 62 has received the drug data relating to the drug as the discrimination result, when drugs are stored in all the sorting cups 141 in the confirmed area Ar11, the sorting control unit 62 determines the standby tray 15 as the sorting position. In this case, when there occurs a vacant sorting cup 141 in the confirmed area Ar11, the sorting control unit 62 determines the sorting position of the drugs sorted into the standby tray 15 as a position at which this sorting cup 141 is arranged. Meanwhile, when drugs are stored in all the sorting cups 141 in the temporarily determined area Ar12, the sorting control unit 62 causes the drug to stand by in the standby tray 15 until there occurs a vacant sorting cup 141 in the temporarily determined area Ar12.

As described above, a size of the confirmed area Ar11 can be freely set by the user. For example, as illustrated in FIG. 5, the user may set the size of the confirmed area Ar11 so as to be as large as possible (to the above-mentioned "confirmed area effective utilization mode"). In this case, it is possible to increase a possibility that all or most of the drugs whose types have been discriminated among the drugs accommodated in the first accommodating portion 11 are accommodated into the confirmed area Ar11. However, a configuration that enables the following two settings to be selected in the above-mentioned "confirmed area effective utilization mode" may be employed for the setting of the confirmed area Ar11.

(1) Such a setting of the confirmed area Ar11 as to allow the drug whose type has been discriminated to be accommodated into the standby tray 15. In a case of this setting, when there occurs a vacancy in the confirmed area Ar11, the control unit 60a accommodates the drug temporarily placed in the standby tray 15 into the confirmed area Ar11.

(2) Such a setting of as large a confirmed area Ar11 as possible as to prevent the drug whose type has been discriminated from being sorted into the standby tray 15 as much as possible.

(Alternative Processing in Case of (iii) of FIG. 5)

Unlike the processing in the above-mentioned "confirmed area effective utilization mode," the estimated drug may be directly conveyed to the temporarily determined area Ar12 without being temporarily placed in the standby tray 15. That is, after the discrimination processing for the drugs accommodated in the first accommodating portion 11 has been completed, the control unit 60a may sequentially sort the drugs into any one of the confirmed area Ar11 and the temporarily determined area Ar12 depending on the discrimination result.

In this case, when the control unit 60a cannot discriminate a class of the drug, the control unit 60a may execute the discrimination processing again. This is because there is a possibility that the type of the drug can be discriminated by the discrimination processing executed again. As the discrimination processing executed again, the discrimination processing is executed, for example, a predetermined number of times. The predetermined number of times is only required to be set to the number of times (for example, three times) in which there is a possibility that the type of the drug can be discriminated by the discrimination processing executed again and an influence on an increase in the processing time period is small. When the type of the drug is successfully discriminated by the discrimination processing executed again, the control unit 60a conveys this drug to the confirmed area Ar11. Meanwhile, when the type of the drug fails to be discriminated even after the discrimination processing has been performed a predetermined number of times, this drug is conveyed to the temporarily determined area Ar12.

As a result of sequentially sorting, when the sorting into the confirmed area Ar11 becomes impossible (when there are no more vacant sorting cups 141 in the confirmed area Ar11), the drugs to be sorted are accommodated into the standby tray 15. Meanwhile, when the sorting into the temporarily determined area Ar12 becomes impossible (when there are no more vacant sorting cups 141 in the temporarily determined area Ar12), the estimated drug to be sorted is accommodated into the standby tray 15. That is, when there are no more sorting positions in each of the confirmed area Ar11 and the temporarily determined area Ar12, the drug to be sorted or the estimated drug is conveyed to and accumulated in the standby tray 15 without being accommodated into the other area.

Note that, the drug sorting device 1 may be set to any one of the "confirmed area effective utilization mode" and a "confirmed area non-effective utilization mode." When the drug sorting device 1 is set to the "confirmed area effective utilization mode," as described above, the estimated drug is temporarily placed in the standby tray 15, and is then sorted into the confirmed area Ar11 or the temporarily determined area Ar12. Meanwhile, when the drug sorting device 1 is set to the "determined area non-effective utilization mode," as described above, the estimated drug is directly sorted into the temporarily determined area Ar12 without being temporarily placed in the standby tray 15.

(Case of (vi) of FIG. 5)

When the sorting control unit 62 receives a discrimination result indicating that the drug is not to be subjected to the sorting, the drug subjected to the discrimination is a drug registered as a drug to be discarded in the drug database, or an object arranged in the receiving area Ar1 after the discrimination is foreign matter. Therefore, the sorting control unit 62 controls the conveying/sorting unit 12 to convey this drug or the foreign matter to the collection tray 16.

In this manner, the sorting control unit 62 stores all the objects accommodated in the first accommodating portion 11 into any one of the second accommodating portion 14, the standby tray 15, and the collection tray 16 irrespective of the discrimination result of the type of the drug. Therefore, even when the type of the drug cannot be identified as one type or even when foreign matter is mixed into the first accommodating portion 11, the sorting processing can be continued without stopping for that reason.

When the drug being a discrimination target is a drug registered in the drug database, the drug can be sorted into the confirmed area Ar11, and when the drug is not registered therein, the drug can be sorted into the temporarily determined area Ar12. Therefore, a drug can be sorted irrespective of whether or not its drug data has been registered in the storage unit 80. In addition, the sorting area can be changed depending on whether or not the drug data has been registered in the storage unit 80, and hence it is possible to improve convenience of drug registration processing described later.

(Other Configuration)

In order to take out the drug for which the discrimination processing has been completed from the drug loading stage 133a arranged in the receiving area Ar1, the sorting control unit 62 causes the second camera 121 to pick up an image of this drug loading stage 133a, and narrows down the position of this drug. In addition, when the drug stored in the sorting cup 141 is to be conveyed to the packaging mechanism 6, in order to take out the drug from this sorting cup 141, the sorting control unit 62 causes the second camera 121 to pick up an image of this sorting cup 141, and narrows down the drugs to be conveyed.

In the confirmed area Ar11, the drug data relating to the drug stored in the sorting cup 141 by the sorting control unit 62 is stored into the RFID tag provided on this sorting cup 141 by the second RFID reader/writer unit 18.

In the same manner as the first RFID reader/writer unit 5, the second RFID reader/writer unit 18 writes drug data or other such data to the RFID tag, or reads drug data or other such data stored in the RFID tag. The sorting control unit 62 causes the RFID control unit 68 to write data relating to this drug each time the drug is stored into the sorting cup 141.

The second RFID reader/writer unit 18 is provided under the second accommodating portion 14. Specifically, the second RFID reader/writer unit 18 is provided so as to be opposed to the bottom portion of each sorting cup 141 at a time of reading or writing data relating to the drug stored in the RFID tag for each sorting cup 141.

Display Image Example

During the drug sorting processing or while an operation for the drug sorting processing is stopped, the display control unit 67 can display the sorting image Im1 illustrated in FIG. 6 on the display unit 32.

Each of a plurality of sorting positions in which drugs are sorted, the sorting cup 141 arranged at this sorting position, and the drug data (or data including at least a part of the target feature) relating to drugs accommodated in the sorting cup 141 are stored in the storage unit 80 in association with one another. In addition, the number of drugs accommodated in the sorting cup 141 and the image data on the accommodated drugs are also stored in the storage unit 80 in association therewith.

Therefore, the display control unit 67 can display the sorting image Im1 that reflects the plurality of sorting positions in the second accommodating portion 14 and a sorting status (for example, the number of drugs accommodated therein) at each of the sorting positions.

The display control unit 67 also displays, for example, an inspection result at the position in which the drug has been sorted in the sorting image Im1. As the inspection result, the display control unit 67 displays "visually unobserved" indicating that an inspection has not been performed through visual observation or "visually observed" indicating that the inspection has been completed. In addition, the display control unit 67 displays "temporarily sorted" indicating the fact of being sorted into the temporarily determined area Ar12 due to the unregistered drug data. Those indications allow the user to recognize the sorting cup 141 in which the drug for which an inspection has not been performed has been sorted or the sorting cup 141 in which the drug required to be registered in the drug database has been sorted.

When the display control unit 67 receives a user input for the sorting position in the confirmed area Ar11 illustrated in the sorting image Im1, the display control unit 67 displays, on the display unit 32, the inspection image Im2 (see FIG. 7) of the drug associated with this sorting position. Thus, it is possible to display the inspection image Im2 of the drug for which the user wishes to perform the visual inspection.

In addition, when the display control unit 67 receives a user input for the sorting position in the temporarily determined area Ar12 illustrated in the sorting image Im1, the display control unit 67 displays, on the display unit 32, the checking image Im3 of the drug associated with this sorting position. Thus, it is possible to display the checking image Im3 (see FIG. 8) of the drug wished to be registered in the drug database by the user.

[Drug Registration Processing]

Figure 9C:
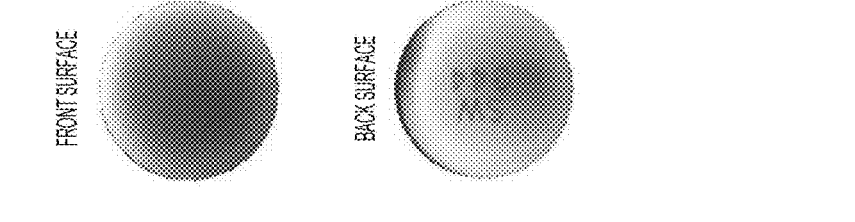
FIG. 9C is a diagram for illustrating an example of images picked up by a first camera.
Figure 9B:
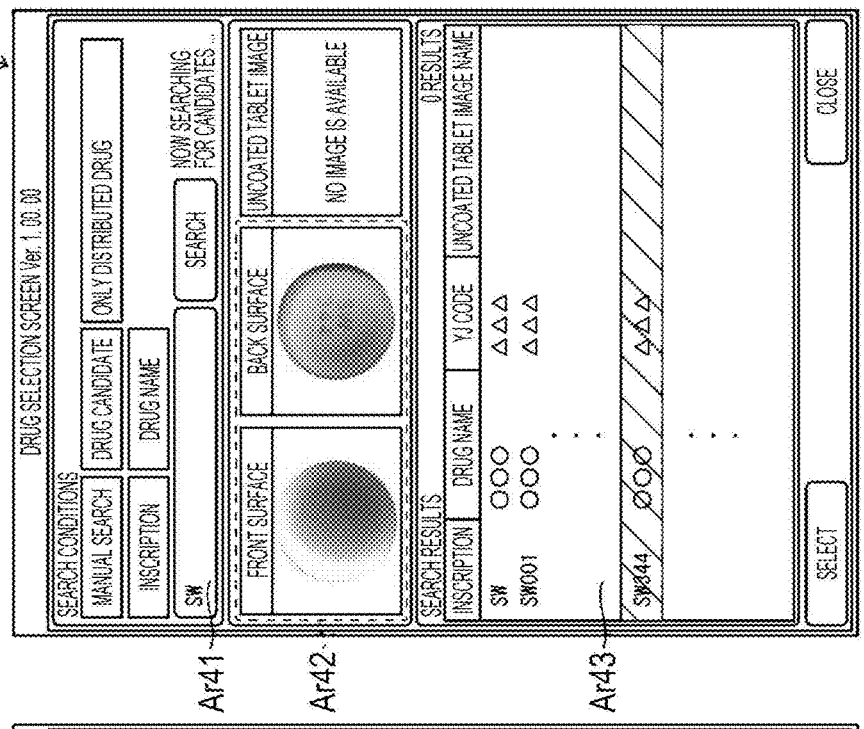
FIG. 9A and FIG. 9B are diagrams for illustrating a display example of a search image.
Figure 9A:
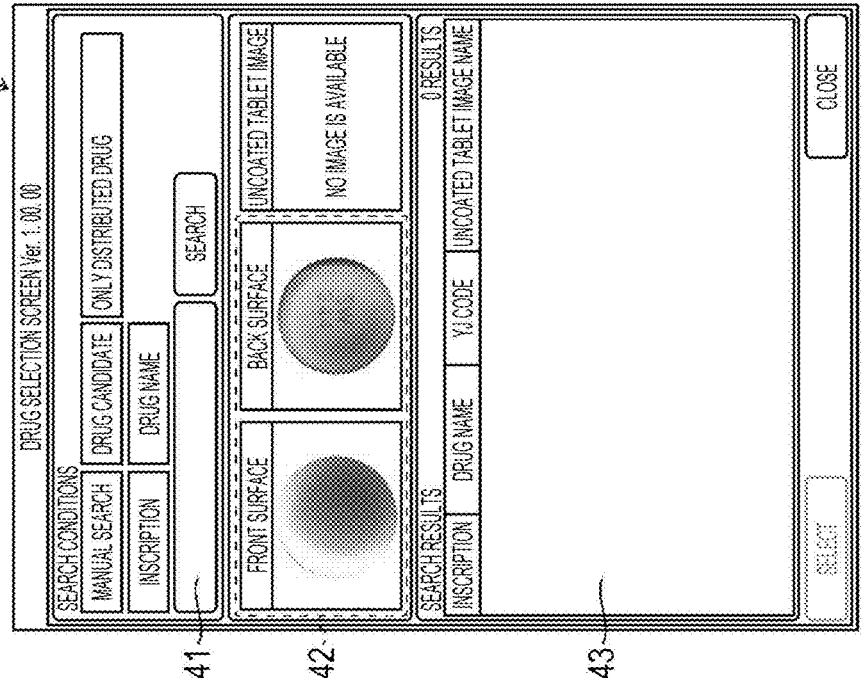
Figure 10A:
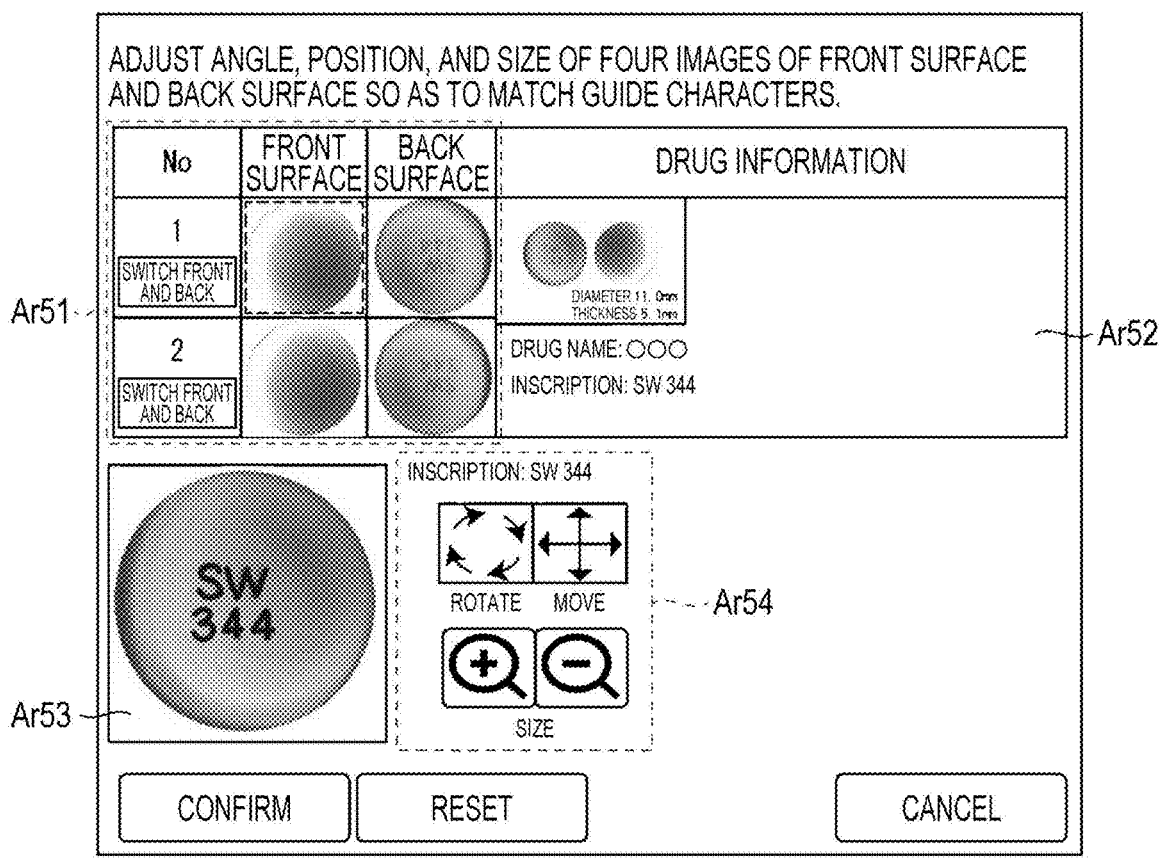
FIG. 10A is a diagram for illustrating an example of a registration image.
Figure 10B:
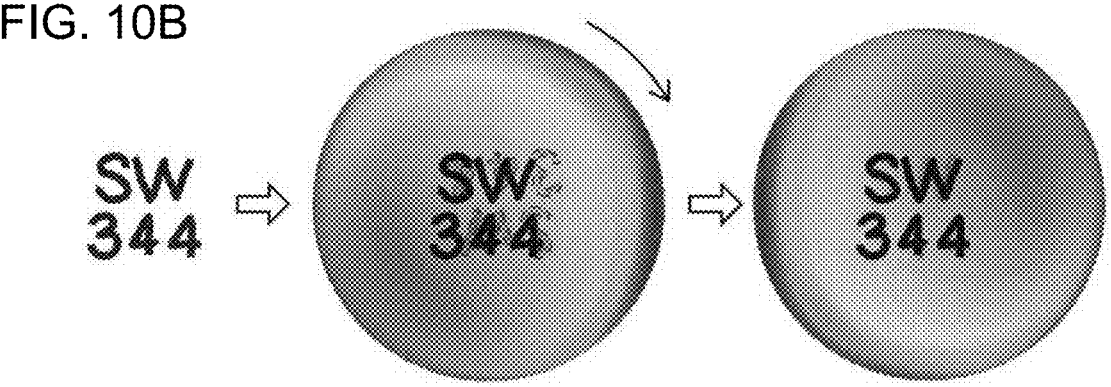
FIG. 10B is a diagram for illustrating an example of image adjustment processing.

Next, the drug registration processing for registering the drug sorted into the temporarily determined area Ar12 in the drug database is described with reference to FIG. 1, FIG. 6, and FIG. 8 to FIGS. 10A and 10B. FIG. 9A and FIG. 9B are diagrams for illustrating a display example of a search image (search screen) Im4, and FIG. 9C is a diagram for illustrating an example of images picked up by the first camera 131. FIG. 10A is a diagram for illustrating an example of a registration image (registration screen) Im5, and FIG. 10B is a diagram for illustrating an example of image adjustment processing.

As described above, the display control unit 67 displays the checking image Im3 illustrated in FIG. 8 by receiving the user input for the sorting position of the temporarily determined area Ar12 illustrated in the sorting image Im1 illustrated in FIG. 6. As illustrated in FIG. 8, the checking image Im3 includes at least an image display area Ar31 and a "register in master" button.

The image display area Ar31 is an area for displaying images (images picked up by the first camera 131) represented by the image data on the drugs stored in the sorting cup 141, which are stored in the storage unit 80 in association with the sorting position, the number of the images being the number of drugs stored in the sorting cup 141. In this example, in the image display area Ar31, the images of two drugs stored in the sorting cup 141 arranged at the position of F-7 are displayed. The "register in master" button is used for receiving a user input for starting to register the drug selected in the image display area Ar31 in the drug database.

When the control unit 60a receives a user input with respect to the "register in master" button with one piece of image data being selected, the control unit 60a performs registration processing on the drug corresponding to this one piece of image data. Specifically, as illustrated in FIG. 1, the control unit 60a includes the registration unit 70. The registration unit 70 is configured to collectively perform the processing for registering, in the drug database, the drug data relating to the drugs sorted into the temporarily determined area Ar12. That is, the registration unit 70 registers the drug data on the drug relating to the image data identified by the user, in association with this image data, for the drugs determined to have no drug data corresponding to the image data by the discriminating unit 64.

Specifically, the registration unit 70 controls the display control unit 67 to display the search image Im4 illustrated in FIG. 9A on the display unit 32. The search image Im4 is an image for showing search results for the drug stored in the sorting cup 141.

As illustrated in FIG. 9A, the search image Im4 includes at least a character input area Ar41, an image display area Ar42, a search result list area Ar43, and a "select" button. The character input area Ar41 is an area in which characters for performing a search for the drug displayed in the image display area Ar42 can be input. The image display area Ar42 is an area for displaying the image picked up by the first camera 131 (the same image as the image selected in FIG. 8). The search result list area Ar43 is an area for displaying the search results when a user input with respect to a "search" button is received. The "select" button is used for determining the selection of one piece of drug data among pieces of drug data displayed in the search result list area Ar43.

In this case, the first camera 131 picks up an image of the drug placed on the drug loading stage 133a arranged in the arrangement area Ar2. Therefore, an orientation of the information (for example, inscribed information or print information) attached to the drug in the image data stored in the storage unit 80 differs depending on the drug. In the image display area Ar42, the image (image picked up by the first camera 131) represented by the image data stored in the storage unit 80 is displayed as it is. Therefore, in the image display area Ar42, for example, as illustrated in FIG. 9A, an image in which the inscribed information is oriented downward is displayed. In another case, when an image of the inscribed information is picked up in a lateral orientation, as illustrated in FIG. 9C, an image in which the inscribed information is oriented laterally is displayed in the image display area Ar42. The same applies to the inspection image Im2 illustrated in FIG. 7 and the checking image Im3 illustrated in FIG. 8.

When the display control unit 67 displays the search image Im4 illustrated in FIG. 9A, the user recognizes the inscribed information by viewing the image displayed in the image display area Ar42. The user inputs at least a part of the recognized inscribed information to the character input area Ar41.

When the registration unit 70 receives the user input with respect to the "search" button after at least a part of the inscribed information is input to the character input area Ar41, the registration unit 70 searches a comprehensive drug database based on characters input to the character input area Ar41.

The comprehensive drug database is provided for managing drug data relating to a plurality of types of drugs. The comprehensive drug database is a database connectable to the drug sorting device 1 so as to enable communication to/from the drug sorting device 1, which is managed by a data management device 500 (see FIG. 13) configured to comprehensively and centrally manage a plurality of types of drugs. The data management device 500 is, for example, a device to be used by the manufacturer of the drug sorting device 1. The comprehensive drug database includes drug data relating to all drugs that can be handled by the drug sorting device 1 used in various places (hospital, ward, pharmacy, or another such place) and by a device other than the drug sorting device 1 (for example, packaging machine).

Meanwhile, the drug database is a database managed by the drug sorting device 1 or in the hospital, the ward, the pharmacy, or another such place in which the drug sorting device 1 is used. As described above, the drug database is managed by, for example, the storage unit 80. The number of pieces of drug data managed in the comprehensive drug database is enormous, and hence it is not realistic to include all of those pieces of drug data in the drug database. Therefore, the drug database is managed by extracting pieces of drug data that are expected to be used by each drug sorting device 1 or in each hospital, ward, pharmacy, or another such place from among the pieces of drug data included in the comprehensive drug database. That is, even drug data that is not present in the drug database is present in the comprehensive drug database. Therefore, the registration unit 70 searches the comprehensive drug database.

The drug data registered in the comprehensive drug database and the drug database include image data on a drug in which the identification information (for example, inscribed information or printed information) attached to the drug has been adjusted so as to have a defined orientation and a defined size. The orientation and the size are, for example, set for each type or each size of the drug.

It is assumed that the user has pressed the "search" button after "SW" within information included in the image is input to the character input area Ar41. In this case, as illustrated in FIG. 9B, the registration unit 70 displays, in the search result list area Ar43, the results of searching the comprehensive drug database for the characters "SW." In the search result list area Ar43, the user selects drug data that matches information "SW344" included in the image.

When the registration unit 70 receives the user input with respect to the "select" button with one piece of drug data displayed in the search result list area Ar43 being selected, the registration unit 70 controls the display control unit 67 to display the registration image Im5 on the display unit 32. At this time, the registration unit 70 extracts the inscribed information from the image picked up by the first camera (the same image as the image selected in FIG. 8) by controlling the discriminating unit 64 (feature extraction unit 64a). When a division line is included in this image, the registration unit 70 extracts the division line as well. A known technology can be adopted for extraction of the inscribed information.

As illustrated in FIGS. 10A and 10B, the registration image Im5 includes at least an image display area Ar51, a drug information display area Ar52, an image adjustment area Ar53, an operation unit display area Ar54, and a "confirm" button.

The image display area Ar51 is an area for displaying the image picked up by the first camera 131. In the image display area Ar51, the same image as the image selected in FIG. 8 is displayed. However, in the image display area Ar51, images of one drug picked up from a plurality of directions may be displayed. In FIGS. 10A and 10B, four images of one drug picked up from different directions are displayed.

The drug information display area Ar52 is an area for displaying drug data (for example, image data, drug name, and inscribed information (for example, identification code)) relating to the drug extracted from the comprehensive drug database. The image adjustment area Ar53 is an area for adjusting the orientation or the size of the image. The operation unit display area Ar54 is an area for displaying an operation unit for adjusting the orientation or the size of the image displayed in the image adjustment area Ar53. The "confirm" button is used for confirming the registration in the drug database.

When one of the images displayed in the image display area Ar51 is selected, the registration unit 70 displays this image in the image adjustment area Ar53. The registration unit 70 also displays, in the image adjustment area Ar53, the inscribed information extracted at a time of receiving the user input with respect to the "select" button of the search image Im4. That is, the registration unit 70 superimposes and displays the extracted inscribed information and the selected image on the image adjustment area Ar53.

The registration unit 70 displays the extracted inscribed information in the image adjustment area Ar53. The registration unit 70 displays this inscribed information in the image adjustment area Ar53 with the orientation and the size of the extracted inscribed information being adjusted to the orientation and the size that are defined in the drug database. Therefore, the orientation and the size of the selected image are changed depending on the inscribed information displayed in the image adjustment area Ar53, to thereby be able to register, in the drug database, the image data including the inscribed information having the orientation and the size that are defined in the drug database.

In the image adjustment area Ar53, the user operates the operation unit displayed in the operation unit display area Ar54 under a state in which the extracted inscribed information and the selected image are superimposed. Thus, the user rotates the selected image, moves the image in an up-down or left-right direction, and changes the size of this image. The registration unit 70 successively displays, in the image adjustment area Ar53, the image that reflects the user input with respect to this operation unit. This allows the user to change the orientation, the size, and the position of the selected image so as to substantially match those with the orientation and the size of the extracted inscribed information while viewing the image adjustment area Ar53.

For example, in a case of FIG. 10A, as illustrated in FIG. 10B, the registration unit 70 displays the extracted inscribed information in the image adjustment area Ar53, and then displays the selected image in the image adjustment area Ar53. In this example, the inscribed information is oriented downward in the image picked up by the first camera 131. That is, in the image adjustment area Ar53, the extracted inscribed information and the inscribed information in the selected image are oriented in opposite directions. In FIG. 10B, each character of the extracted inscribed information "SW344" is indicated in bold, and each character of the inscribed information "SW344" in the selected image is indicated by the dotted line so as to be clearly distinguishable.

Under this state, the user operates the operation unit displayed in the operation unit display area Ar54 to change the orientation, the size, and the position of the selected image, to thereby substantially match the inscribed information included in the selected image with the orientation and the size of the extracted inscribed information. The user presses the "confirm" button under the state in which the orientations and sizes of those pieces of inscribed information substantially match.

When the registration unit 70 receives the user input with respect to the "confirm" button, the registration unit 70 registers the image data (adjusted image data) representing the image adjusted in the image adjustment area Ar53 and the drug data selected as a result of the search, in the drug database in association with each other.

In this manner, in this embodiment, the discriminating unit 64 (feature extraction unit 64a) extracts the inscribed information (identification information) indicated on the drug included in the image picked up by the first camera 131. The display control unit 67 displays the picked-up image and the extracted inscribed information on the display unit 32. Specifically, the image and the inscribed information are displayed in the image adjustment area Ar53 of the registration image Im5. Then, the registration unit 70 registers the image data representing an image obtained when the inscribed information indicated on the drug included in the image is matched with a predetermined orientation (predetermined orientation defined in the drug database) in which the extracted inscribed information is displayed on the display unit 32.

Thus, the image data including the inscribed information having the orientation and the size that are defined in the drug database can be registered in the drug database. Therefore, accuracy of comparison using the drug database performed by the discriminating unit 64 can be improved, and speed of the comparison can be increased.

As illustrated in FIG. 10A, when a plurality of images are displayed in the image display area Ar51, the registration unit 70 may perform the above-mentioned drug registration processing for each image. In this case, a plurality of pieces of image data are registered in the drug database for one drug. In another case, the registration unit 70 may register the adjusted image data in the drug database only for one image (for example, image determined by the user that the inscribed information is clearly displayed) selected from the plurality of images.

[Drug Registration Processing in Case of Capsule]

Figure 11:
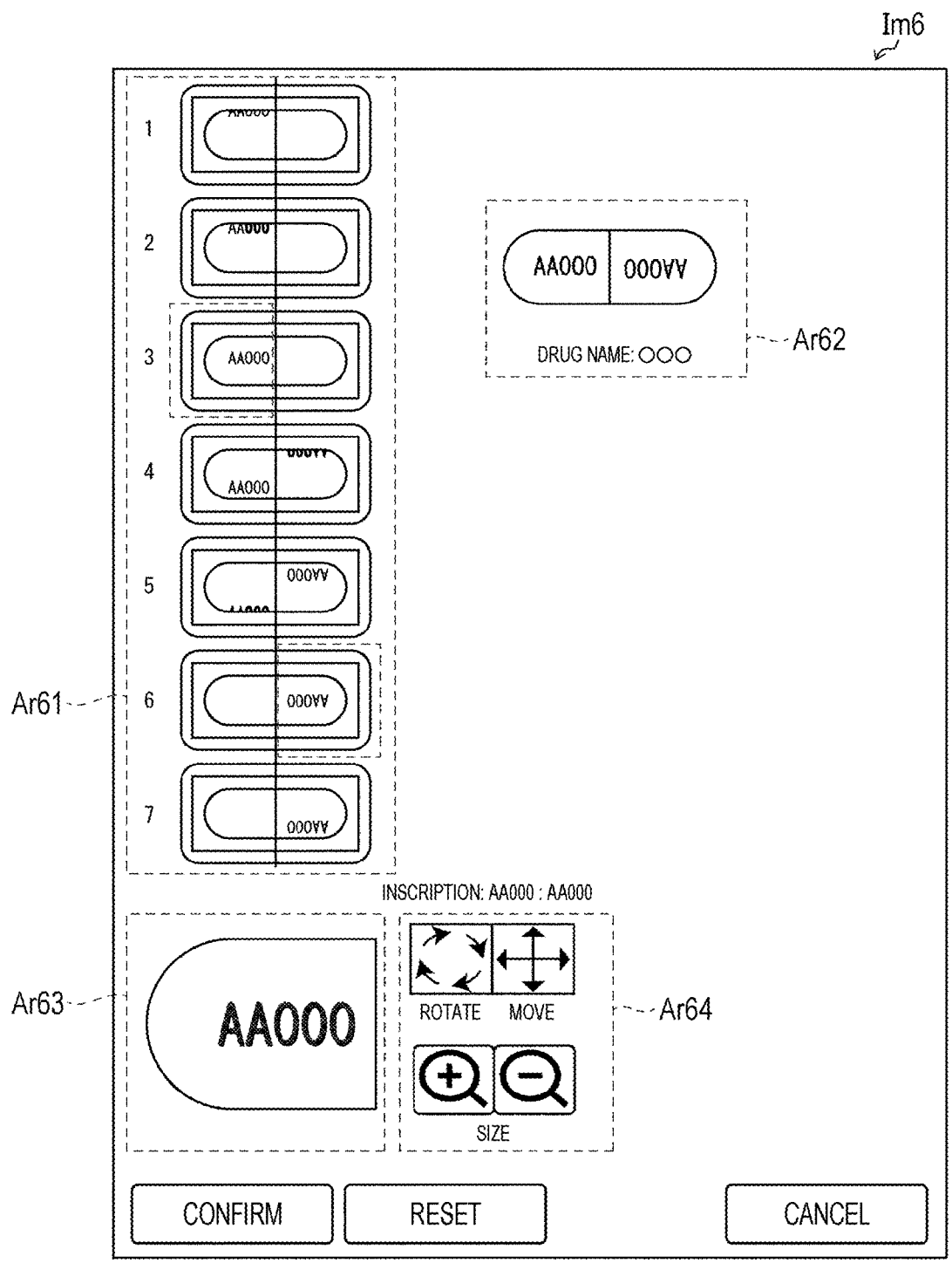
FIG. 11 is a diagram for illustrating an example of the registration image displayed when a capsule is being registered.
Figure 12:
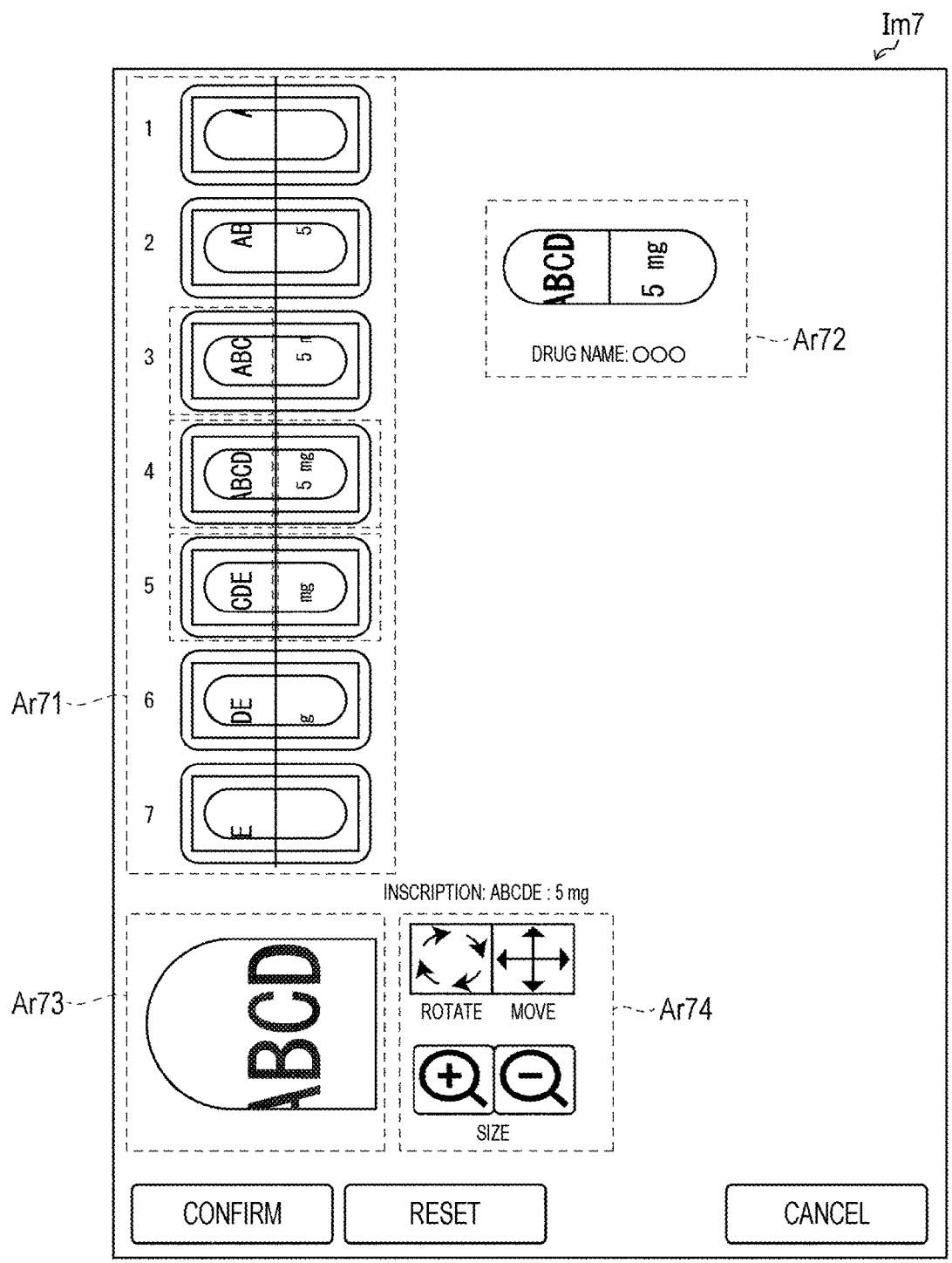
FIG. 12 is a diagram for illustrating an example of the registration image displayed when another capsule is being registered.

Next, the drug registration processing performed when the drug is a capsule is described with reference to FIG. 11 and FIG. 12. FIG. 11 is a diagram for illustrating an example of a registration image Im6 displayed when a capsule is registered. FIG. 12 is a diagram for illustrating an example of a registration image Im7 displayed when another capsule is registered.

When the drug is a capsule, the registration unit 70 controls the display control unit 67 to display, on the display unit 32, a plurality of images picked up from a plurality of positions around the capsule.

In a case of a capsule, unlike a tablet, printed information (for example, identification code) is not always indicated on any one of its front surface and its back surface. In view of this, the registration unit 70 causes a plurality of images to be displayed, to thereby be able to allow the user to select an image that clearly includes printed information from the plurality of images as an image to be registered. Therefore, even in the case of a capsule, it is possible to register image data suitable for registration in the drug database.

As illustrated in FIG. 11, the registration image Im6 includes at least an image display area Ar61, a drug information display area Ar62, an image adjustment area Ar63, an operation unit display area Ar64, and a "confirm" button. Each of the respective areas and the "confirm" button has the same functions as those of the image display area Ar51, the drug information display area Ar52, the image adjustment area Ar53, the operation unit display area Ar54, and the "confirm" button, which are illustrated in FIG. 10A. However, in the image display area Ar61, a plurality of images (in this example, seven images) picked up from a plurality of positions around the capsule are displayed.

In the example of FIG. 11, printed information is attached to each of areas obtained by dividing the capsule into two. In the above-mentioned seven images, the user selects images in each of which printed information is displayed in a central vicinity of each of the areas obtained through the division into two. That is, for each area, the user selects an image including printed information as similar as possible to the printed information included in the image data displayed in the drug information display area Ar62. In this example, the user selects a third image and a sixth image. After that, the same drug registration processing as in the case described with reference to FIGS. 10A and 10B is performed.

That is, in the image adjustment area Ar63, the user changes the orientation, the size, and the position of an image so that the print information within the image selected in the image display area Ar61 substantially matches the print information extracted from the image of the drug whose image has been picked up and displayed so as to be oriented in a predetermined direction. After that, the user presses the "confirm" button under a state in which the print information within the selected image and the extracted print information substantially match. When the registration unit 70 receives the user input with respect to the "confirm" button, the registration unit 70 registers the adjusted image data in the drug database in association with the drug data selected as a result of the search. In this example, the drug registration processing is performed for each of the third image and the sixth image.

In the image data registered in the drug database, the print information in one area is oriented upward and the print information in the other area is oriented downward as illustrated in the drug information display area Ar62. In view of this, the registration unit 70 displays the printed information in the image adjustment area Ar63 so as to be oriented upward with respect to the print information in one area and oriented downward with respect to the print information in the other area. Therefore, the user changes the orientation, the size, and the position of each image so that the print information within the third image substantially matches the print information oriented upward and that the print information within the sixth image substantially matches the print information oriented downward.

There is also a case in which printed information is included in a short-side direction of a capsule. In this case, in the same manner as in FIG. 11, the registration unit 70 causes the display unit 32 to display images picked up from a plurality of directions.

As illustrated in FIG. 12, the registration image Im6 includes at least an image display area Ar71, a drug information display area Ar72, an image adjustment area Ar73, an operation unit display area Ar74, and a "confirm" button. Each of the respective areas and the "confirm" button has the same functions as those of the image display area Ar61, the drug information display area Ar62, the image adjustment area Ar63, the operation unit display area Ar64, and the "confirm" button, which are illustrated in FIG. 11.

The user selects images each including a larger part of printed information in each of the areas obtained through division into two, in seven images included in the image display area Ar71. That is, for each area, the user selects an image including printed information as similar as possible to the printed information included in the image data displayed in the drug information display area Ar72.

In this example, the user selects a third image, a fourth image, and a fifth image for one area and a fourth image and a fifth image for the other area. Then, as in the case described with reference to FIG. 11, the third image, the fourth image, and the fifth image are adjusted for one area, and the fourth image and the fifth image are adjusted for the other area. The user presses the "confirm" button for the adjusted image data having the highest matching degree between the extracted printed information and the printed information included in the selected image. Thus, the registration unit 70 registers the above-mentioned adjusted image data having the highest matching degree, in the drug database in association with the drug data selected as a result of the search.

In this manner, even when the drug is a capsule, the image data including the printed information having the orientation and the size that are defined in the drug database can be registered in the drug database.

The user is not required to select all the images including larger parts of printed information. For example, it suffices that the user selects only one image including printed information as similar as possible to the printed information included in the image data displayed in the drug information display area Ar72 for each area.

In the image data registered in the drug database, as illustrated in the drug information display area Ar72, the printed information in one area which is "ABCD(E)" and the print information in the other area which is "5 mg" are both oriented leftward. In view of this, when the registration unit 70 displays the printed information in both the areas, the registration unit 70 displays, in the image adjustment area Ar73, the printed information oriented leftward.

[Data Management System]

Figure 13:
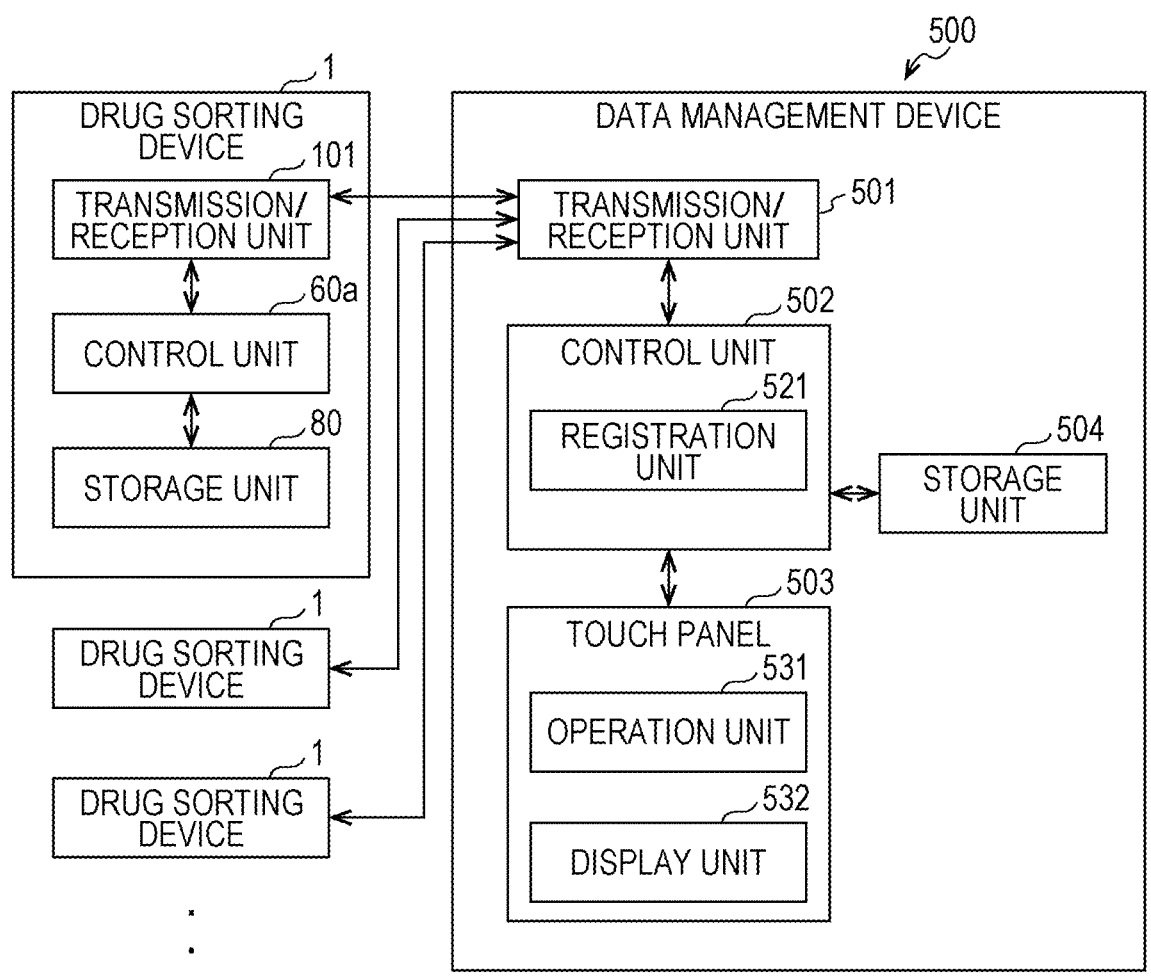
FIG. 13 is a diagram for illustrating an example of a data management system.

Next, a data management system is described with reference to FIG. 13. FIG. 13 is a diagram for illustrating an example of the data management system.

The data management system includes a plurality of drug sorting devices 1 and the data management device 500 that can be connected to each of the drug sorting devices 1 so as to enable communication to/from each of the drug sorting devices 1. The drug sorting device 1 and the data management device 500 transmit and receive data to/from each other through an Internet line or a dedicated virtual private network (VPN) line. The number of drug sorting devices 1 included in the data management system may be one.

In addition to the control unit 60a and the storage unit 80 illustrated in FIG. 1, the drug sorting device 1 includes a transmission/reception unit 101 configured to transmit and receive data to/from the data management device 500. The transmission/reception unit 101 transmits, for example, the image data on the drug sorted into the temporarily determined area Ar12 to the data management device 500.

The data management device 500 includes a transmission/reception unit 501, a control unit 502, a touch panel 503, and a storage unit 504. The transmission/reception unit 501 is configured to transmit/receive data to/from the drug sorting device 1. For example, the transmission/reception unit 501 receives the image data from the transmission/reception unit 101. The control unit 502 is configured to centrally control the data management device 500, and mainly includes a registration unit 521. The registration unit 521 has the same function as that of the registration unit 70 illustrated in FIG. 1. The touch panel 503 includes an operation unit 531 and a display unit 532. The touch panel 503, the operation unit 531, and the display unit 532 have the same functions as those of the touch panel 3, the operation unit 31, and the display unit 32, which are illustrated in FIG. 1, respectively. The storage unit 504 is configured to store the comprehensive drug database and the drug database. The drug database may be dedicated to each drug sorting device 1, or may be common to the drug sorting devices 1.

For example, in the data management device 500, the transmission/reception unit 501 receives, from each drug sorting device 1, the image data on the drugs sorted into the temporarily determined area Ar12 in each drug sorting device 1. Then, the above-mentioned drug registration processing is performed on each piece of image data. The registration unit 521 registers the adjusted image data in the drug database in association with the drug data identified by the user.

The control unit 502 controls the transmission/reception unit 501 to transmit the drug database in which the adjusted image data is registered to each drug sorting device 1. The control unit 502 may transmit only data including the adjusted image data and the drug data associated with this image data to each drug sorting device 1. The control unit 502 may also transmit the drug database only to the drug sorting device 1 that has transmitted the image data.

In this manner, the data management device 500 includes: the transmission/reception unit 501 configured to receive the image data on the drug determined to have no drug data corresponding to the image data in the drug sorting device 1; and the registration unit 521 configured to register the drug data on the drug corresponding to the image data, which has been identified by the user, in association with this image data. Thus, even when the drug sorting device 1 does not include the registration unit 70 (even when the drug sorting device 1 does not perform the drug registration processing), the image data on the estimated drug can be registered in the drug database.

In this data management system, the data management device 500 is also configured to manage the drug database to be used in each drug sorting device 1. Therefore, the storage unit 80 of each drug sorting device 1 is not required to manage the drug database.

It is also not required to use the above-mentioned line for the data transmission/reception between the drug sorting device 1 and the data management device 500. For example, a communication device (for example, personal computer (PC)) different from the drug sorting device 1 may be used to transmit/receive data to/from the data management device 500. In another case, a storage medium (for example, hard disk drive (HDD) or digital versatile disc (DVD)) including data to be transmitted to the opposite party may be delivered to the other party. When the communication device or the storage medium is used, the drug sorting device 1 is not required to include the transmission/reception unit 101. In addition, the data management device 500 is not required to include the transmission/reception unit 501.

When the comprehensive drug database is to be managed in a hospital, a ward, a pharmacy, or another such place, the data management device 500 may transmit the comprehensive drug database to a data management device installed in the hospital, the ward, the pharmacy, or another such place. In this case, the comprehensive drug database can be managed at the hospital, the ward, the pharmacy, or another such place. In another case, a storage medium in which the comprehensive drug database is stored may be distributed to the hospital, the ward, the pharmacy, or another such place.

Second Embodiment

Figure 14A:
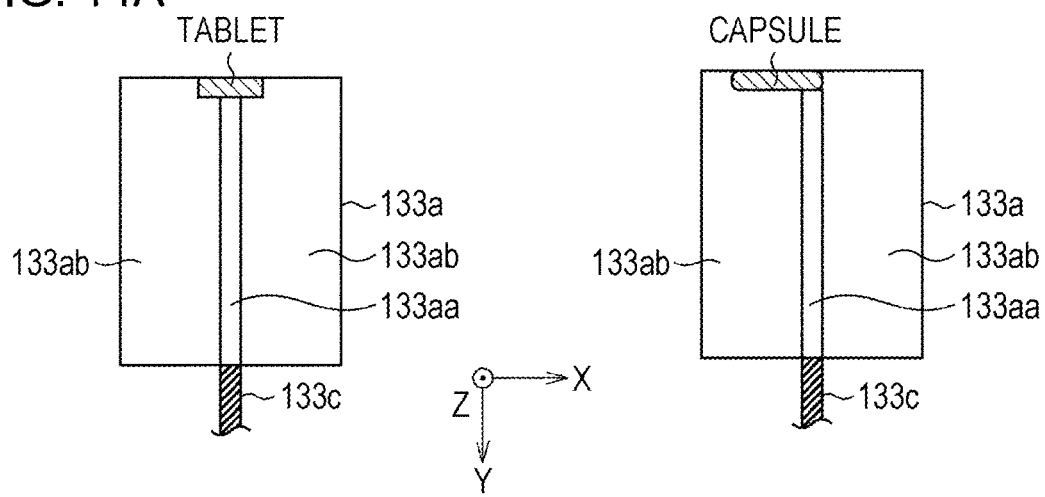
FIG. 14A is a plan view for illustrating examples of the drug loading stage that has moved to an arrangement area.
Figure 14B:
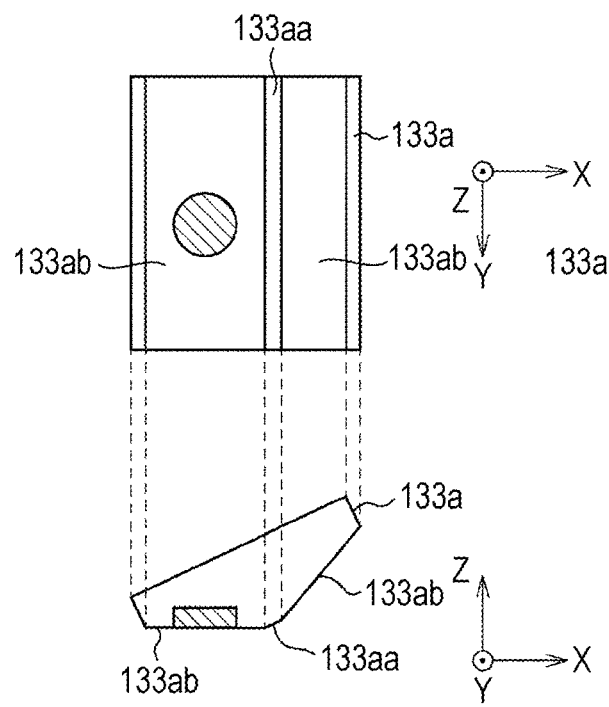
FIG. 14B and FIG. 14C are each a plan view for illustrating an example of the drug loading stage obtained after a position of a drug is adjusted.
Figure 14C:
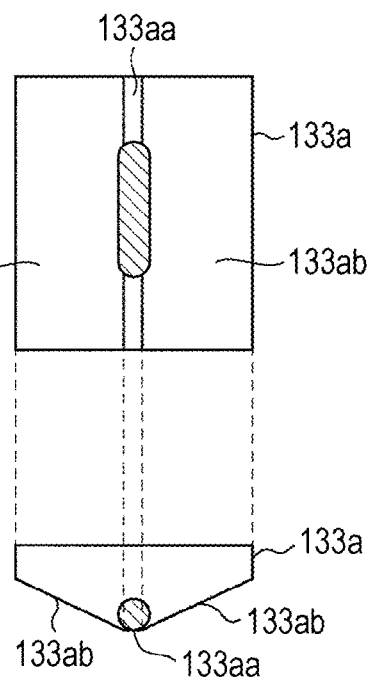

Other embodiments of this disclosure are described below. For the sake of convenience of description, members having the same functions as those of the members described in the above-mentioned embodiment are denoted by the same reference symbols, and description thereof is not repeated. The same applies to the subsequent embodiments. FIG. 14A is a plan view for illustrating examples of the drug loading stage 133a that has moved to the arrangement area Ar2, and FIG. 14B and FIG. 14C are each a plan view for illustrating an example of the drug loading stage 133a obtained after a position of a drug is adjusted.

The drug sorting device 1 according to this embodiment is not required to include the registration unit 70. That is, two areas of the confirmed area Ar11 and the temporarily determined area Ar12 are not required to be set in the second accommodating portion 14. In this case, the control unit 60a sorts the drug whose type has been successfully discriminated and the estimated drug into any one of the sorting positions (sorting cups 141) in the second accommodating portion 14. That is, when there is a vacant sorting cup 141, the estimated drug is also sorted into the second accommodating portion 14 without being sorted into the standby tray 15.

That is, it suffices that the drug sorting device 1 according to this embodiment includes at least the following components in its basic configuration. The same applies to the subsequent embodiments.

The first accommodating portion 11 configured to accommodate a plurality of types of drugs in a mixed state The second accommodating portion 14 configured to accommodate the drugs in a state of being sorted by type The image pick-up unit 13 configured to pick up an image of the drug taken out from the first accommodating portion 11

The discriminating unit 64 configured to discriminate the type of the drug based on the image picked up by the image pick-up unit 13

The conveying/sorting unit 12 configured to store the drug into the second accommodating portion 14 for each type based on the discrimination result obtained by the discriminating unit 64

As described in the first embodiment, the swiveling mechanism 133b illustrated in FIG. 3A and FIG. 3B can vibrate the drug loading stage 133a. It is possible to orient the inscribed information or the printed information in a predetermined direction by causing the swiveling mechanism 133b to vibrate the drug loading stage 133a.

Here, as illustrated in FIG. 14A, when the drug loading stage 133a is swiveled by the swiveling mechanism 133b to move from the receiving area Ar1 to the arrangement area Ar2, the drug may move to an end portion of the drug loading stage 133a due to a centrifugal force acting on the drug. In this case, when fixed vibration is performed irrespective of the size or the shape of the drug, the drug may continuously collide with an edge portion of the drug loading stage 133a, and the drug may thereby fail to be oriented in the predetermined direction. When the drug fails to be oriented in the predetermined direction, the number of times of the image pick-up may increase, or there is a possibility that only an image from which it is difficult to extract the inscribed information or the printed information is picked up.

In the drug sorting device 1 according to this embodiment, the swiveling mechanism 133b (swinging mechanism) swings (vibrates) the drug loading stage 133a arranged in the arrangement area Ar2 based on the size and the shape of the drug placed on the drug loading stage 133a.

Specifically, the image pick-up control unit 63 identifies the length (size) and shape of the drug included in the image based on the image picked up by the first camera 131. A known technology can be adopted for this identification. In addition, the storage unit 80 stores the length of the drug, the shape of the drug, a vibration amount (magnitude of vibration) of the drug loading stage 133a, and the number of vibrations per unit time in association with one another. The vibration amount and the number of vibrations are set through, for example, an experiment.

When the drug is a tablet, as illustrated in FIG. 14B, for example, the vibration amount and the number of vibrations are set so that the drug is placed in a central vicinity of the slope surface portion 133ab exhibited when one slope surface portion 133ab is changed to a substantially horizontal state from the state illustrated in FIG. 14A. When the drug is a capsule, as illustrated in FIG. 14C, for example, the vibration amount and the number of vibrations are set so that the drug is placed in a central vicinity of the bottom portion 133aa exhibited when the bottom portion 133aa is changed to a substantially horizontal state from the state illustrated in FIG. 14A. For example, as the length (size) of the drug becomes smaller, a movement amount of the drug loading stage 133a due to the vibration becomes larger, and hence the vibration amount is set smaller.

The image pick-up control unit 63 vibrates the drug loading stage 133a in the arrangement area Ar2 with the vibration amount and the number of vibrations associated with the length or the shape of the drug identified from the picked-up image. Thus, the drug can be placed in a position that allows the first camera 131 to easily pick up an image of the inscribed information or the print information as illustrated in FIG. 14B in the case of a tablet and as illustrated in FIG. 14C in the case of a capsule. Therefore, it is possible to prevent an increase in number of times of the image pick-up.

It is also possible to prevent the drug from adversely protruding from the drug loading stage 133a due to the vibration of the drug loading stage 133a by vibrating the drug loading stage 133a based on the size and the shape of the drug. In addition, it is possible to prevent the drug from continuously colliding with the edge portion of the drug loading stage 133a due to the vibration of the drug loading stage 133a. Therefore, a possibility of damage to the drug due to the collision can be reduced (burden on the drug can be reduced).

Third Embodiment

Figure 15:
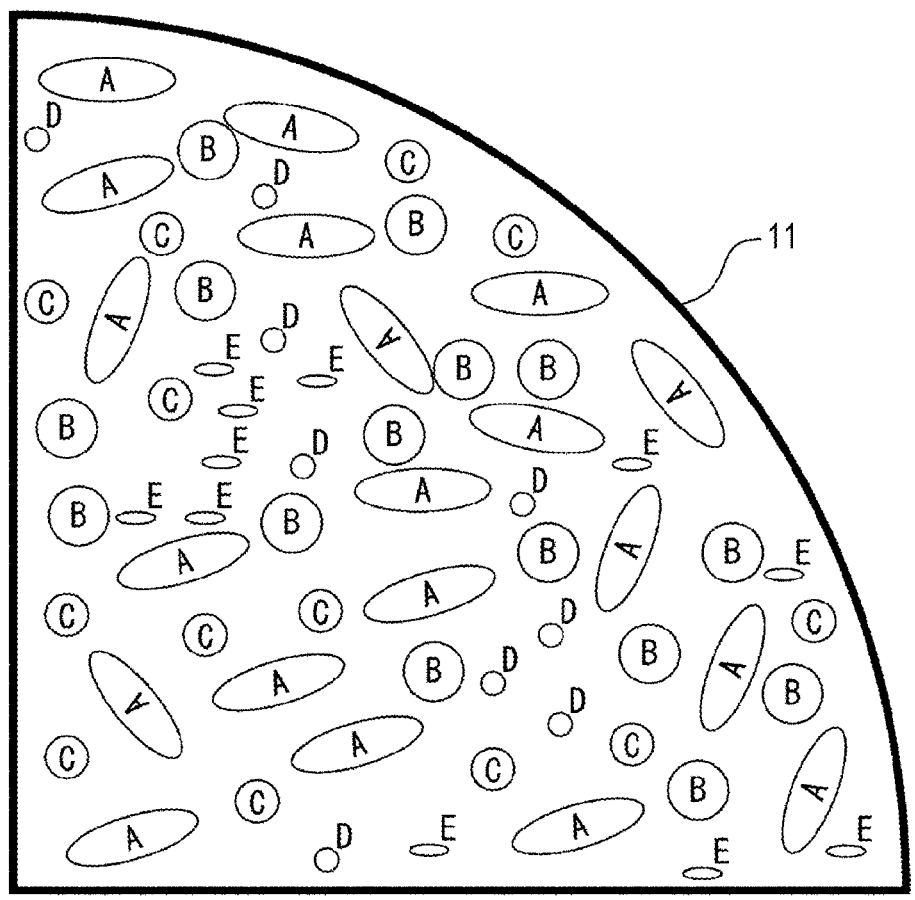
FIG. 15 is a diagram for illustrating an example of an image of a first accommodating portion which is picked up by a second camera.

In this embodiment, speedup of the discrimination processing is described. FIG. 15 is a diagram for illustrating an example of an image of the first accommodating portion 11 which is picked up by the second camera 121.

In addition to the basic configuration described in the second embodiment, in the same manner as in the first embodiment, the drug sorting device 1 according to this embodiment includes the suction mechanism (takeout mechanism) configured to take out the drug accommodated in the first accommodating portion 11 and the second camera 121 (second image pick-up unit) configured to pick up an image of the drug when the suction mechanism takes out the drug.

The conveyance control unit 61 determines a drug to be sucked by the suction mechanism from among a plurality of types of drugs accommodated in the first accommodating portion 11 based on a result of analyzing, by the image pick-up control unit 63, the images picked up by the second camera 121. The conveyance control unit 61 may determine the drug to be sucked by the suction mechanism based on a size of a contour of the drug (object) included in the image detected by the image pick-up control unit 63. A known technology may be adopted for detection of the contour. In addition, an order in which the drugs are taken out is set in advance. For example, the drugs are set to be taken out in descending order of size of the contour.

When a drug takeout order is set based on the size of the drug in this manner, the suction mechanism is highly likely to continuously take out the drugs having the same type. For example, as illustrated in FIG. 15, it is assumed that the images picked up by the second camera 121 include drugs "A" to "E" having different types (sizes). The sizes are assumed to satisfy "(drug "A")>(drug "B")>(drug "C")> (drug "D")>(drug "E")."

When the order of taking out the drugs is set as described above, in the example illustrated in FIG. 15, the suction mechanism first takes out the drugs "A" continuously. When the takeout of the drugs "A" is completed, the drugs "B" are then continuously taken out. After that, the drugs "C" are continuously taken out, then the drugs "D" are continuously taken out, and finally the drugs "E" are continuously taken out. That is, the suction mechanism continuously takes out the drugs for each of the drug "A" to the drug "E."

In this case, there is a high possibility that the discriminating unit 64 continuously performs the discrimination processing on the drugs of the same type. Therefore, in the drug sorting device 1 according to this embodiment, the discriminating unit 64 determines whether or not the matching degree between the contour of the drug currently taken out by the suction mechanism and the contour of the drug taken out by the suction mechanism up to the previous time is equal to or larger than a predetermined value in the image picked up by the second camera 121. Then, when the discriminating unit 64 determines that the matching degree is equal to or higher than the predetermined value, the discriminating unit 64 applies the drug data applied at the time of the discrimination of the type of the drug taken out up to the previous time to the discrimination of the type of the drug currently taken out.

It suffices that the predetermined value is set, for example, to such an extent that it can be determined that, when the contours of drugs having the same type are compared with each other by performing an experiment, the drugs having those contours are the drugs having the same type. In addition, a known technology may be adopted for calculation of the matching degree. The matching degree may also be determined by, for example, the conveyance control unit 61.

Specifically, the image pick-up control unit 63 analyzes the image picked up by the second camera 121, to thereby detect the contours of all the drugs included in the first accommodating portion 11. The conveyance control unit 61 determines the drug to be taken out based on the drug takeout order set in advance. The conveyance control unit 61 stores, into the storage unit 80, contour data representing the contour of the drug determined as the drug to be taken out.

In the same manner as in the first embodiment, the discriminating unit 64 extracts the feature of the taken-out drug from the image of this drug picked up by the first camera 131, and compares this feature with the drug database, to thereby discriminate the type of this drug. The discriminating unit 64 stores the currently identified type of the drug (drug data) into the storage unit 80 in association with the contour data on this drug.

The conveyance control unit 61 takes out the next drug based on the drug takeout order set in advance, and at the same time, stores the contour data on this drug into the storage unit 80. The discriminating unit 64 calculates the matching degree between the contours of those drugs by comparing the contour data on the previously taken-out drug and the contour data on the currently taken-out drug, and determines whether or not this matching degree is equal to or higher than the predetermined value. When the discriminating unit 64 determines that the matching degree is equal to or higher than the predetermined value, the discriminating unit 64 compares the feature of the currently taken-out drug with the drug data associated with the contour data on the previously taken-out drug, to thereby discriminate the type of this drug.

When the discriminating unit 64 has successfully discriminated the type of the current drug through use of the drug data on the previously taken-out drug, the discriminating unit 64 repeatedly performs the above-mentioned processing. That is, when the matching degree between the contour data on the currently taken-out drug and the contour data on the drug that has been taken out up to the previous time stored in the storage unit 80 is equal to or higher than the predetermined value, the discriminating unit 64 compares the feature of the currently taken-out drug with the drug data on the drug that has been taken out up to the previous time.

As described above, when the drugs having the same type are accommodated in the first accommodating portion 11, the drugs having the same type are continuously taken out. In this embodiment, when the above-mentioned matching degree is equal to or higher than the predetermined value, the type of the currently taken-out drug is discriminated through use of the drug data on the drug that has been taken out up to the previous time on the assumption that the drug having the same type as that of the previous one has been taken out. Thus, unlike in the first embodiment, it is not required to compare the feature of the drug extracted from the image picked up by the first camera 131 with the drug database for each of the drugs having the same type. Therefore, it is possible to shorten a processing time period required for discriminating the types of the drugs.

When the discriminating unit 64 discriminates that the above-mentioned matching degree is lower than the predetermined value, the discriminating unit 64 determines that a drug having a type different from that of the previous drug has been taken out, and in the same manner as in the first embodiment, discriminates the type of this drug through use of the drug database. In response to this determination result, the conveyance control unit 61 updates the contour data on the drug stored in the storage unit 80 to the contour data on the currently taken-out drug. The discriminating unit 64 uses the updated contour data in the subsequent processing. The processing for updating the contour data may be performed by the conveyance control unit 61.

Here, there is a case in which drugs having different types but substantially the same size are accommodated in the first accommodating portion 11. In this case, the size of the currently taken-out drug is substantially the same as that of the drug that has been taken out up to the previous time, but the type of the currently taken-out drug may be different from the type of the drug that has been taken out up to the previous time. In this case, the discriminating unit 64 determines that the above-mentioned matching degree is equal to or higher than the predetermined value, but cannot discriminate the type of the currently taken-out drug even when the comparison is performed through use of the drug data on the drug that has been taken out up to the previous time.

In a case of continuously taking out drugs having substantially the same size but different types, every time such a drug is taken out, it is determined whether or not the above-mentioned matching degree is equal to or higher than the predetermined value, and at the same time, the comparison is performed through use of the drug data on the drug that has been taken out up to the previous time. Then, each time the comparison fails, in the same manner as in the first embodiment, the discriminating unit 64 discriminates the type of this drug through use of the drug database and a result of analyzing the image picked up by the first camera 131 for the currently taken-out drug. Therefore, when drugs having substantially the same size but different types are sequentially taken out, the processing time period adversely becomes rather longer.

In view of this, in a case where the drug data applied at the time of discriminating the type of the drug that has been taken out up to the previous time is applied to the discrimination of the type of the currently taken-out drug, the discriminating unit 64 may discontinue the application of this drug data when the type of this drug fails to be discriminated a predetermined number of times or more. In this case, it is possible to suppress an increase in processing time period even when drugs having substantially the same size but different types are sequentially taken out. It suffices that the predetermined number of times is set to a number of times (for example, three times) that has little influence on the increase in processing time period.

When the application of the drug data applied at the time of discriminating the type of the drug that has been taken out up to the previous time is discontinued, in the same manner as in the first embodiment, the discriminating unit 64 discriminates the type of this drug through use of the drug database and a result of analyzing the image picked up by the first camera 131 for the currently taken-out drug.

As described above, the drug sorting device 1 according to this embodiment has the following configuration.

That is, the drug sorting device 1 according to one aspect of this embodiment includes: the first accommodating portion 11 configured to accommodate a plurality of types of drugs in a mixed state; the second accommodating portion 14 configured to accommodate the drugs in a state of being sorted by type; the image pick-up unit 13 (image pick-up unit) configured to pick up an image of the drug; the discriminating unit 64 configured to discriminate the type of the drug based on the image picked up by the image pick-up unit 13; the conveying/sorting unit 12 (sorting unit) configured to store the drug into the second accommodating portion 14 for each type based on the discrimination result obtained by the discriminating unit 64; the suction mechanism (takeout mechanism) configured to take out the drug accommodated in the first accommodating portion 11; and the second camera 121 (second image pick-up unit) configured to pick up an image of the drug when the suction mechanism takes out the drug. When the matching degree between the contour of the drug currently taken out by the suction mechanism and the contour of the drug taken out by the suction mechanism up to the previous time is equal to or higher than the predetermined value in the image picked up by the second camera 121, the discriminating unit 64 applies the drug data applied at the time of discriminating the type of the drug that has been taken out up to the previous time to the discrimination of the type of the currently taken-out drug.

In addition, in the drug sorting device 1 according to one aspect of this embodiment, in the above-mentioned aspect, in the case where the drug data applied at the time of discriminating the type of the drug that has been taken out up to the previous time is applied to the discrimination of the type of the currently taken-out drug, the discriminating unit 64 may discontinue the application of this drug data when the type of this drug fails to be discriminated the predetermined number of times or more.

Fourth Embodiment

Figure 16A:
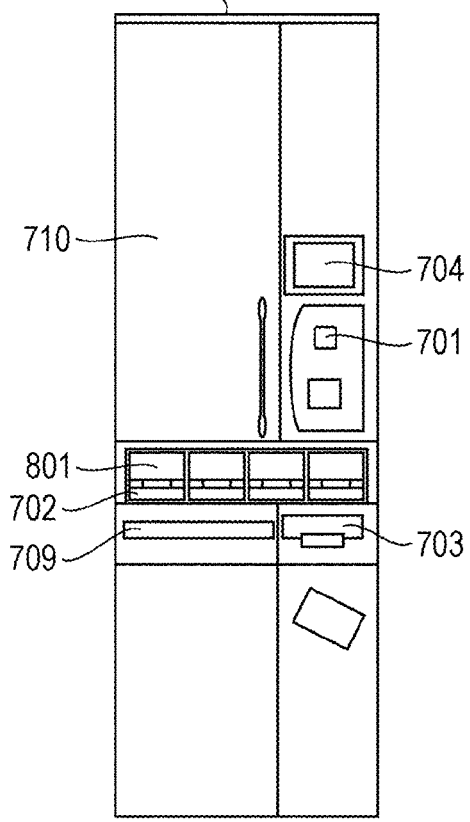
Figure 16B:
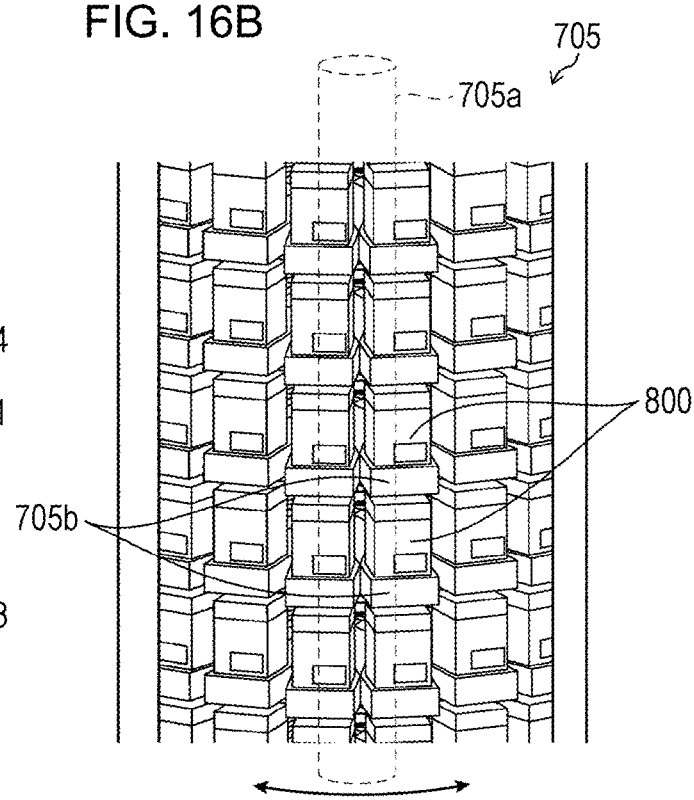
Figure 16C:
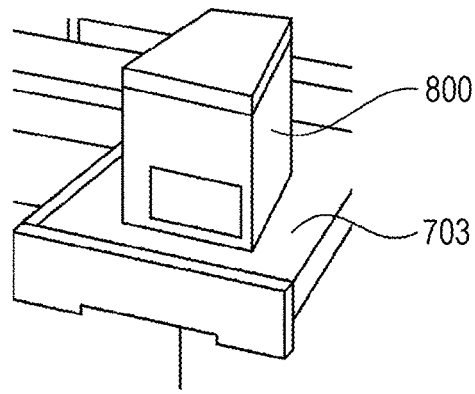
Figure 16D:
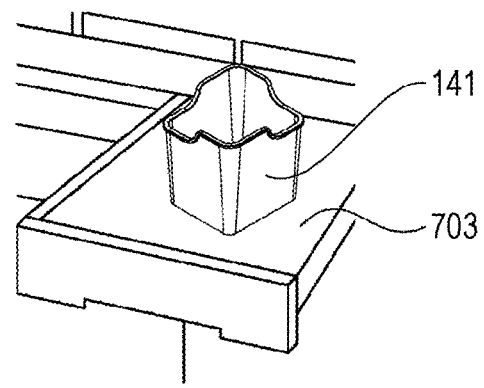
Figure 17:
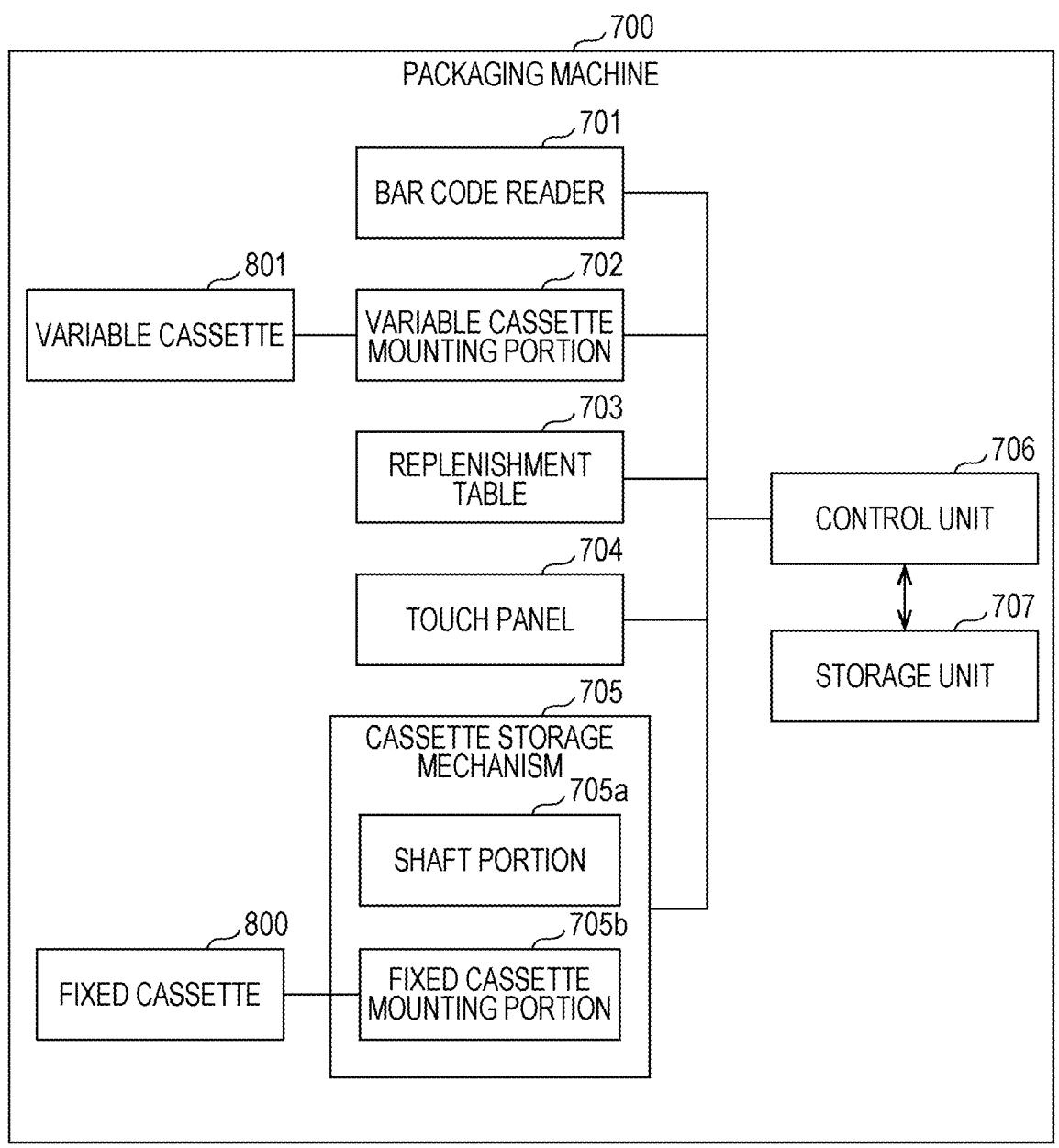
FIG. 17 is a block diagram for illustrating an example of the packaging machine.

In this embodiment, an example of a packaging machine 700 is described. FIGS. 16A to 16D are views for illustrating an example of the packaging machine 700, in which FIG. 16A is a front view of the packaging machine 700, FIG. 16B is a view for illustrating an example of a cassette storage mechanism 705, and FIG. 16C and FIG. 16D are views for illustrating a use example of a replenishment table 703. FIG. 17 is a block diagram for illustrating an example of the packaging machine 700.

The packaging machine 700 is configured to package the drug, and as illustrated in FIG. 16A and FIG. 17, includes a bar code reader 701, a variable cassette mounting portion 702, a replenishment table (filling table) 703, and a touch panel 704. The packaging machine 700 is a return destination for the drugs sorted by the drug sorting device 1. In addition, as illustrated in FIG. 16B and FIG. 17, the cassette storage mechanism 705 is provided inside the packaging machine 700 with an opening/closing door 710 being opened.

The bar code reader 701 is configured to read information included in a bar code attached to a journal issued by the drug sorting device 1 or the packaging machine 700 or a bar code attached to a drug box accommodating a drug. The bar code is, for example, a GS1 code to which a drug name or other such identification information is added.

The variable cassette mounting portion 702 is configured to drive a mounted variable cassette 801. The variable cassette 801 is configured to dispense an inserted drug to a packaging mechanism (not shown) built into the packaging machine 700.

As illustrated in FIG. 16C, the replenishment table 703 is a table on which a fixed cassette 800 can be placed. One fixed cassette 800 among a plurality of fixed cassettes 800 is placed on the replenishment table 703 stored in the cassette storage mechanism 705 under a state in which the replenishment table 703 has been drawn out to a front surface side (take-out side of the fixed cassette 800) of the packaging machine 700 provided with the opening/closing door 710. An RFID reader is provided at a position on the replenishment table 703 at which the fixed cassette 800 is placed.

An RFID tag is provided on a bottom portion of the fixed cassette 800. The RFID tag stores drug data (for example, identification information) on the drug accommodated in the fixed cassette 800. When the fixed cassette 800 is placed on the replenishment table 703, the RFID reader reads out the drug data stored in the RFID tag.

The touch panel 704 is configured to receive various user inputs and to display various images.

The cassette storage mechanism 705 includes a plurality of fixed cassette mounting portions 705b (cassette storage portions) each capable of storing the fixed cassette 800 that accommodates a drug. The plurality of fixed cassette mounting portions 705b (fixed cassettes 800 stored in each fixed cassette mounting portion 705b) are provided so as to be pivotable about the Z-axis so that all the fixed cassette mounting portions 705b can be arranged on the front surface side of the packaging machine 700. That is, the cassette storage mechanism 705 includes: a shaft portion 705a configured to rotate about the Z-axis; and the plurality of fixed cassette mounting portions 705b provided substantially perpendicular to the shaft portion 705a.

In addition, as illustrated in FIG. 17, the packaging machine 700 includes: a control unit 706 configured to control each unit of the packaging machine 700; and a storage unit 707 configured to store various kinds of data. In the storage unit 707, for example, a position of each fixed cassette mounting portion 705b, a cassette number assigned to each fixed cassette 800, and the identification information on the drug accommodated in each fixed cassette 800 are stored in association with one another.

When the fixed cassette 800 is filled with a drug (or when a drug is returned to the fixed cassette 800), the bar code reader 701 reads the identification information included in the bar code attached to the journal or the drug box. The control unit 706 refers to the storage unit 707 to identify the cassette number associated with the read identification information and also identify a storage position of the fixed cassette 800 to which the identified cassette number is assigned. The control unit 706 rotates the shaft portion 705a so that the identified storage position is located on the front surface side of the packaging machine 700. Thus, the user can easily take out the fixed cassette 800 to be a filling destination of the drug.

The user can accommodate a drug into the fixed cassette 800 by taking out the fixed cassette 800 to be the filling destination of the drug, which is arranged on the front surface side of the packaging machine 700, and placing the fixed cassette 800 on the replenishment table 703. At this time, when the RFID reader reads the identification information included in the RFID tag, the control unit 706 compares the identification information read by the RFID reader with the identification information read by the bar code reader 701. Thus, it can be determined whether or not the fixed cassette 800 is an appropriate fixed cassette 800 as the filling destination of this drug even before being filled with the drug.

In this case, when the filling of the packaging machine 700 with the drug sorted by the drug sorting device 1 is not taken into consideration, it suffices that the shaft portion 705*a* is rotated with a trigger of the bar code reader 701 reading the identification information as described above. That is, in this case, it is not required to rotate the shaft portion 705*a* with a trigger of the RFID reader of the replenishment table 703 reading the identification information.

However, when the filling of the packaging machine 700 with the drug sorted by the drug sorting device 1 is taken into consideration, it is required to rotate the shaft portion 705*a* with a trigger of the reading of the identification information stored in the RFID tag of the sorting cup 141. This is because it is required to use the identification information stored in the RFID tag of the sorting cup 141 to arrange the fixed cassette 800 accommodating drugs having the same type as that of drugs accommodated in the sorting cup 141 on the front surface side of the packaging machine 700 and to enable this fixed cassette 800 to be taken out.

When the fixed cassette 800 stored in the packaging machine 700 is to be filled with the drugs sorted by the drug sorting device 1, the user carries, to the packaging machine 700, the sorting cup 141 accommodating the drug with which the fixed cassette 800 is to be filled. Then, as illustrated in FIG. 16D, the user places the sorting cup 141 on the replenishment table 703 of the packaging machine 700. That is, the replenishment table 703 can also be said to be a table on which the sorting cup 141 can be placed.

In the drug sorting device 1, the identification information (drug data) on the sorted drug is stored in the RFID tag of the sorting cup 141. Therefore, when the sorting cup 141 is placed on the replenishment table 703, the RFID reader reads out the identification information stored in the RFID tag of the sorting cup 141.

In this case, the control unit 706 refers to the storage unit 707 to identify the cassette number associated with the identification information read from the RFID tag of the sorting cup 141 by the RFID reader and to identify the storage position of the fixed cassette 800 to which the identified cassette number is assigned. That is, with a trigger of the RFID reader reading the identification information, the control unit 706 rotates the shaft portion 705*a* so that the identified storage position (fixed cassette mounting portion 705*b*) is arranged on the front surface side of the packaging machine 700.

The user can take out the fixed cassette 800 to be the filling destination of the drugs accommodated in the sorting cup 141, which is arranged on the front surface side of the packaging machine 700, and place the fixed cassette 800 on the replenishment table 703, to thereby accommodate this drug into this fixed cassette 800.

It suffices that the RFID reader of the replenishment table 703 reads the identification information only when the sorting cup 141 is provided. For example, when the replenishment table is provided with a weighing device (not shown), the control unit 706 may rotate the shaft portion 705*a* through use of the identification information read by the RFID reader after determining that the sorting cup 141 is provided when a weight is less than a predetermined value.

Modification Example

The cassette storage mechanism 705 is a mechanism in which the plurality of fixed cassette mounting portions 705*b* pivot about the shaft portion 705*a*, but this disclosure is not limited thereto. For example, a non-pivoting cassette storage mechanism in which a plurality of fixed cassette mounting portions do not pivot may be used.

Figure 18A:
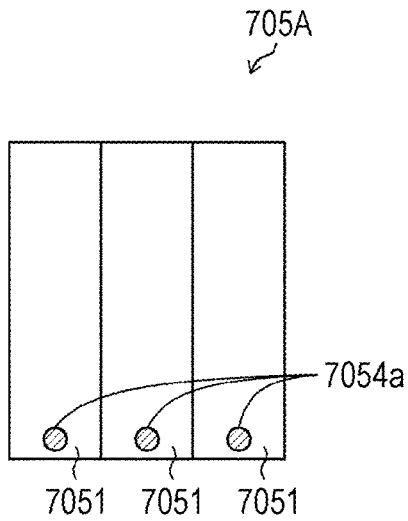
FIG. 18A, FIG. 18B, FIG. 18C, and FIG. 18D are views for illustrating examples of a non-pivoting cassette storage mechanism.
Figure 18B:
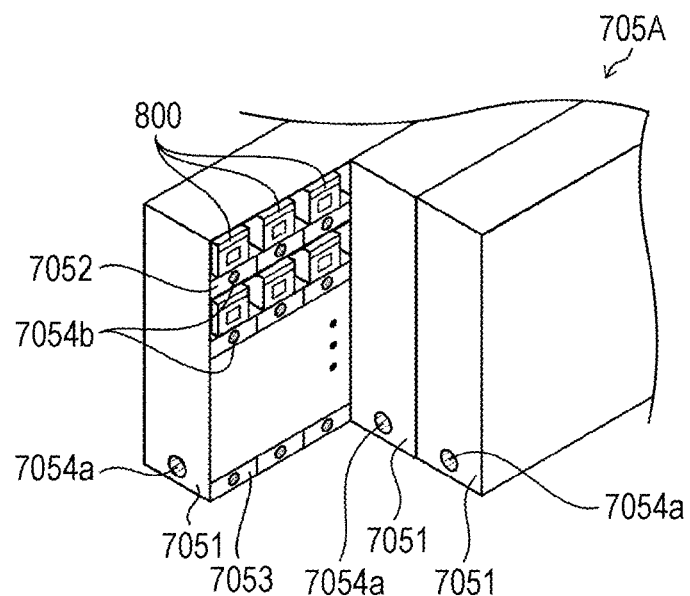
Figure 18C:
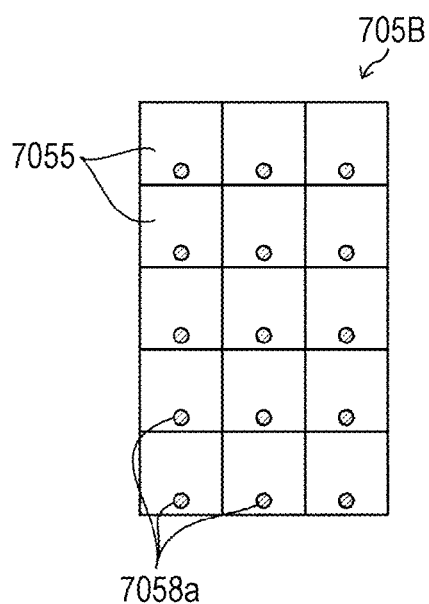
Figure 18D:
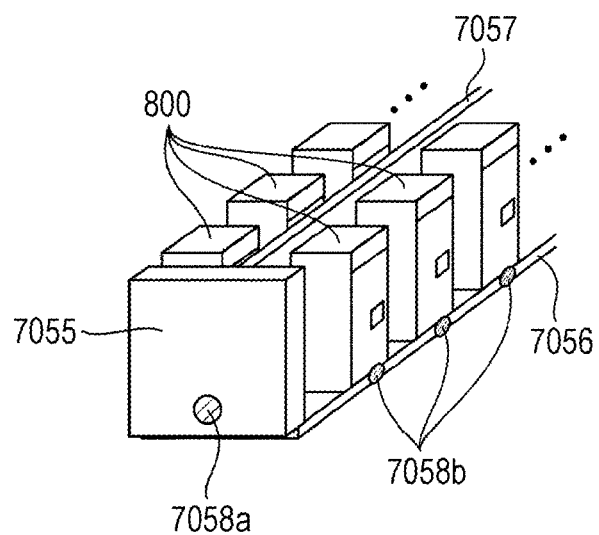

FIG. 18A and FIG. 18B are views for illustrating an example of a non-pivoting cassette storage mechanism 705A. FIG. 18A is a front view of the cassette storage mechanism 705A, and FIG. 18B is a perspective view of the cassette storage mechanism 705A with a cassette storage shelf 7051 being drawn out. FIG. 18C and FIG. 18D are views for illustrating an example of a non-pivoting cassette storage mechanism 705B. FIG. 18C is a front view of the cassette storage mechanism 705B, and FIG. 18D is a perspective view of the cassette storage mechanism 705B with a cassette storage shelf 7055 being drawn out.

As illustrated in FIG. 18A, the cassette storage mechanism 705A includes a plurality of cassette storage shelves 7051 that can be drawn out to the front surface side of the packaging machine 700. As illustrated in FIG. 18B, the cassette storage shelf 7051 is provided with a plurality of partition plates 7052 so as to be parallel to bottom portions 7053. The plurality of partition plates 7052 and the bottom portions 7053 form a plurality of fixed cassette mounting portions.

An informing unit 7054*a* is provided on a front surface portion of the cassette storage shelf 7051. In addition, each of the plurality of fixed cassette mounting portions of the partition plates 7052 and the bottom portions 7053 is provided with an informing unit 7054*b*. The informing units 7054*a* and 7054*b* are members for informing of the storage position of the fixed cassette 800 identified as the filling destination of the drug, and are implemented by, for example, a light emitting diode (LED). As described above, when the control unit 706 refers to the storage unit 707 to identify the storage position of the fixed cassette 800 as the filling destination of the drug, the informing unit 7054*a* of the cassette storage shelf 7051 in which this storage position is located and the informing unit 7054*b* of this storage position are caused to emit light.

Meanwhile, as illustrated in FIG. 18C, the cassette storage mechanism 705B includes a plurality of cassette storage shelves 7055 that can be drawn out to the front surface side of the packaging machine 700. As illustrated in FIG. 18D, the cassette storage shelf 7055 is provided with a partition plate 7057 for dividing a bottom portion 7056 into two in a depth direction (drawing direction). A plurality of fixed cassette mounting portions on which the fixed cassette 800 can be placed are formed in the bottom portion 7056 on both sides across the partition plate 7057 in the depth direction.

An informing unit 7058*a* having the same function as that of the informing unit 7054*a* is provided on a front surface portion of the cassette storage shelf 7055. In addition, each of the plurality of fixed cassette mounting portions of the bottom portions 7056 is provided with an informing unit 7058*b* having the same function as that of the informing unit 7054*b*. As described above, when the control unit 706 refers to the storage unit 707 to identify the storage position of the fixed cassette 800 as the filling destination of the drug, the informing unit 7058*a* of the cassette storage shelf 7055 in which this storage position is located and the informing unit 7058*b* of this storage position are caused to emit light.

The non-pivoting cassette storage mechanism is not limited to the configuration illustrated in FIGS. 18A to 18D. For example, the number of cassette storage shelves may be one. The form of FIG. 18A may also have a configuration in which one cassette storage shelf is divided by a partition plate extending in the depth direction, and has the fixed cassettes 800 placed thereon in two rows in the depth direction. The form of FIG. 18C may also have a configuration in which one cassette storage shelf is not divided by the partition plate, and has the fixed cassettes 800 placed thereon in one row in the depth direction.

In addition, the non-pivoting cassette storage mechanism is not required to have a configuration in which a plurality of fixed cassette mounting portions are provided to one cassette storage shelf. For example, the non-pivoting cassette storage mechanism may have a configuration in which all the plurality of fixed cassette mounting portions are arranged so as to be oriented toward the front surface side of the packaging machine 700, and can be drawn out to the front surface side. In this case, an informing unit is provided on each of the plurality of fixed cassette mounting portions.

As described above, the non-pivoting cassette storage mechanism in this modification example is provided with an informing unit, to thereby allow the user to take out a desired fixed cassette 800.

The informing unit may be the touch panel 704. In this case, for example, an image indicating each storage position is displayed on the touch panel 704, and when the control unit 706 identifies the storage position of the fixed cassette 800 as the filling destination of the drug, the control unit 706 highlight-displays this storage position. When a plurality of fixed cassette mounting portions are provided to one cassette storage shelf as illustrated in FIGS. 18A to 18D, not only this storage position but also the cassette storage shelf in which this storage position is located is also highlight-displayed.

Fifth Embodiment

The drug sorting device 1 may be configured to display a user setting image (user setting screen) Im8 illustrated in FIG. 19. FIG. 19 is a diagram for illustrating an example of the user setting image Im8.

As illustrated in FIG. 19, the user setting image Im8 includes sorting condition setting areas Ar81, Ar82, and Ar83 in which sorting conditions for discarding of a drug accommodated in the first accommodating portion 11 without returning the drug to the packaging machine 700 or the drug shelf can be set.

The sorting condition setting area Ar81 is an area in which the input of the number of days elapsed since a last packaging date on which dispensing was performed by the packaging machine 700 can be received. Information indicating the last packaging date of each drug can be acquired from the packaging machine 700. The control unit 60*a* conveys the drug having a drug sorting date later than the last packaging date indicated by the acquired information by more than the input number of days, to the collection tray 16 without performing the discrimination processing thereon.

The drug returned to the fixed cassette 800 of the packaging machine 700 is placed on the drugs accommodated in the fixed cassette 800 by the time of the returning. When a drug having a manufacturing date older than those of the drugs accommodated in the fixed cassette 800 is returned, this drug is accommodated above the fixed cassette 800. In general, the drug is dispensed from below the fixed cassette 800, and hence when the drug having an old manufacturing date is returned, this drug is not easily dispensed. Therefore, the drug having an older manufacturing date is not preferred to be accommodated at an upper position for the operation or safety of the drug. The same applies to a case in which a drug having an old manufacturing date is returned to a drug container on the drug shelf or a case in which the drug is packaged with a packaging paper sheet and returned to the drug shelf.

In this embodiment, the above-mentioned number of elapsed days can be set as the sorting condition in the sorting condition setting area Ar81, and hence the drug having an old manufacturing date can be conveyed to the collection tray 16. Therefore, this drug can be discarded, to thereby be able to avoid the use of this drug.

The sorting condition setting area Ar82 is an area in which the input of a drug unit price can be received as the above-mentioned sorting condition. For example, the drug unit price of each drug is stored in the storage unit 80 in association with the drug data, for example. When a drug unit price has been input to the sorting condition setting area Ar82, the control unit 60*a* conveys the drug having a price equal to or less than this drug unit price to the collection tray 16 without performing the discrimination processing thereon.

The sorting condition setting area Ar83 is an area in which the user can input the drug name of the drug to be discarded as the above-mentioned sorting condition. When the drug name has been input to the sorting condition setting area Ar83, the control unit 60*a* conveys this drug to the collection tray 16 without performing the discrimination processing thereon.

In this manner, the drug corresponding to the information input to the sorting condition setting areas Ar82 and Ar83 can be conveyed to the collection tray 16. That is, in the same manner as in the case of using the sorting condition setting area Ar81, the drug desired to be discarded by the user can be conveyed to the collection tray 16. Therefore, this drug can be discarded, to thereby be able to avoid the use of this drug.

Sixth Embodiment

In this embodiment, a configuration for shortening a time period for the drug sorting processing is described with reference to FIG. 1. It suffices that the drug sorting device 1 according to this embodiment has the basic configuration described in the second embodiment. That is, in the same manner as in the second embodiment, it is not always required to include the registration unit 70, and the two areas of the confirmed area Ar11 and the temporarily determined area Ar12 are not always required to be set in the second accommodating portion 14.

As described in the first embodiment with reference to FIG. 1 and other figures, the discriminating unit 64 discriminates the type of the drug based on the image picked up by the first camera 131. For example, the discriminating unit 64 extracts the features of the drug including the size, the shape, the inscription, the print, the division line, and the representative color by analyzing the visible light image and the ultraviolet light image, and compares the features of the drug with the drug database. Specifically, the discriminating unit 64 narrows down the candidates for the drug data from the drug database through use of at least one of the extracted features of the drug, then reads the identification information or other such information indicated on the inscription or the print, and further narrows down the types of drugs from among the above-mentioned candidates through use of, for example, the pattern matching.

In this case, an increase in number of pieces of drug data registered in the drug database means an increase in number of pieces of drug data to be compared with the extracted feature of the drug. Therefore, as the number of pieces of drug data increases, a comparison time period between the extracted feature of the drug and the drug database increases, to thereby in turn adversely increase the processing time period for the drug sorting processing.

In the drug sorting device 1 according to this embodiment, the discriminating unit 64 has the following functions in order to suppress the above-mentioned increase in processing time period. That is, the discriminating unit 64 discriminates the type of the drug by comparing the feature of the drug extracted from the image picked up by the first camera 131 with the drug data relating to the drug packaged by the packaging machine 700 within a predetermined period (for example, within one month) among the pieces of drug data relating to the plurality of registered drugs. That is, the discriminating unit 64 sets, as a comparison target of the feature of the drug extracted from the picked-up image, the drug data relating to the drug that has been actually packaged by the packaging machine 700 within the predetermined period.

The packaging machine 700 (see FIGS. 16A to 16D) and the drug sorting device 1 manage a date/time at which a drug is packaged by each of the packaging machine 700 and the packaging mechanism 6 of the drug sorting device 1 in association with drug data on the drug to be packaged, respectively. When the drug sorting device 1 and the packaging machine 700 are connected to each other so as to enable communication therebetween, the drug sorting device 1 can manage not only the date/time at which the drug is packaged by the packaging mechanism 6 but also the date/time at which the drug is packaged by the packaging machine 700. The date/time at which the drug is packaged by each of the packaging machine 700 and the packaging mechanism 6 of the drug sorting device 1 may be managed by a higher-level system connected to the packaging machine 700 and the drug sorting device 1 so as to enable communication therebetween. The drug sorting device 1 may also identify the date/time at which the drug is packaged by the packaging machine 700 or the packaging mechanism 6 based on received prescription data (for example, prescription information per patient).

The discriminating unit 64 extracts, from the drug database, drug data having the packaged date/time that falls within the predetermined period, and sets the extracted drug data as the comparison target with the feature of the drug extracted from the picked-up image. Thus, it is not always required to set all the pieces of drug data registered in the drug database as comparison targets described above, and hence it is possible to reduce the above-mentioned comparison time period (time period for the discrimination processing for the type of the drug).

The drug sorted by the drug sorting device 1 is packaged by the packaging mechanism 6 or the packaging machine 700, or returned to the drug shelf. That is, the sorted drug is used for prescription. Therefore, an old drug (for example, drugs having packaged date/time that falls outside the predetermined period) is to be discarded (is not subjected to packaging or returning), and is therefore less likely to be required to be sorted by the drug sorting device 1. Therefore, there is a high possibility that the type of the drug accommodated in the first accommodating portion 11 can be discriminated even when the drug data relating to the drug packaged within the predetermined period is used as the comparison target.

When the drug data relating to the drug packaged within the predetermined period does not include the feature of the drug included in the picked-up image, the conveying/sorting unit 12 may convey this drug to the standby tray 15. In the case of the first embodiment, the conveying/sorting unit 12 may convey this drug to the standby tray 15 or the temporarily determined area Ar12 set in the second accommodating portion 14. In addition, the discriminating unit 64 may use all the pieces of drug data (excluding the piece of drug data set as the comparison target) registered in the drug database as the comparison target.

Seventh Embodiment

In this embodiment, a configuration for shortening a time period for the drug sorting processing is described with reference to FIG. 1. It suffices that, in the same manner as in the sixth embodiment, the drug sorting device 1 according to this embodiment has the basic configuration described in the second embodiment.

As illustrated in FIG. 1, the drug sorting device 1 according to this embodiment includes the standby tray 15 and the sorting control unit 62 in addition to the above-mentioned basic configuration. As described in the first embodiment as well, the standby tray 15 is a tray (temporary accommodating portion) for temporarily placing drugs that have failed to be stored in the second accommodating portion 14. As described in the first embodiment as well, the sorting control unit 62 is configured to determine the sorting position of each drug based on the discrimination result obtained by the discriminating unit 64. In addition, the sorting control unit 62 is configured to store the determined sorting position and the drug data that has been used by the discriminating unit 64 for the comparison, into the storage unit 80 in association with each other.

In the drug sorting device 1 according to this embodiment, when a drug accommodated in the standby tray 15 is accommodated into the second accommodating portion 14 (when re-sorted), the discriminating unit 64 performs the following processing. That is, the discriminating unit 64 compares the image of this drug, which has been taken out from the standby tray 15 and has its image picked up by the first camera 131, with the drug data associated with the standby tray 15 determined as the sorting position by the sorting control unit 62, to thereby discriminate the type of this drug.

The above-mentioned processing in the case of the re-sorting may be performed by another discriminating unit (second discriminating unit) different from the discriminating unit 64. This embodiment is described on the assumption that this processing is performed by the discriminating unit 64 (that is, the discriminating unit 64 has the function of the second discriminating unit).

When the confirmed area Ar11 and the temporarily determined area Ar12 are not set in the second accommodating portion 14, the drug whose type has been discriminated is accommodated into the sorting cup 141 of the second accommodating portion 14 for each type. Under a state in which drugs are accommodated in all the sorting cups 141, when it is discriminated that the type of a drug is different from the types of the drugs accommodated in the sorting cups 141, this drug is accommodated into the standby tray 15. Meanwhile, in the case where the confirmed area Ar11 and the temporarily determined area Ar12 are set in the second accommodating portion 14, when no more drugs can be accommodated into the confirmed area Ar11, the drug later set to be accommodated into the confirmed area Ar11 may be accommodated into the standby tray 15.

The drugs accommodated in the standby tray 15 are re-sorted after there occurs a vacant sorting cup 141 in the second accommodating portion 14. That is, each drug accommodated in the standby tray 15 has its image picked up again by the first camera 131, and is then accommodated into the vacant sorting cup 141 based on the discrimination result obtained by the discriminating unit 64.

In this case, the discriminating unit 64 may extract the feature of the drug from the picked-up image and compare the feature of this drug with all the pieces of drug data registered in the drug database. However, the comparison with all the pieces of drug data requires a processing time period corresponding to the number of registered pieces of drug data. In addition, the type of the drug had been successfully discriminated as a result of performing the above-mentioned comparison before the drug has been accommodated into the standby tray 15, and hence it is not always required to perform the comparison with all the registered pieces of drug data similarly even after the drug is taken out from the standby tray 15.

In view of this, when the discriminating unit 64 is to re-sort the drugs accommodated in the standby tray 15, the discriminating unit 64 compares the image of each drug picked up after being taken out from the standby tray 15 with the drug data for which the standby tray 15 has been registered as the sorting position among all the registered pieces of drug data. Specifically, the discriminating unit 64 extracts the feature of the drug from the picked-up image of the drug, and compares the extracted feature of the drug with the drug data for which the standby tray 15 has been registered as the sorting position.

That is, the discriminating unit 64 stores the determined sorting position (standby tray 15) and the drug data used for comparing this drug by the discriminating unit 64, as a discrimination result (identification result) of the drug accommodated in the standby tray 15 in association with each other. As a result, in a case where a drug whose type had been successfully discriminated once has been accommodated into the standby tray 15, when the discrimination of the type is performed for the re-sorting for the second time, the discriminating unit 64 can discriminate the type of this drug through use of only the drug data relating to the drug, which is accommodated in the standby tray 15, and whose type has already been discriminated. Therefore, a time period for the discrimination processing can be shortened, and it is also possible to improve an identification rate of a drug.

Eighth Embodiment

In this embodiment, an example of processing performed on the packaging machine 700 side is described with reference to FIGS. 16A to 16D, FIG. 17, and FIGS. 20A and 20B to FIG. 22.

The packaging machine 700 uses a packaging mechanism (not shown) provided to the own machine to package and dispense drugs supplied from the fixed cassette 800, the variable cassette 801, and a manual distribution unit 709. For example, the packaging machine 700 packages the drugs in predetermined units of packages (for example, units of timings of administration) based on prescription data (for example, prescription information per patient). The packaging machine 700 may be provided with a powdered drug supplying unit configured to dispense powdered drugs.

As described in the fourth embodiment, when the fixed cassette 800 stored in the packaging machine 700 is to be filled with the drugs sorted by the drug sorting device 1, the user carries, to the packaging machine 700, the sorting cup 141 accommodating the drug with which the fixed cassette 800 is to be filled. Then, as illustrated in FIG. 16D, the user places the sorting cup 141 on the replenishment table 703 of the packaging machine 700. The RFID reader (reader for cassette comparison) of the replenishment table 703 reads, from the RFID tag of the sorting cup 141, information (for example, identification information (for example, YJ code) and the number of drugs) relating to the drugs accommodated in this sorting cup 141. With a trigger of the RFID reader reading the identification information, the control unit 706 uniformly pivots all the fixed cassette mounting portions 705*b* so as to arrange the identified storage position (fixed cassette mounting portion 705*b*) on the front surface side of the packaging machine 700.

In the fourth embodiment, the packaging machine 700 includes the shaft portion 705*a*, and the control unit 706 is configured to rotate the shaft portion 705*a* so that the fixed cassette mounting portion 705*b* identified as described above is arranged on the front surface side, but this disclosure is not limited thereto. The packaging machine 700 herein is not always required to include the shaft portion 705*a*. That is, the packaging machine 700 is only required to be provided with a pivoting mechanism for uniformly pivoting all the fixed cassette mounting portions 705*b* in the circumferential direction so that the fixed cassette mounting portion 705*b* identified as described above is arranged on the front surface side.

In the packaging machine 700 in this embodiment, with a trigger of the RFID reader reading the identification information, the drugs accommodated in the sorting cup 141 may not only be filled into the fixed cassette 800 but also be filled into the variable cassette 801 and the manual distribution unit 709, to thereby be able to be packaged.

Now, the fixed cassette 800, the variable cassette 801, and the manual distribution unit 709 are described.

<Fixed Cassette>

The fixed cassette 800 is a cassette (drug cassette) for which a drug having a predetermined type is set as an object to be dispensed. The fixed cassette 800 can also be said to be a dedicated cassette for which the object to be dispensed is limited to a drug having a specific type. That is, the fixed cassette 800 accommodates a drug having a specific type in advance (accommodates a predetermined drug).

In this case, the "specific type" is not limited to the type of drugs classified based on the name (component) of the drugs, and indicates that the drugs are the same in terms of at least one index of, for example, the size (weight) of the drug, the shape of the drug, a surface condition (texture) of the drug, and a hardness of the drug. That is, the fixed cassette 800 is limited to the dispensing of drugs being the same in terms of at least one index of, for example, the type, the size, the shape, the surface condition, and the hardness of the drug. The surface condition of the drug refers to, for example, such a feeling of touch as being slippery or rough.

The fixed cassette 800 can dispense the accommodated drugs for each unit amount (for example, one tablet at a time). For example, the fixed cassette 800 includes: a drug accommodating portion in which drugs are accommodated; and a drug dispensing unit provided below the drug accommodating portion and configured to individually dispense the drugs accommodated in the drug accommodating portion.

<Variable Cassette>

Figure 20A:
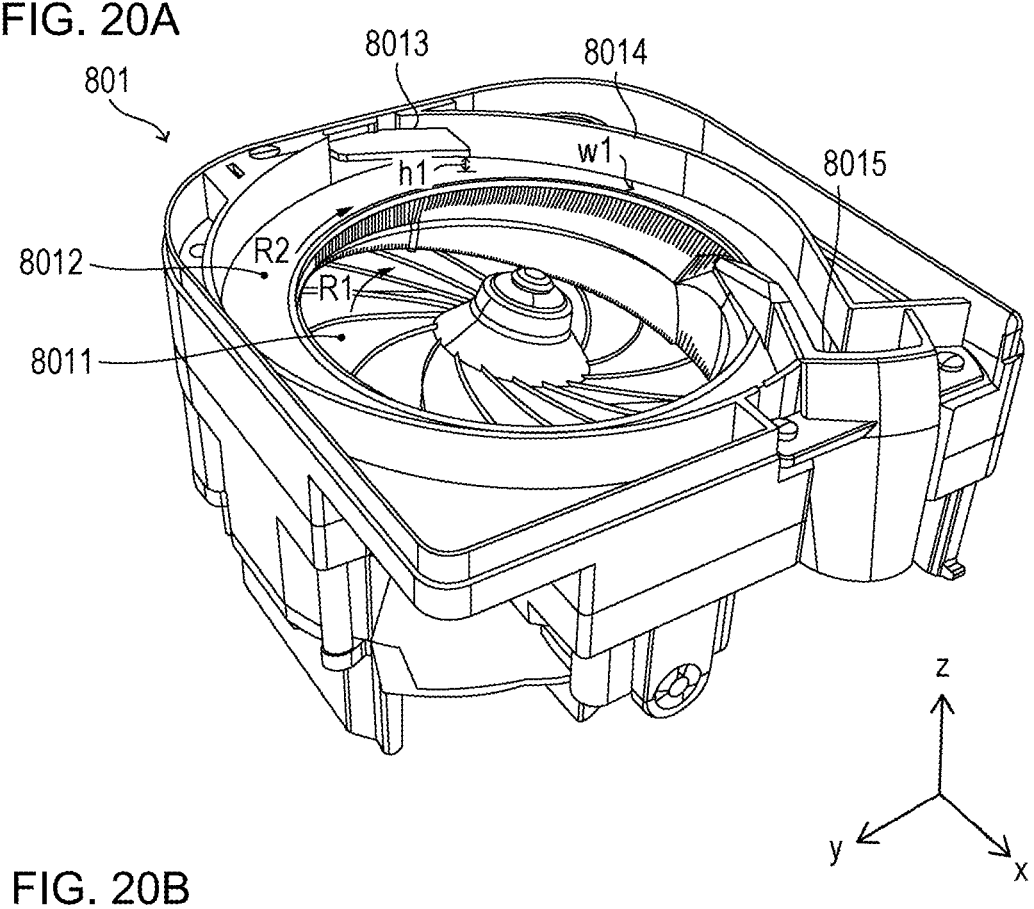
FIG. 20A is a perspective view for illustrating a configuration example of a drug dispensing machine.

FIG. 20A is a perspective view for illustrating a configuration example of the variable cassette 801. The variable cassette 801 is a cassette (drug cassette) for dispensing drugs having a type indicated by a dispensing instruction. The variable cassette 801 can also be said to be a general-purpose cassette for which the object to be dispensed is not limited to drugs having a specific type. That is, the variable cassette 801 accommodates one type of drugs among a plurality of types of drugs. Unlike the fixed cassette 800, the variable cassette 801 does not accommodate drugs having a predetermined specific type, and drugs accommodated in the variable cassette 801 can be changed depending on, for example, prescription data as appropriate. The variable cassette 801 can dispense any kind of accommodated drugs for each unit amount by changing driving conditions. The variable cassette 801 can also be said to be a cassette in which a passage path width of the drugs can be changed depending on the type of the drugs to be accommodated therein.

The variable cassette 801 can be removably mounted to the variable cassette mounting portion 702. The variable cassette mounting portion 702 is a mounting unit (motor base) to which the variable cassette 801 can be mounted. In order to dispense drugs from the mounted variable cassette 801, the variable cassette mounting portion 702 receives an instruction to dispense drugs from the control unit 706, and supplies a drive force to a driving mechanism for this drug. That is, the control unit 706 controls the variable cassette 801 through intermediation of the variable cassette mounting portion 702.

When drugs are to be dispensed, the drugs to be dispensed are allotted to one of the variable cassettes 801 owned by the user. After that, when this variable cassette 801 is provided to the variable cassette mounting portion 702, a lock of the variable cassette mounting portion 702 is released, and the variable cassette 801 becomes removable from the variable cassette mounting portion 702. The user accommodates the drugs allocated to the variable cassette 801 into the variable cassette 801, and then returns this variable cassette 801 to the variable cassette mounting portion 702, to thereby enable the variable cassette 801 to dispense the drugs.

As illustrated in FIG. 20A, the variable cassette 801 mainly includes a first rotating body 8011, a second rotating body 8012, a height regulating body 8013, and a width regulating body 8014. The first rotating body 8011 and the second rotating body 8012 are each a drug conveying mechanism to be rotated to convey the fed drugs to a dispensing port 8015. The height regulating body 8013 and the width regulating body 8014 are each a member configured to define such a drug passage path (passage path width; transfer height of h1 and transfer width of w1) as to allow the drugs to be conveyed in a row to the dispensing port 8015 on the second rotating body 8012.

<Manual Distribution Unit>

Figure 20B:
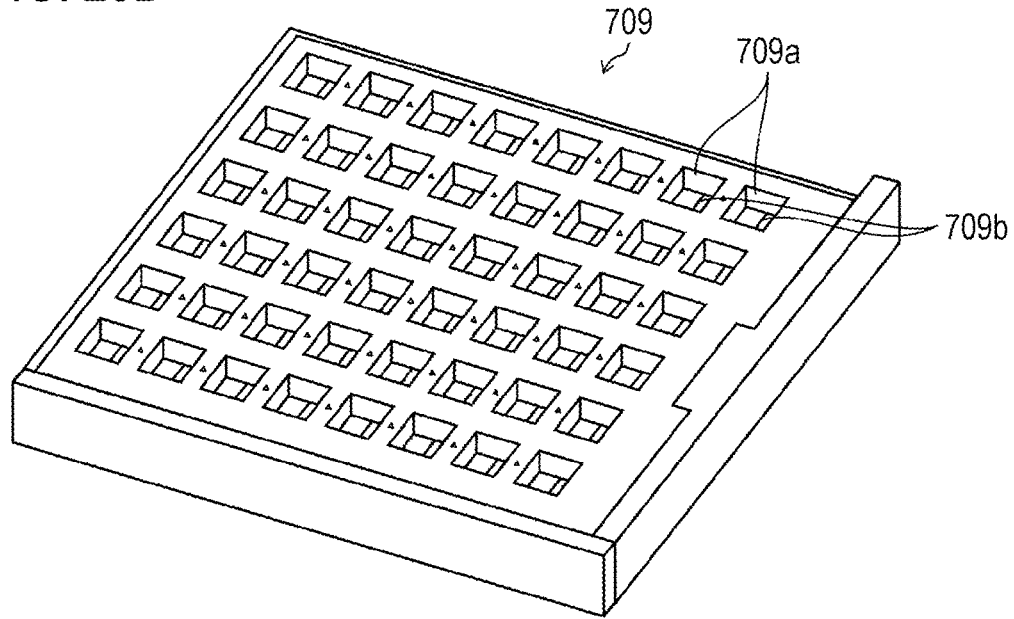
FIG. 20B is a perspective view for illustrating a configuration example of a manual distribution unit.

FIG. 20B is a perspective view for illustrating a configuration example of the manual distribution unit 709. The manual distribution unit 709 is a unit that allows the user to feed drugs to be dispensed. As illustrated in FIG. 20B, the manual distribution unit 709 includes: a plurality of manual distribution accommodating portions 709a (square measures) into which drugs are to be fed in units of packages by the user; and manual distribution dispensing portions 709b from each of which the drugs accommodated in each manual distribution accommodating portion 709a are to be dispensed for each manual distribution accommodating portion 709a.

The plurality of manual distribution accommodating portions 709a are arranged in a matrix shape. The manual distribution dispensing portion 709b is provided, for example, on a bottom portion surface of each manual distribution accommodating portion 709a so that each manual distribution accommodating portion 709a can be opened and closed individually. The user accommodates drugs in each manual distribution accommodating portion 709a while viewing an instruction sheet indicating which drug is to be stored in which manual distribution accommodating portion 709a. After that, under control of the control unit 706, each manual distribution accommodating portion 709a is individually opened at a timing determined by the packaging performed by the packaging mechanism of the own machine, to thereby dispense the drugs accommodated in each manual distribution accommodating portion 709a.

The instruction sheet is issued by the control unit 706. The control unit 706 identifies from which unit (for example, fixed cassette 800, variable cassette 801, or manual distribution unit 709) to dispense the drugs accommodated in the sorting cup 141 or the drugs included in the prescription data. When the manual distribution unit 709 is identified as a dispensing destination, the control unit 706 identifies a position of the manual distribution accommodating portion 709a for accommodating the drugs for each sorting cup 141 or based on the prescription data. The control unit 706 prints the position of the manual distribution accommodating portion 709a for accommodating the drugs, on the instruction sheet based on the above-mentioned identification.

Processing in this Embodiment

Figure 21:
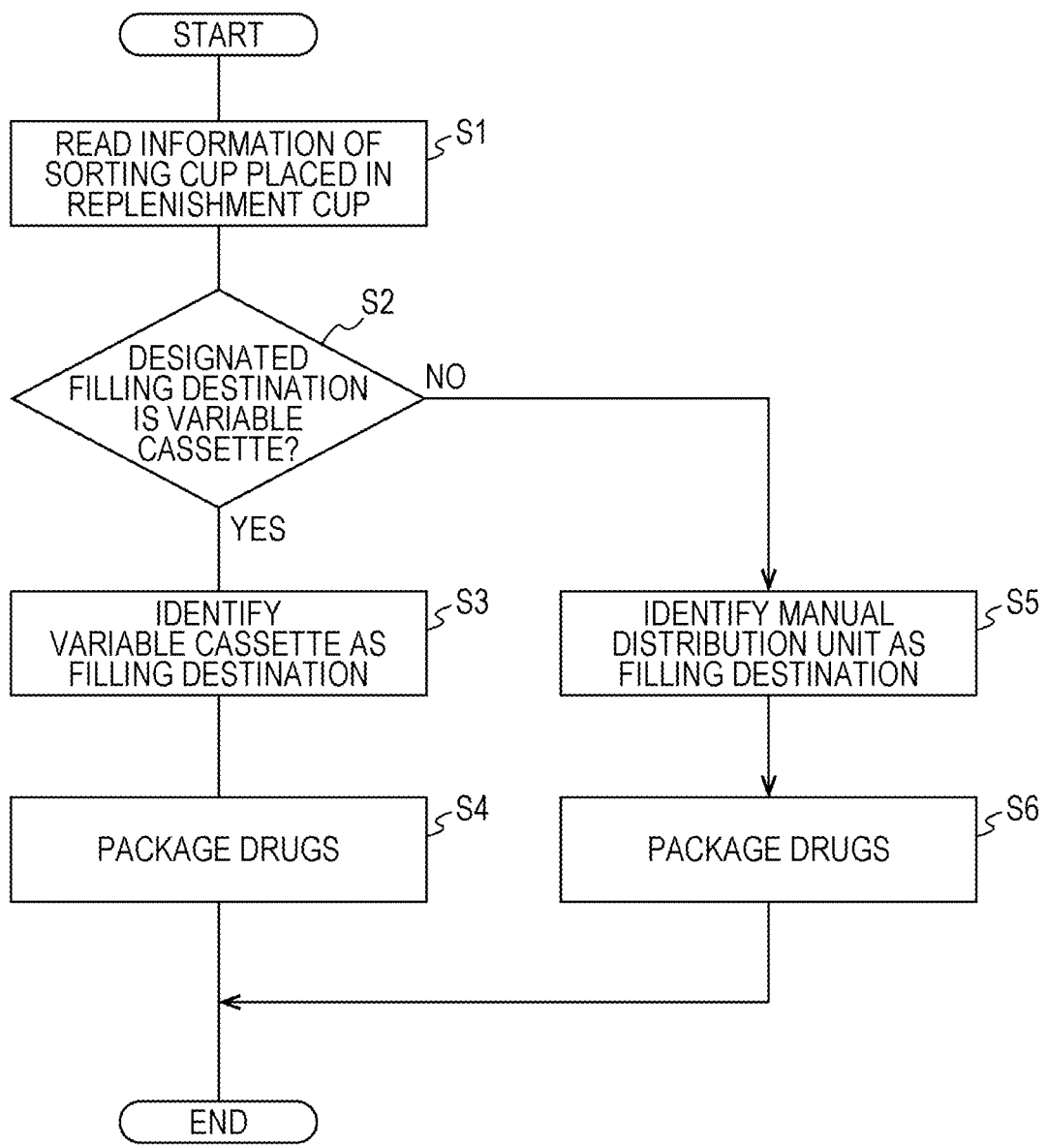
FIG. 21 is a flow chart for illustrating an example of packaging processing in the packaging machine.

Next, an example of processing performed when drugs accommodated in the sorting cup 141 are returned to a drug shelf (not shown) is described. FIG. 21 is a flow chart for illustrating an example of the packaging processing in the packaging machine 700.

The user first places the sorting cup 141 on the replenishment table 703. The RFID reader of the replenishment table 703 reads, from the RFID tag of the sorting cup 141, the identification information on the drugs accommodated in this sorting cup 141 (Step S1).

Subsequently, the control unit 706 identifies whether the designated filling destination of the drugs is the variable cassette 801 or the manual distribution unit 709 (Step S2).

In this case, information on drugs mounted to the packaging machine 700 is stored in the drug sorting device 1. Therefore, when the drug sorting device 1 determines, based on this information, that the drugs accommodated in the sorting cup 141 are not mounted to the packaging machine 700, the drug sorting device 1 designates the variable cassette 801 or the manual distribution unit 709 as the filling destination of the accommodated drugs. Then, a journal on which filling destination information (return destination information) indicating the designated filling destination is printed is issued. Which of the variable cassette 801 and the manual distribution unit 709 is to be designated may be determined, for example, for each type of the drugs.

The drug sorting device 1 also stores information regarding the variable cassette 801 that can be used in the packaging machine 700. Therefore, the drug sorting device 1 can designate the variable cassette 801 to be used for allotting the drugs accommodated in the sorting cup 141. When the user owns a plurality of packaging machines 700, the drug sorting device 1 stores information regarding the variable cassette 801 that can be used for each of the packaging machines 700.

The control unit 706 refers to, for example, the filling destination information of the journal read by the bar code reader 701 to identify the filling destination of the drugs accommodated in the sorting cup 141. At this time, the control unit 706 refers to the identification information read in Step S1 to determine suitability of the journal to be referred to.

When the designated filling destination of the drugs is the variable cassette 801 (YES in Step S2), the control unit 706 identifies the variable cassette 801 indicated in the filling destination information read from the journal, as a member for dispensing the drugs accommodated in the sorting cup 141 (Step S3). After that, the control unit 706 brings the identified variable cassette 801 to a removable state.

Subsequently, the control unit 706 notifies the user to fill the identified variable cassette 801 with the drugs. After accommodating the drugs accommodated in the sorting cup 141 into the identified variable cassette 801, the user performs, for example, a user operation for starting the packaging. Thus, the control unit 706 performs the packaging processing for the accommodated drugs (Step S4). That is, the drugs that have been accommodated in the sorting cup 141 can be dispensed from the variable cassette 801 to be packaged in order to be returned to, for example, the drug shelf.

When the designated filling destination of the drugs is the manual distribution unit 709 (NO in Step S2), the control unit 706 identifies the manual distribution unit 709 as a member for dispensing the drugs accommodated in the sorting cup 141 (Step S5). In this case, the control unit 706 determines the position of the manual distribution accommodating portion 709*a* for accommodating the drugs to be dispensed, and issues an instruction sheet that reflects a result of the determination. While viewing the instruction sheet, the user performs, for example, the user operation for starting the packaging after the drugs accommodated in the sorting cup 141 are accommodated into the manual distribution accommodating portion 709*a*. Thus, the control unit 706 performs the packaging processing for the accommodated drugs (Step S6). That is, the drugs that have been accommodated in the sorting cup 141 can be dispensed from the manual distribution unit 709 to be packaged in order to be returned to, for example, the drug shelf.

In this manner, the variable cassette 801 or the manual distribution unit 709 is identified as the filling destination of the drugs accommodated in the sorting cup 141. Then, the packaging machine 700 packages the drugs dispensed from the variable cassette 801 or the manual distribution unit 709 in order to return the drugs to the drug shelf. That is, the drugs accommodated in the sorting cup 141 is packaged on the assumption that the drugs are drugs that are not mounted to the packaging machine 700 (unmounted drug). Therefore, the user can fill the drug shelf with the drugs accommodated in the sorting cup 141 without being aware of whether or not the drugs are mounted to the packaging machine 700.

When the packaging is to be performed by the packaging mechanism 6 of the drug sorting device 1, it is required to suck the drugs accommodated in the sorting cup 141 one by one by the suction mechanism and convey the drugs to the packaging mechanism 6. When the variable cassette 801 or the manual distribution unit 709 is used, the drugs accommodated in the sorting cup 141 can be accommodated into the variable cassette 801 or the manual distribution unit 709 at a time, and can be sequentially dispensed from the variable cassette 801 or the manual distribution unit 709. Therefore, the processing time period can be shortened as compared with the case of using the packaging mechanism 6 for the packaging. In addition, the sorting cup 141 can be emptied at an early stage to be used for sorting drugs having a type different from that of drugs that have been accommodated.

There is also a case in which the packaging mechanism 6, which is an optional function of the drug sorting device 1, is not provided to the drug sorting device 1. Even in this case, the drugs accommodated in the sorting cup 141 can be packaged by the packaging machine 700.

In addition, drugs accommodated in each of a plurality of sorting cups 141, as many as the number of variable cassettes 801 that can be used, can be accommodated into each of the variable cassettes 801. In the same manner, drugs accommodated in each of a plurality of sorting cups 141, as many as the number of the manual distribution accommodating portions 709*a* of the manual distribution unit 709 that can accommodate the drugs, can be accommodated into each of the manual distribution accommodating portions 709*a*. Therefore, the drugs accommodated in each of the plurality of sorting cups 141 can be packaged at the same timing.

The processing of Step S2, Step S4, and Step S5 may be performed by the user. For example, the user may identify the filling destination of the drugs accommodated in the sorting cup 141 by viewing the journal issued by the drug sorting device 1. In this case, the control unit 706 displays the identification information read from the sorting cup 141 on the touch panel 704. Thus, the user can confirm whether or not the journal is a journal for the intended drugs.

In the above-mentioned processing, the drugs accommodated in the sorting cup 141 are not accommodated into the fixed cassette 800. However, when a vacant fixed cassette 800 capable of dispensing the accommodated drugs is mounted to the fixed cassette mounting portion 705*b* in advance, the control unit 706 may identify this fixed cassette 800 as the filling destination of the drugs accommodated in the sorting cups 141.

Other Processing in this Embodiment

Figure 22:
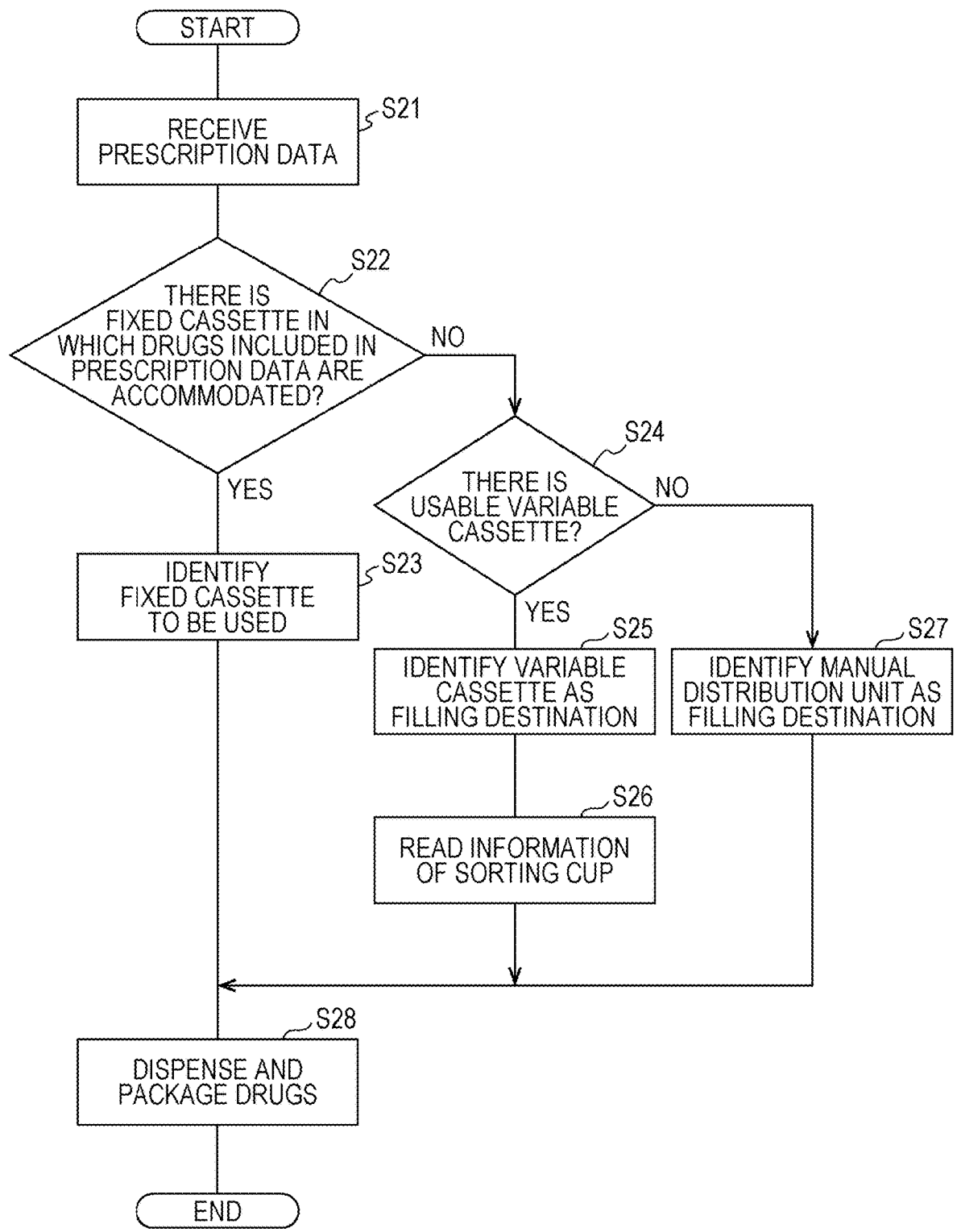
FIG. 22 is a flow chart for illustrating another example of the packaging processing in the packaging machine.

Another example of the packaging processing in the packaging machine 700 is described. FIG. 22 is a flow chart for illustrating another example of the packaging processing in the packaging machine 700.

Now, a case in which the packaging machine 700 packages drugs based on the prescription data is described. The description is given on the assumption that drugs to be dispensed are present among the drugs sorted by the drug sorting device 1 when there is no fixed cassette 800 itself for accommodating the drugs to be dispensed.

First, when the control unit 706 receives the prescription data (Step S21), the control unit 706 determines presence or absence of the fixed cassette 800 in which drugs (drugs to be dispensed) included in the prescription data are accommodated (Step S22). When the control unit 706 determines that the corresponding fixed cassette 800 is present (YES in Step S22), the control unit 706 identifies this fixed cassette 800 as a cassette for dispensing the drugs to be dispensed (Step S23).

When the control unit 706 determines that the corresponding fixed cassette 800 is not present (NO in Step S22), the control unit 706 determines whether or not there is a usable variable cassette 801 among the variable cassettes 801 owned by the user (Step S24).

When the control unit 706 determines that a usable variable cassette 801 is present (YES in Step S24), the control unit 706 identifies this variable cassette 801 as a cassette for dispensing the drugs to be dispensed (Step S25). That is, the control unit 706 allots the identification information on the drugs to be dispensed to this variable cassette 801.

In addition, the control unit 706 notifies the user to fill the identified variable cassette 801 with the drugs. The user takes out the sorting cup 141 accommodating those drugs from the drug sorting device 1, and places this sorting cup 141 on the replenishment table 703. Thus, the RFID reader of the replenishment table 703 reads the identification information stored in the RFID tag of the sorting cup 141 (Step S26). When the control unit 706 determines that the read identification information matches the identification information allotted to the identified variable cassette 801, the control unit 706 brings the variable cassette 801 to a state in which the drugs can be fed (for example, releases the lock of the variable cassette mounting portion 702). After that, the user accommodates the drugs accommodated in the sorting cup 141 into the variable cassette 801, and then performs, for example, the user operation for starting the packaging. Thus, the drugs to be dispensed can be dispensed from the variable cassette 801.

When the control unit 706 determines that the usable variable cassette 801 is not present (NO in Step S24), the control unit 706 identifies the manual distribution unit 709 as a unit for dispensing the drugs to be dispensed (Step S27). In this case, the control unit 706 determines the position of the manual distribution accommodating portion 709a accommodating the drugs to be dispensed based on the prescription data, and issues an instruction sheet that reflects a result of the determination. While viewing the instruction sheet, the user accommodates the drugs (drugs to be dispensed) accommodated in the sorting cup 141 into the manual distribution accommodating portion 709a, and then performs, for example, the user operation for starting the packaging. Thus, the drugs to be dispensed can be dispensed from the manual distribution unit 709.

The control unit 706 identifies the dispensing destination for all the drugs included in the prescription data as described above. After that, the control unit 706 dispenses the drugs from the fixed cassette 800, the variable cassette 801, and/or the manual distribution unit 709 based on the prescription data, and packages the drugs (Step S28).

When the fixed cassette 800 accommodating drugs becomes vacant, the control unit 706 may notify the user to instruct the user to accommodate those drugs into this fixed cassette 800. In this case, the user views the notification, to thereby take out the sorting cup 141 accommodating those drugs from the drug sorting device 1 and place the sorting cup 141 on the replenishment table 703. With this placement, the control unit 706 pivots all the fixed cassette mounting portions 705b so as to arrange the corresponding fixed cassette 800 on the front surface side of the packaging machine 700, and hence the user can accommodate the drugs accommodated in the sorting cup 141 into the fixed cassette 800.

In the above description, after it is determined whether or not the fixed cassette 800 can be used, it is determined whether or not the variable cassette 801 can be used, and then it is determined whether or not the manual distribution unit 709 can be used, but this disclosure is not limited thereto. The control unit 706 may identify from which of the fixed cassette 800, the variable cassette 801, and the manual distribution unit 709 to dispense drugs for each type of the drugs included in the prescription data. For example, the control unit 706 identifies the dispensing destination of the drugs based on dispensing destination information determined for each type of the drugs in advance. That is, in this case, the control unit 706 identifies the dispensing destination of the drugs, which is included in the prescription data, without determining whether or not the fixed cassette 800 and the variable cassette 801 can be used, and hence a time period for the packaging processing can be shortened as compared with the case of the processing method illustrated in FIG. 22.

Ninth Embodiment

In this embodiment, an example of the discrimination processing is described with reference to FIG. 1. As described in the first embodiment, the sorting control unit 62 determines the sorting position in the temporarily determined area Ar12 based on at least one of the color and the shape of the estimated drug and the information attached to this drug in the image. Specifically, the sorting control unit 62 determines the sorting position so that the estimated drugs regarded as matching each other in at least one of the color and the shape of the estimated drug and the information attached to this drug have the same sorting position.

A threshold value to be used for thus determining whether or not there is a match may not be a fixed value but may be a value that can be changed through user operation. That is, the threshold value for determining whether or not there is a match in terms of at least one of the color and shape of the estimated drug and the information attached to this estimated drug can be variably set, and the sorting control unit 62 may use this threshold value to perform the above-mentioned determination when the sorting position in the temporarily determined area Ar12 is to be determined.

In the temporarily determined area Ar12, criteria for the above-mentioned determination that drugs are to be accommodated into the same sorting cup 141 are different depending on the user. For example, some users wish to accommodate drugs into the same sorting cup 141 as long as the drugs are white even when the size or the shape is slightly different, and other users think that drugs cannot be accommodated into the same sorting cup 141 unless there is a match in terms of the color, the size, and the shape to a certain extent. In addition, there are some users who think that drugs cannot be accommodated into the same sorting cup 141 unless there is a match in terms of the inscribed information on the front surface and the inscribed information on the back surface to a certain extent.

It is possible to sort the drugs into the temporarily determined area Ar12 in accordance with the criteria of each user through use of the threshold value set through the user operation.

In addition, for example, the threshold value is strictly set so as not to allow a certain difference in color, shape, or another such attribute, to thereby be able to narrow down the candidates for the type of the drug as much as possible even when the type of the drug fails to be identified. Therefore, drugs having a relatively high matching degree of the feature can be accommodated into the same sorting cup 141 arranged in the temporarily determined area Ar12.

Particularly in a case of a brought drug, the brought drug is not a drug prescribed by the user, and hence a search range for identifying the type of the drug becomes wider and more enormous than that of the prescribed drug. Therefore, particularly in the case of the brought drug, the threshold value is set so that the drugs having a relatively high matching degree are accommodated into the same sorting cup 141 arranged in the temporarily determined area Ar12, to thereby be able to narrow down the above-mentioned search range in the next type identification.

In addition, even when the sorting control unit 62 cannot identify the type of the drug, the image of each drug accommodated in the sorting cup 141 is stored in association with the drug data on this drug. Therefore, it is possible to leave evidence of a drug whose type has failed to be identified. For example, the brought drug is not a drug prescribed by the user, and hence it tends to be difficult to identify the type of the brought drug. The storing of the image of the drug enables this image to be effectively utilized in, for example, the identification of the brought drug.

In addition, the number of sorting cups 141 in the temporarily determined area Ar12 is finite and small. The threshold value is set so as to allow a certain difference in color, shape, or another such attribute, to thereby be able to reduce the number of sorting cups 141 to be used in the temporarily determined area Ar12.

As the threshold value, a level (strictness) can be set for each of a plurality of determination targets. For example, when the determination target is the color, a range of chromaticity determined to match is set as the threshold value, and when the determination target is the shape, a range of the shape determined to match is set as the threshold value. It is also possible to set whether or not to use the threshold values for a plurality of determination targets. For example, when the determination targets are the color and the shape, the determination targets to be used can be selected from the color only, the shape only, or both the color and the shape.

Examples of an operation unit for adjusting the above-mentioned level include a touch type LED level bar, a dial type operation unit, a quick wheel type operation unit, and other various operation units. In addition to the color and the shape of the drug, specific examples of the above-mentioned determination target include, for example, the presence or absence of inscribed information, the position of the inscribed information, and the size of the drug. When the position of the inscribed information is set to "single side," drugs having inscribed information on a single side are extracted as candidates for drugs having the same type, and when the position of the inscribed information is set to "both sides," only drugs having inscribed information on both sides are extracted as candidates for drugs having the same type. In addition, a threshold value of the size of the drug can be set in units of 1 mm.

Tenth Embodiment

In this embodiment, a configuration for shortening a time period for the drug sorting processing is described with reference to FIG. 1. It suffices that, in the same manner as in the sixth embodiment, the drug sorting device 1 according to this embodiment has the basic configuration described in the second embodiment.

When drugs are accommodated in all the sorting cups 141, drugs having a type different from those of the drugs accommodated in all the sorting cups 141 cannot be sorted into the sorting cups 141 until there occurs a vacant sorting cup 141.

The control unit 60*a* of the drug sorting device 1 identifies the drugs accommodated in the sorting cup 141 as the objects to be packaged when a predetermined condition is satisfied irrespective of the number of drugs accommodated in the sorting cup 141. For example, the control unit 60*a* identifies the sorting cup 141 accommodating the drugs that are not mounted to the packaging machine 700 (unmounted drugs) or the sorting cup 141 selected by the user, as the sorting cup 141 accommodating the drug to be packaged. In this case, as the number of drugs identified as the objects to be packaged becomes larger, the packaging processing requires more time.

In this embodiment, the number of drugs for determining whether or not the drugs accommodated in the sorting cup 141 are to be packaged is set in advance. The control unit 60*a* identifies the sorting cup 141 in which the number of drugs accommodated in each sorting cup 141 is equal to or smaller than the number set in advance when drugs are accommodated in all the sorting cups 141. Then, the control unit 60*a* identifies the drugs accommodated in the identified sorting cup 141 as the drugs to be packaged.

Thus, the sorting cup 141 occupied by a small number of accommodated drugs can be preferentially brought to a vacant state (state that can be used for the next drug sorting). Therefore, even when drugs are accommodated in all the sorting cups 141, a vacant sorting cup 141 can be prepared in a shorter period of time, and hence the time period for the drug sorting processing can be shortened.

In addition, when drugs are accommodated in all the sorting cups 141, the user is required to operate, for example, the packaging mechanism 6 in order to empty any one of the sorting cups 141. In another example, it is required to take out this sorting cup 141 and fill the packaging machine 700 or the drug shelf with the drugs accommodated in this sorting cup 141. Those tasks can be burdensome, particularly for a user who does not wish to package drugs as much as possible.

As described above, the control unit 60*a* determines, as the objects to be packaged by the packaging mechanism 6, the drugs accommodated in the sorting cup 141 in which the number of drugs accommodated in each sorting cup 141 is equal to or smaller than the number set in advance when drugs are accommodated in all the sorting cups 141. That is, a vacant sorting cup 141 can be automatically prepared without intermediation of the user operation. Therefore, it is possible to reduce a burden on the user due to the above-mentioned task.

The same applies to the case in which the confirmed area Ar11 and the temporarily determined area Ar12 are set. That is, the control unit 60*a* identifies the sorting cup 141 in which the number of the accommodated drugs is equal to or smaller than the number set in advance when drugs are accommodated in all the sorting cups 141 in the confirmed area Ar11. Then, the control unit 60*a* may set the drugs accommodated in the identified sorting cup 141 as the objects to be packaged by the packaging mechanism 6. The same applies when drugs are accommodated in all the sorting cups 141 in the temporarily determined area Ar12.

Eleventh Embodiment

Figure 23A:
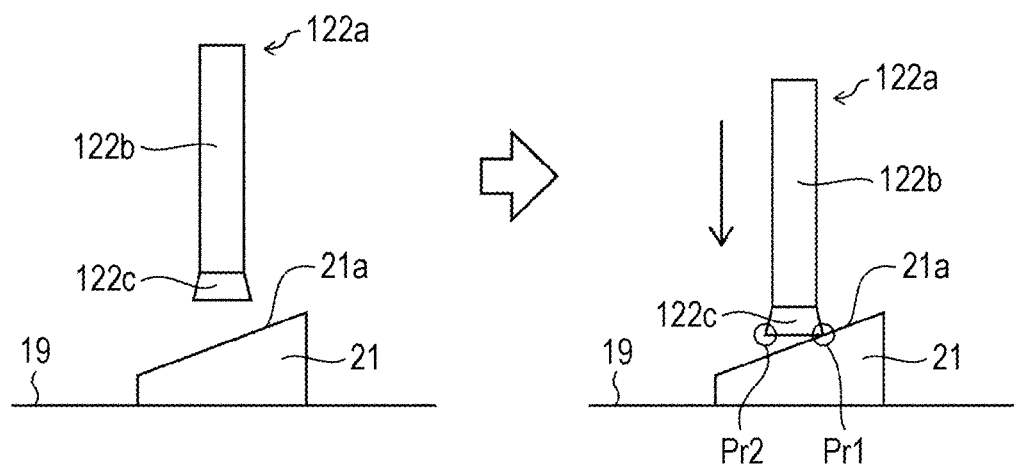
FIG. 23A and FIG. 23B are diagrams for illustrating an operation example of a suction mechanism.
Figure 23B:
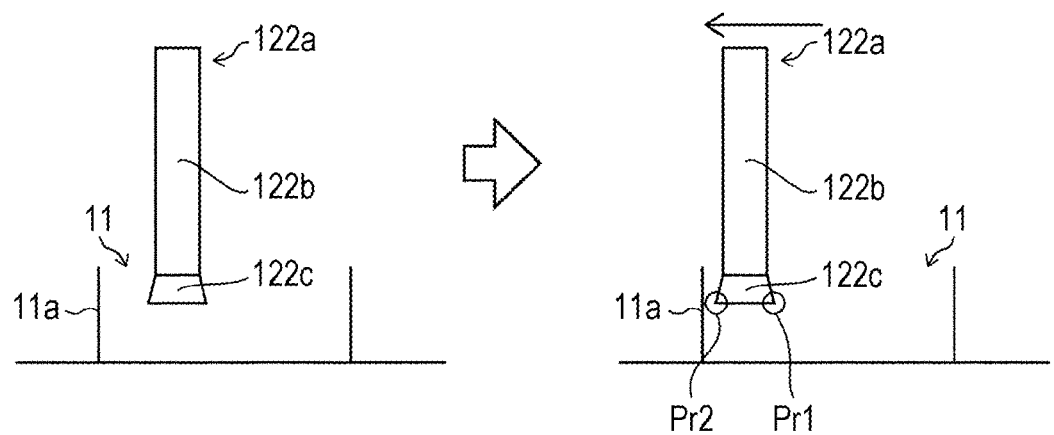

In this embodiment, a configuration for preventing a suction pad 122*c* from being forgotten to be attached is described with reference to FIG. 1 and FIGS. 23A and 23B. FIG. 23A and FIG. 23B are diagrams for illustrating an operation example of a suction mechanism 122*a*. In the same manner as in the sixth embodiment, it suffices that the drug sorting device 1 according to this embodiment has the basic configuration described in the second embodiment.

As described in the first embodiment with reference to FIG. 1 and other figures, the suction/shutter mechanism 122 includes the suction mechanism 122a for sucking a drug identified as an object to be conveyed. As illustrated in FIG. 23A, the suction mechanism 122a includes: an air pipe 122b through which air flows; and the suction pad 122c located at a tip end portion of the air pipe 122b to be brought into contact with the drug to be conveyed. The suction pad 122c is connected to a vacuum pump (not shown) configured to generate a vacuum (suck air) through the air pipe 122b through which air flows.

The suction pad 122c can be detached from the air pipe 122b for cleaning. After the cleaning, the suction pad 122c is attached to the air pipe 122b. In order to prevent the suction pad 122c from being forgotten to be attached, the conveyance control unit 61 lowers the suction mechanism from the bottom portion of the first accommodating portion 11 or the pedestal 19 (reference surface) to a predetermined height when, for example, an operation of the drug sorting device 1 is started. The predetermined height is set to such a height as to bring the suction pad 122c into contact with the reference surface with the suction pad 122c being attached.

The conveyance control unit 61 measures a flow rate in the air pipe 122b by performing suction at the predetermined height. When there is a change in flow rate, it is determined that the suction pad 122c is attached, and when there is no change in flow rate, it is determined that the suction pad 122c is not attached.

However, when the above-mentioned method is used to determine whether or not the suction pad 122c is attached, it is required to strictly define the predetermined height and the size of the suction pad 122c for each drug sorting device 1. Therefore, it requires time and labor to adjust the predetermined height and measure the size of the suction pad 122c for each drug sorting device 1. There is also a possibility that erroneous determination may be caused due to an individual difference of the suction pad 122c.

In this embodiment, a position of a tip surface of the suction mechanism 122a, to which the suction pad 122c is attached, with respect to a reference surface is defined such that, when this tip surface is brought close to this reference surface, distances between this reference surface and at least two spots on this tip surface are different from each other.

Specifically, as illustrated in FIG. 23A, the pedestal 19 is provided with a sloped pedestal 21. The sloped pedestal 21 has a sloped surface 21a that is sloped with respect to the tip surface of the suction mechanism 122a (bottom surface of the suction pad 122c when the suction pad 122c is attached). The sloped surface 21a corresponds to the above-mentioned reference surface.

Consideration is given to a case in which the suction mechanism 122a is brought close to a predetermined height from the sloped surface 21a to perform the suction. The predetermined height is defined at such a position as to bring a part of the suction pad 122c (here, a first portion Pr1) into contact with the suction pad 122c when the suction pad 122c is attached.

When the suction pad 122c is attached, there occurs almost no gap between the first portion Pr1 and the sloped surface 21a, and hence the change in flow rate at the first portion Pr1 becomes larger. Therefore, in this case, the conveyance control unit 61 can determine that the change in flow rate has become equal to or higher than the threshold value (the flow rate has become lower than the threshold value), and can determine that the suction pad 122c is attached.

Amounts of change in flow rate at the positions on the suction pad 122c differ depending on the distances between those positions and the sloped surface 21a. A shape of the suction pad 122c changes due to this difference in amount of change in flow rate. Specifically, the shape of the suction pad 122c changes so that as the above-mentioned distance becomes shorter, the change in flow rate at the suction pad 122c becomes larger (for example, the change in flow rate becomes larger at the first portion Pr1 than at a second portion Pr2). Therefore, the flow rate at the first portion Pr1 is likely to change more significantly than the flow rate at the second portion Pr2.

However, even when the shape of the suction pad 122c changes, the suction pad 122c sucks onto the sloped surface 21a. Therefore, the conveyance control unit 61 can determine whether or not the suction pad 122c is attached based on the change in flow rate even when the sloped pedestal 21 is used.

Meanwhile, when the suction pad 122c is not attached, a gap occurs between the first portion Pr1 and the sloped surface 21a by a thickness of the suction pad 122c, and there occurs almost no change in flow rate even at the first portion Pr1. Therefore, the conveyance control unit 61 can determine that the change in flow rate is lower than the threshold value (the flow rate remains equal to or higher than the threshold value), and can determine that the suction pad 122c is not attached.

In another case, as illustrated in FIG. 23B, it may be determined whether or not the suction pad 122c is attached by bringing the suction mechanism 122a close to a wall surface 11a of the first accommodating portion 11. In this case, the wall surface 11a corresponds to the above-mentioned reference surface.

Consideration is given to a case in which the suction mechanism 122a performs the sucking after being lowered into the first accommodating portion 11 and then brought close to a position a predetermined distance apart from the wall surface 11a. The predetermined distance is defined at such a position as to bring a part of the suction pad 122c (here, the second portion Pr2) into contact with the suction pad 122c when the suction pad 122c is attached.

When the suction pad 122c is attached, there occurs almost no gap between the second portion Pr2 and the wall surface 11a, and hence the change in flow rate at the second portion Pr2 becomes larger. Therefore, in this case, the conveyance control unit 61 can determine that the change in flow rate has become equal to or higher than the threshold value, and can determine that the suction pad 122c is attached. In the same manner as described above, the amount of change in flow rate at the suction pad 122c differs depending on the distances between the positions on the suction pad 122c and the wall surface 11a, to thereby change the shape of the suction pad 122c. Ascribable to this, the flow rate of the second portion Pr2 is likely to change more significantly than the flow rate at the first portion Pr1.

Meanwhile, when the suction pad 122c is not attached, the flow rate does not change at least due to the change in shape of the suction pad 122c. Thus, even when there occurs a change in flow rate, the change is smaller than when the suction pad 122c is attached. Therefore, the conveyance control unit 61 can determine that the change in flow rate is lower than the threshold value, and can determine that the suction pad 122c is not attached.

With the above-mentioned configuration, it is not required to strictly define a moving distance of the suction mechanism 122a to the sloped surface 21a or the wall surface 11a. This is because when the suction pad 122c is attached, the change in flow rate becomes larger due to the change in shape of the suction pad 122c. Therefore, it is possible to reduce the time and labor required for strictly defining the above-mentioned moving distance.

It is also possible to set the predetermined height or the predetermined distance at a position slightly apart from a contact position between the reference surface and the suction pad 122c. It is also expected that suction pads 122c having various shapes or sizes are used together due to, for example, the individual difference of the suction pads 122c and a design change of the suction pads 122c. The predetermined height or the predetermined distance are set as described above, and hence the conveyance control unit 61 can stably detect whether or not the suction pad 122c is attached irrespective of the suction pads 122c having various shapes or sizes.

Twelfth Embodiment

Figure 24A:
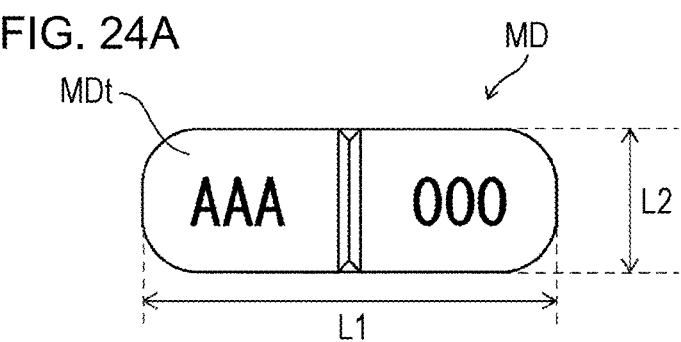
Figure 24B:
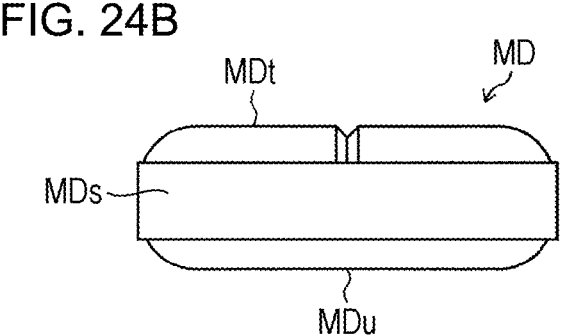

In this embodiment, a configuration for accurately discriminating the type of a drug having a predetermined shape is described with reference to FIG. 1, FIGS. 3A to 3C, FIGS. 4A and 4B, FIGS. 14A to 14C, and FIGS. 24A and 24B. FIGS. 24A and 24B are views for illustrating an example of a drug having an elongated shape, in which FIG. 24A is a plan view, and FIG. 24B is a side view. In the same manner as in the sixth embodiment, it suffices that the drug sorting device 1 according to this embodiment has the basic configuration described in the second embodiment.

As described in the first embodiment, the swiveling mechanism 133b illustrated in FIG. 3A and FIG. 3B can vibrate the drug loading stage 133a. The swiveling mechanism 133b vibrates the drug loading stage 133a, to thereby be able to orient the inscribed information or the printed information in a predetermined direction (for example, upward (+Z-axis direction)). In addition, the drug loading stage 133a is vibrated, to thereby be able to move the drug that is not present in a central vicinity to substantially the center on the drug loading stage 133a. When the drug is a tablet, as illustrated in FIG. 14B, the swiveling mechanism 133b rotates the shaft portion 133c so as to bring the slope surface portions 133ab of the drug loading stage 133a to a substantially horizontal state.

Then, as illustrated in FIG. 4A and FIG. 4B, the swiveling mechanism 133b pivots the image pick-up mechanism including the first camera 131 and the illumination device 134 so as to swivel the swiveling mechanism 133b around the arrangement area Ar2. Thus, the first camera 131 can pick up an image of the drug placed on the drug loading stage 133a from four spots, for example, θ=0°, 45°, 135°, and 180° in the arrangement area Ar2.

However, depending on the shape of the drug, when the drug is to be moved to substantially the center by the vibration of the swiveling mechanism 133b, the inscribed information or the printed information may be adversely oriented in a direction other than the predetermined direction (unintended direction) due to the above-mentioned vibration. For example, in a case of a drug MD (for example, Sotacor (trademark)) illustrated in FIG. 24A and FIG. 24B, there is a possibility that the inscribed information ("AAA 000" in FIG. 24A) may be adversely oriented in an unintended direction.

In the drug MD, the inscribed information is attached to an upper surface MDt, and no inscribed information is attached to a side surface MDs. Further, not only the upper surface MDt or a lower surface MDu but also the side surface MDs has a flat shape having an area equal to or larger than a predetermined area. Therefore, no matter which of the upper surface MDt, the lower surface MDu, and the side surface MDs is opposed to the bottom portion of the drug loading stage 133a, the drug adversely ends up standing up. Drugs having such a shape often have such an elongated shape as illustrated in FIG. 24A and FIG. 24B.

When the drug stands up by having the side surface MDs opposed to the bottom portion of the drug loading stage 133a, the inscribed information is adversely oriented in a lateral direction (direction substantially perpendicular to the Z-axis direction). The first camera 131 picks up images from predetermined positions (for example, the above-mentioned four spots), and hence there is a possibility that such an image as to allow the inscribed information to be identified may fail to be picked up depending on the orientation.

In the drug sorting device 1 according to this embodiment, the swiveling mechanism 133b changes a rotation speed of the shaft portion 133c for changing the magnitude of vibration to be supplied to the drug loading stage 133a and a tilt angle of the slope surface portions 133ab based on the shape of the drug.

Specifically, the discriminating unit 64 acquires a long side length L1 and a short side length L2 of the drug by analyzing the picked-up image, and calculates an aspect ratio of the drug. The discriminating unit 64 determines, based on the aspect ratio of this drug, whether a ratio of the long side length L1 to the short side length L2 ((long side length L1)/(short side length L2)) is equal to or higher than the predetermined value. The predetermined value may be set to such a size as to enable detection of the drug standing up with the side surface MDs oriented downward through, for example, an experiment.

When the discriminating unit 64 determines that the ratio of the long side length L1 to the short side length L2 is equal to or higher than the predetermined value (that is, when determining that the drug stands up with the side surface MDs oriented downward), the magnitude of vibration and the rotation speed that are described above are set based on setting values to be applied when the ratio is equal to or higher than the predetermined value. The image pick-up control unit 63 controls the swiveling mechanism 133b to vibrate and rotate the drug loading stage 133a at the magnitude of vibration and rotation speed that are set in accordance with the setting values.

For example, as the above-mentioned setting values, the vibration and the rotation speed are set smaller than the setting values to be applied when the ratio of the long side length L1 to the short side length L2 is lower than the predetermined value. The vibration is set to, for example, zero.

In this manner, when the ratio of the long side length L1 to the short side length L2 is equal to or higher than the predetermined value, the drug loading stage 133a can be moved so as to prevent the drug that stands up with the side surface MDs oriented downward from standing up on the drug loading stage 133a by reducing both the vibration and the rotation speed. Therefore, it is possible to prevent the inscribed information from being oriented in a direction other than the predetermined direction by the movement of the drug loading stage 133a, and hence it is possible to accurately discriminate the type of the drug (identify the drug).

In addition, it is possible to prevent the drug from standing up with the side surface MDs oriented downward. Therefore, it is possible to prevent the image pick-up of the drug and the discrimination of the type from being performed again due to an occurrence of the above-mentioned state. Therefore, it is possible to efficiently discriminate and sort drugs.

Thirteenth Embodiment

Figure 25A:
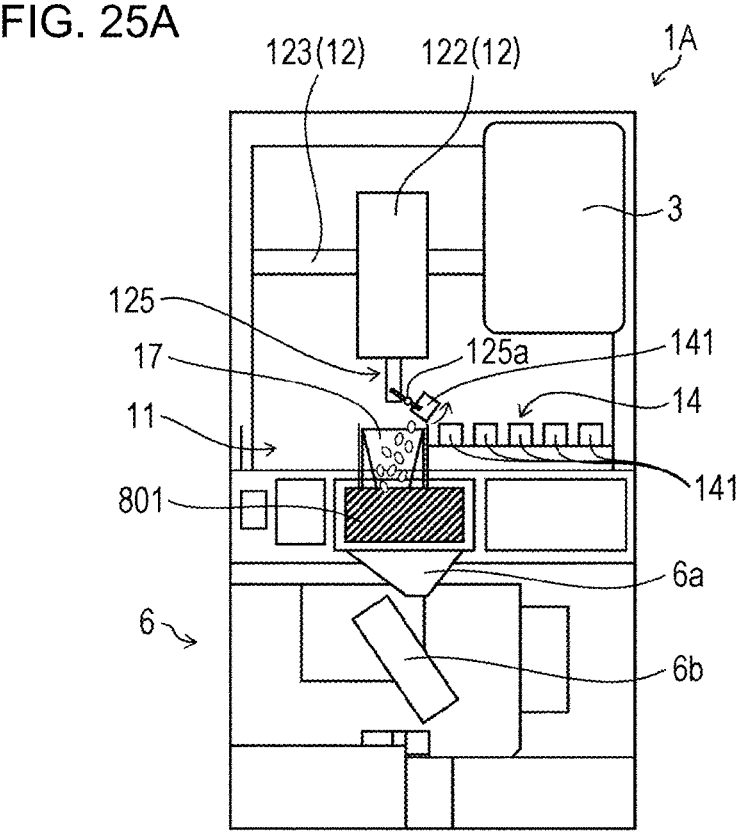
FIG. 25A is a view for illustrating a configuration example of a drug sorting device serving as a modification example of this disclosure.
Figure 25B:
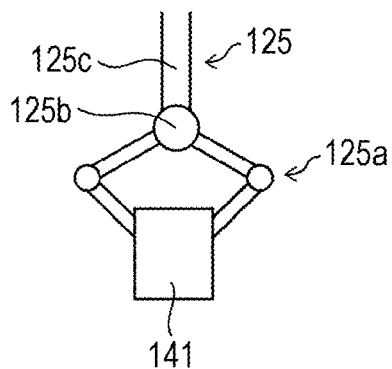
FIG. 25B and FIG. 25C are views for illustrating a shape and an operation of a tip end portion of a sorting cup conveying mechanism.
Figure 25C:
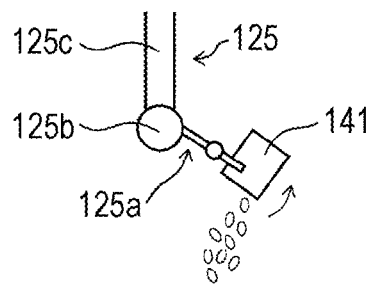

In this embodiment, a configuration for shortening the time period for the packaging processing is described with reference to FIG. 1, FIGS. 20A and 20B, and FIGS. 25A to 25C. FIG. 25A is a view for illustrating a configuration example of a drug sorting device 1A serving as a modification example, and FIG. 25B and FIG. 25C are views for illustrating a shape and an operation of a tip end portion of a sorting cup conveying mechanism 125.

The drug sorting device 1A differs from the drug sorting device 1 in that the drug sorting device 1A includes the sorting cup conveying mechanism 125 and the variable cassette 801 as illustrated in FIG. 25A. That is, the drug sorting device 1A has the same configuration and the same functions as those of the drug sorting device 1 except for the components of the sorting cup conveying mechanism 125 and the variable cassette 801. It suffices that the drug sorting device 1A has at least the basic configuration described in the second embodiment.

The drug sorting device 1A includes the packaging mechanism 6. The packaging mechanism 6 includes a package hopper 6a configured to temporarily hold this drug and a heater roller 6b configured to thermally fuse a packaging paper sheet for packaging this drug. The drug dispensed from the variable cassette 801 is transferred to the heater roller 6b through the package hopper 6a, and is packaged into the packaging paper sheet by the heater roller 6b.

The drug sorting device 1A also includes the variable cassette 801 illustrated in FIG. 20A. The variable cassette 801 is configured to dispense, one by one, drugs fed into the drug feeding port 17. The variable cassette 801 is installed below the drug feeding port 17 so that the drugs fed from the drug feeding port 17 can be received by the first rotating body 8011. The variable cassette 801 is also installed above the package hopper 6a so that the package hopper 6a can receive the drugs dispensed from the dispensing port 8015 by the second rotating body 8012. The drug sorting device 1A includes a variable cassette mounting portion (not shown) configured to mount and drive the variable cassette 801.

The suction/shutter mechanism 122 includes a suction mechanism (for example, suction mechanism 122a of FIGS. 23A and 23B) and the sorting cup conveying mechanism 125 illustrated in FIG. 25A. Both the suction mechanism and the sorting cup conveying mechanism 125 can move in the ±Z-axis direction. The suction mechanism is configured to suck a drug identified as an object to be conveyed. Therefore, the conveyance control unit 61 or the sorting control unit 62 controls the movement of the suction mechanism in the ±Z-axis direction when a drug is to be conveyed. Meanwhile, the sorting cup conveying mechanism 125 is configured to move the sorting cup 141 between the second accommodating portion 14 and the drug feeding port 17. Therefore, the sorting control unit 62 controls the movement of the sorting cup conveying mechanism 125 in the ±Z-axis direction when drugs are to be packaged by the packaging mechanism 6.

As illustrated in FIG. 25B, the sorting cup conveying mechanism 125 includes, for example, a grip portion 125a, a pivoting unit 125b, and a support portion 125c. The grip portion 125a is configured to grip the sorting cup 141. In the example of FIG. 25B, the grip portion 125a is achieved by two claw portions capable of performing an opening and closing operation. The pivoting unit 125b includes a rotary shaft extending in a direction substantially perpendicular to the Z-axis direction, and is configured to pivot the grip portion 125a. The support portion 125c is configured to support the grip portion 125a at a tip end portion of the support portion 125c.

When the drugs accommodated in the sorting cup 141 are to be packaged by the packaging mechanism 6, the sorting control unit 62 controls the conveying mechanism 123 to move to the sorting cup conveying mechanism 125 to a position above the sorting cup 141 accommodating the drugs to be packaged. After that, the sorting control unit 62 moves the sorting cup conveying mechanism 125 downward to cause the grip portion 125a to grip the sorting cup 141.

The sorting control unit 62 moves the sorting cup conveying mechanism 125 to the position above the drug feeding port 17 while the grip portion 125a is gripping the sorting cup 141, and then drives the pivoting unit 125b to pivot the grip portion 125a upward. Thus, the drugs accommodated in the sorting cup 141 can be fed into the drug feeding port 17.

Before the drugs is fed into the variable cassette 801, the control unit 60a drives the height regulating body 8013 and the width regulating body 8014 to adjust the transfer height of h1 and the transfer width of w1 based on the size of each of those drugs. Then, for example, when the drugs are fed into the variable cassette 801, the control unit 60a rotates the first rotating body 8011 and the second rotating body 8012 to dispense the fed drugs to the package hopper 6a one by one. Thus, those drugs can be packaged by the packaging mechanism 6.

When the drugs accommodated in the sorting cup 141 are to be dispensed to the packaging mechanism 6 through use of the suction mechanism, it is required to suck the drugs accommodated in the sorting cup 141 one by one and convey each drug to the drug feeding port 17. Therefore, as the number of those drugs becomes larger, it requires more time to dispense those drugs. It also required much time to prepare a vacant sorting cup 141.

When the variable cassette 801 is enabled to be mounted below the drug feeding port 17 as in the drug sorting device 1A, the drugs accommodated in the sorting cup 141 can be fed into the variable cassette 801 at a time. Therefore, even when drugs are accommodated in all the sorting cups 141, a vacant sorting cup 141 can be prepared in a short period of time for the next sorting of drugs, and hence the time period for the drug sorting processing can be shortened. It is also possible to shorten the time period for the packaging processing.

In addition, the drug sorting device 1A is provided with the sorting cup conveying mechanism 125, to thereby be able to automatically dispense the drugs accommodated in the sorting cup 141 to the packaging mechanism 6. Therefore, when the packaging mechanism 6 is to be used for the packaging, it is possible to reduce such a labor that the user carries the sorting cup 141 to the drug feeding port 17 and feed the drugs accommodated in this sorting cup 141 into the drug feeding port 17.

The sorting cup conveying mechanism 125 has been described as being provided with the conveying/sorting unit 12, but this disclosure is not limited thereto, and the sorting cup conveying mechanism 125 may be provided to the drug sorting device 1 separately from the conveying/sorting unit 12.

Fourteenth Embodiment

In this embodiment, a configuration for improving accuracy of the discrimination processing is described with reference to FIG. 1. In the same manner as in the sixth embodiment, it suffices that the drug sorting device 1 according to this embodiment has the basic configuration described in the second embodiment.

Among adopted drugs adopted in a prescription, there are drugs that are similar in color and size of the drug even when the drugs have different types. For example, there are some users for which about 70% to 80% of the adopted drugs are white tablets having a predetermined size (for example, diameter of 7 mm).

When the discriminating unit 64 is to discriminate the type of a drug accommodated in the first accommodating portion 11, the discriminating unit 64 compares the feature of the drug extracted from the image picked up by the first camera 131 with a plurality of pieces of drug data registered in the drug database. For example, the discriminating unit 64 calculates the matching degree between the feature of the drug and each piece of drug data as a score, and ranks the pieces of drug data in descending order of this score. Then, the discriminating unit 64 identifies the pieces of drug data up to a set rank (for example, pieces of drug data in the first rank to the tenth rank) as a candidate (data candidate) for the drug data to be used for identifying the type of the drug.

When the size, the color, or another such attribute of the drug accommodated in the drug sorting device 1 differs depending on the type, the score of the piece of drug data in the first rank is often more prominent than the score of the piece of drug data in the second rank or a lower rank. Therefore, in this case, the discriminating unit 64 can sufficiently identify the type of the drug by identifying, as data candidates, the pieces of drug data up to the rank (for example, the tenth rank) set as described above.

However, when the data candidates are identified as described above, there is a possibility that the types of drugs that are different in type but similar in size and color cannot be accurately identified. That is, when there are a large number of drugs having similar sizes and colors, there is a possibility that the scores may be similar even in ranks lower than the set rank (when the set rank is tenth, the eleventh rank or higher ranks). Therefore, there is a possibility that drug data supposed to be properly subjected to the identification is present in the above-mentioned lower ranks.

In view of this, in order to accurately identify such a type of the drug, as a result of comparing the feature of the drug extracted from the image with the registered drug data, the discriminating unit 64 identifies, as data candidates, the drug data having the matching degree with this feature being equal to or higher than a predetermined value. Then, the discriminating unit 64 discriminates the type of the drug by comparing this feature of the drug extracted from the image of the drug picked up again with each of those data candidates.

For example, the discriminating unit 64 calculates the matching degree (score) with the feature of the drug extracted from the image for each piece of drug data included in the drug database to identify the piece of drug data having a first-ranked score. The discriminating unit 64 identifies, as data candidates, all the pieces of drug data within a range of a preset difference value from the score of the piece of drug data in the first rank. Then, for example, the discriminating unit 64 sets a flag for each piece of drug data identified as a data candidate.

For example, it is assumed that the score is defined as 0 to 100 (as the numerical value becomes larger, the matching degree becomes higher). For example, when the score of the piece of drug data in the first rank is 97.5 and the preset difference value is 0.3, the discriminating unit 64 identifies, as data candidates, all the pieces of drug data having a score equal to or higher than 97.2 (=97.5−0.3).

After that, the first camera 131 picks up an image of the drug again, and the discriminating unit 64 calculates the scores by comparing the feature of the drug included in the picked-up image with the identified data candidates. Then, the data candidates having the scores within the range of the preset difference value are further identified as data candidates.

The discriminating unit 64 uniquely identifies the drug data by repeating the above-mentioned processing. The determination of whether or not to pick up an image of the drug again may be performed (number of times of the image pick-up may be determined) depending on, for example, the number of identified data candidates.

In this manner, the pieces of drug data having the scores equal to or higher than the predetermined value are narrowed down as data candidates, to thereby be able to identify the drug data supposed to be extracted without exception. Therefore, it is possible to accurately identify the type of the drug.

When the image of the same drug is repeatedly picked up, the position of the drug may be different every time the image is picked up. When the drug is picked up at a position different from a position at a time of the previous image pick-up, image pick-up conditions may be more satisfactory than image pick-up conditions at the time of the previous image pick-up. Therefore, there is a possibility that the score can be accurately calculated by repeatedly picking up the image of the same drug.

The discriminating unit 64 may also execute, as follows, the iterative processing for comparing the feature of the drug included in the image with each data candidate in order to uniquely identify the drug data.

For example, in the first comparison, the discriminating unit 64 calculates the scores for all the data candidates by comparing the feature of the drug included in the image with all the identified data candidates. The discriminating unit 64 identifies the data candidates having the higher scores among the calculated scores (for example, data candidates within the higher 75% (that is, pieces of drug data having the scores equal to or higher than the predetermined value)) as data candidates to be comparison targets in the second iteration. Thus, the data candidates having the lower scores (for example, data candidates within the lower 25%) can be excluded from the data candidates to be the comparison targets in the second iteration. In the same manner, the discriminating unit 64 identifies the data candidates having the higher scores among the scores calculated in the second comparison (for example, data candidates within the higher 75%) as data candidates to be comparison targets in the third iteration.

For example, when the feature of the drug included in the image is inscribed information, every time the comparison is performed, the discriminating unit 64 identifies pieces of drug data having inscribed information having the matching degree with the inscribed information on the drug included in the image being equal to or higher than the predetermined value (for example, matching degree equal to or higher than 75%) as data candidates to be the next comparison targets.

In this manner, it is possible to efficiently identify the drug data by performing the comparison while reducing a certain number of data candidates to be the comparison targets to uniquely identify the drug data. The above-mentioned 75% is merely an example, and it suffices that the value is set to such an extent that the drug data can be efficiently identified through, for example, an experiment.

Fifteenth Embodiment

In this embodiment, another example of the packaging processing is described with reference to FIG. 1. It suffices that the drug sorting device 1 according to this embodiment includes the packaging mechanism 6 in addition to the basic configuration described in the second embodiment.

There may occur a hasty change in packaged content due to a change in prescription caused after drugs have been packaged based on the prescription data by, for example, the packaging machine 700. For example, when there occurs such a change in prescription as to remove drugs of one type, the user can perform a task of tearing each drug package, removing each drug of this type from each drug package, and then resealing each drug package with adhesive tape or by another such method. When the number of drug packages is small, such manual re-packaging can be performed by the user, but when the number of drug packages increases, this manual re-packaging becomes difficult in reality. Therefore, when the number of drug packages to be re-packaged increases, in an actual case, all the drug packages may be discarded, and the re-packaging may be performed based on modified prescription data by, for example, the packaging machine 700.

In this embodiment, the drug sorting device 1 may cause the packaging mechanism 6 to perform the packaging processing based on the prescription data. For example, when there occurs a change in prescription after the packaging processing for drugs based on the prescription data, the user feeds the drugs accommodated in each drug package into the first accommodating portion 11. The drug sorting device 1 sorts the drugs accommodated in the first accommodating portion 11 into the sorting cups 141 of the second accommodating portion 14 by type. After the sorting by type is completed, the drug sorting device 1 causes the packaging mechanism 6 to package the drugs sorted into the second accommodating portion 14, based on the modified prescription data (prescription data that reflects the above-mentioned changes).

In this manner, the drug sorting device 1 can perform the re-packaging corresponding to the changed content when there occurs a change in prescription. Therefore, when such a change in prescription as to remove drugs of one type occurs, it is possible to save the labor of performing a manual task of removing each drug of this type from each drug package and then sealing the drug packages with adhesive tape or by another such method. In addition, all the drug packages can be re-packaged without being discarded.

The drug sorting device 1 is not always required to sort drugs into the second accommodating portion 14 by type. For example, the drug sorting device 1 may accommodate the drugs to be re-packaged into the same drug package in the same sorting cup 141 based on the modified prescription data. In this case, in the same manner as described above, the drug sorting device 1 sorts the drugs into the second accommodating portion 14, and then the sorted drugs are packaged by the packaging mechanism 6 based on the modified prescription data.

In this case, for example, in the drug sorting device 1A described in the thirteenth embodiment (FIGS. 25A to 25C), the sorting cup 141 can be conveyed to the drug feeding port 17 as described above. That is, in the drug sorting device 1A, the drugs accommodated in one sorting cup 141 can be fed into the drug feeding port 17 at a time. Therefore, when the drugs to be re-packaged into the same drug package are accommodated in the same sorting cup 141, the drugs corresponding to one drug package can be fed into the packaging mechanism 6 at a time, and hence the packaging processing can be performed more efficiently.

The above description is given by taking an exemplary case in which the packaging mechanism 6 of the drug sorting device 1 is used for the packaging processing based on the modified prescription data, but this disclosure is not limited thereto, and the packaging mechanism 6 of the drug sorting device 1 may be used for the packaging processing for a preparatory dispensing operation. That is, when there occurs a change in content of preparatory dispensing operation data after the drugs are accommodated into each drug package (strip package) based on the preparatory dispensing operation data by, for example, the packaging machine 700, the drug sorting device 1 may perform the packaging processing based on the modified preparatory dispensing operation data in the same manner as the packaging processing based on the modified prescription data. The preparatory dispensing operation data is data created for a preparatory dispensing operation, and is data relating to a method of accommodating drugs into each strip package.

The above description is also given by taking an exemplary case in which there occurs such a change in prescription as to remove drugs, but it is conceivable that there may occur such a change in prescription as to add drugs. In this case, the user accommodates the drugs to be added into the sorting cup 141, and arranges this sorting cup 141 in the second accommodating portion 14. Thus, even when there occurs such a change in prescription as to add drugs, the drug sorting device 1 can cause the packaging mechanism 6 to re-package the drugs based on the modified prescription data.

[Supplement]

As described above, the second accommodating portion 14 accommodates drugs for each type. The expression that drugs are accommodated into the second accommodating portion 14 for each type includes a meaning that, when the type of the drug can be uniquely (completely) identified, drugs are accommodated into the same position (in the same sorting cup 141) for each uniquely identified type. In addition, the above-mentioned expression includes a meaning that, when the type of the drug has failed to be uniquely identified but drugs (estimated drugs) have been successfully identified as having features similar to each other to some extent based on, for example, the color and the shape, drugs are accommodated into the same position in units of drugs having similar features to some extent.

Sixteenth Embodiment

In this embodiment, an operation at a time of activation of the drug sorting device 1 is described. The drug sorting device 1 according to this embodiment has at least the basic configuration described in the second embodiment. The same applies to the subsequent embodiments.

<Control Unit>

Figure 26:
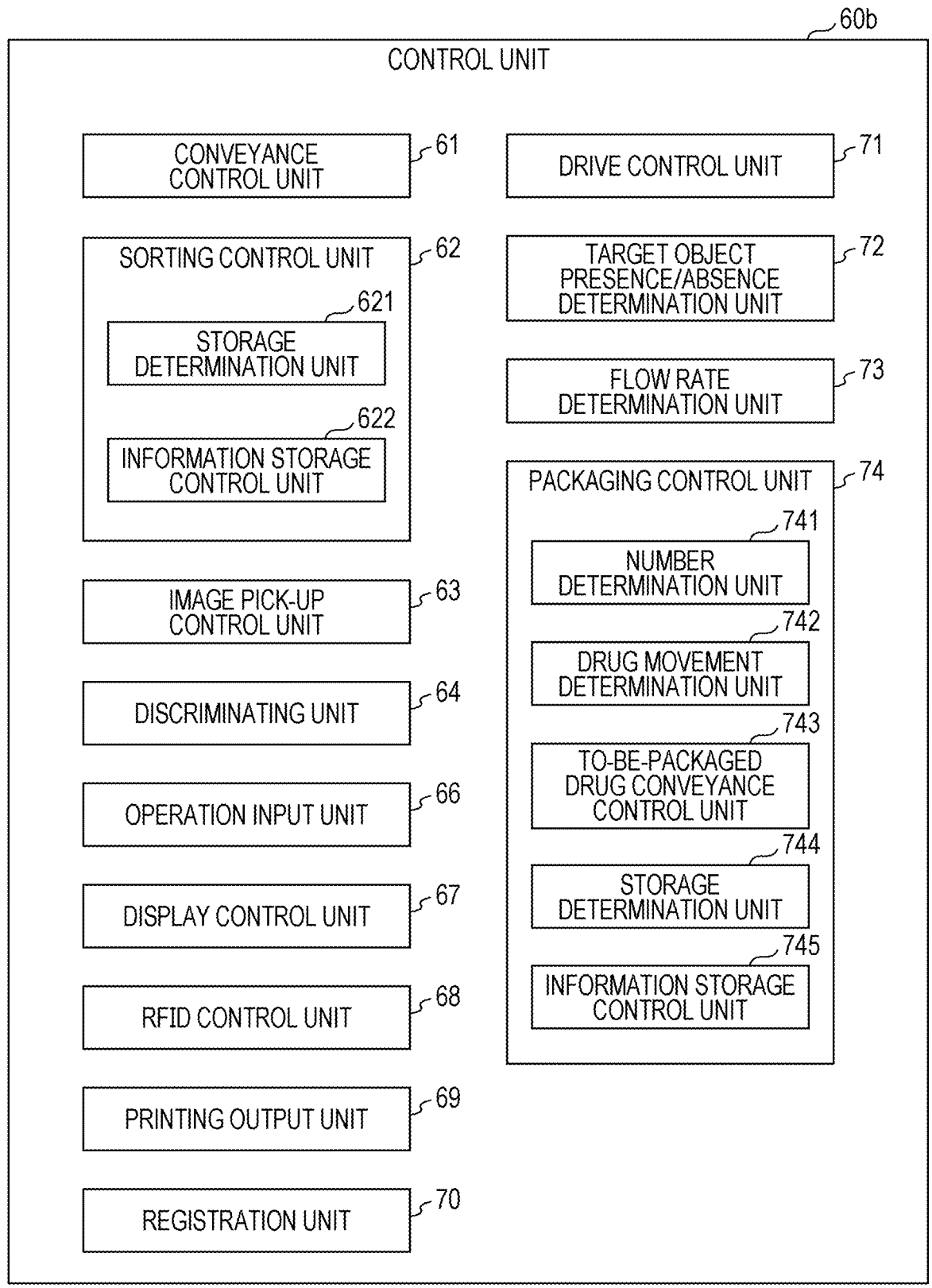
FIG. 26 is a block diagram for illustrating an example of a control unit.

First, a control unit 60b is described with reference to FIG. 26. FIG. 26 is a block diagram for illustrating an example of the control unit 60b. As illustrated in FIG. 26, in addition to the components of the control unit 60a, the control unit 60b includes a drive control unit 71, a target object presence/absence determination unit 72, a flow rate determination unit 73, and a packaging control unit 74. In each of this embodiment and the subsequent embodiments, it suffices that a control unit has the control unit 60a as its basic configuration and includes at least one of the above-mentioned members required for an operation and processing in each embodiment.

The drive control unit 71 is configured to control movement of a casing (hereinafter referred to as "drug conveying unit 120") including the second camera 121 and the suction/shutter mechanism 122 and movement of an obstacle detecting mechanism 22. Specifically, the drive control unit 71 moves the obstacle detecting mechanism 22 in conjunction with the movement of the drug conveying unit 120.

The target object presence/absence determination unit 72 is configured to determine whether or not there is a target object to be installed on the pedestal 19. Examples of a target object to be determined include a sorting cup base 14*a* (see FIGS. 27A and 27B), the standby tray 15 (see FIGS. 27A and 27B), the collection tray 16 (see FIGS. 27A and 27B), and the suction pad 122*c* (see FIGS. 23A and 23B and FIG. 31).

The flow rate determination unit 73 is configured to determine whether or not the flow rate in the suction mechanism 122*a* (see FIGS. 23A and 23B and FIG. 31) is equal to or lower than a predetermined value, to thereby determine whether or not damage (abnormal suction) has occurred in the suction mechanism 122*a*.

The packaging control unit 74 is configured to control an operation of the packaging mechanism 6. The packaging control unit 74 is also configured to control an operation of the drug conveying unit 120 configured to convey the drug stored in the sorting cup 141 to the drug feeding port 17 (drug feeding portion) or to return the drug fed into the drug feeding port 17 to the sorting cup 141.

It is to be understood that, throughout herein, the "packaging" used at least in the description of the drug sorting device 1 includes a meaning of "packaging drugs separately for each timing of administration based on prescription data" and a meaning of "simply packaging drugs sorted into the second accommodating portion 14 irrespective of prescription data."

<Obstacle Detecting Mechanism>

Figure 27A:
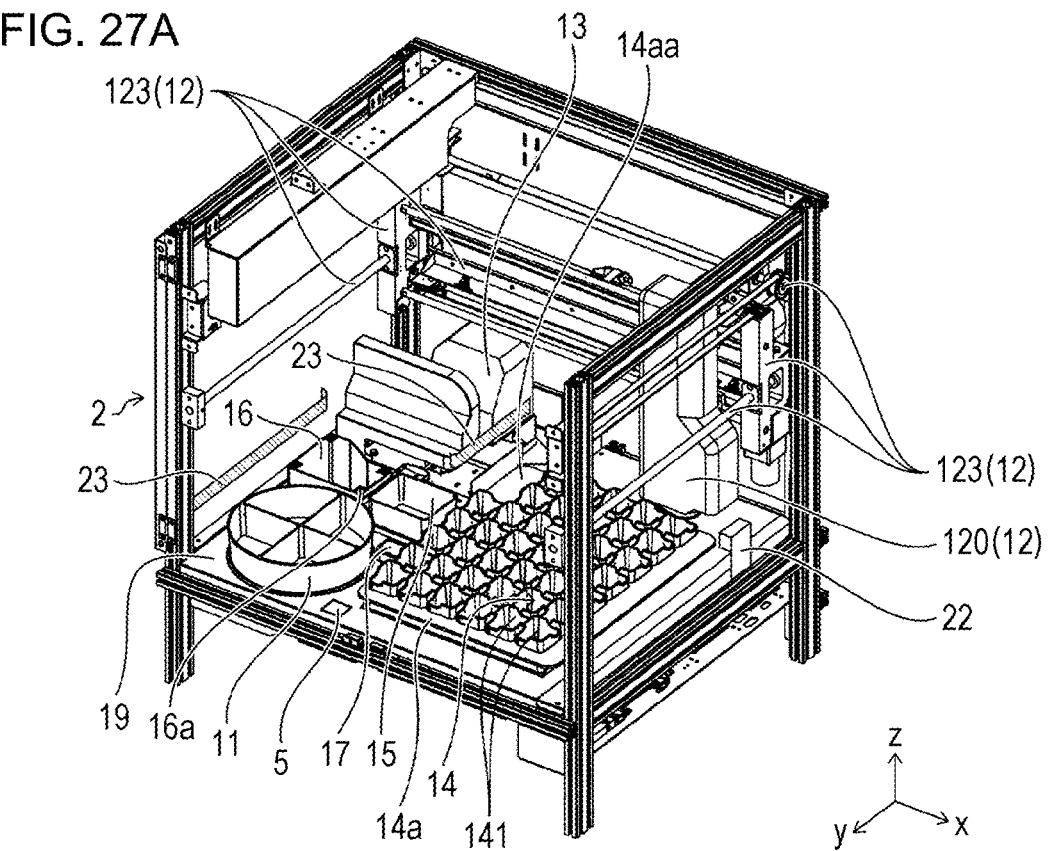
FIG. 27A is a perspective view for illustrating another example of the drug sorting device.
Figure 27B:
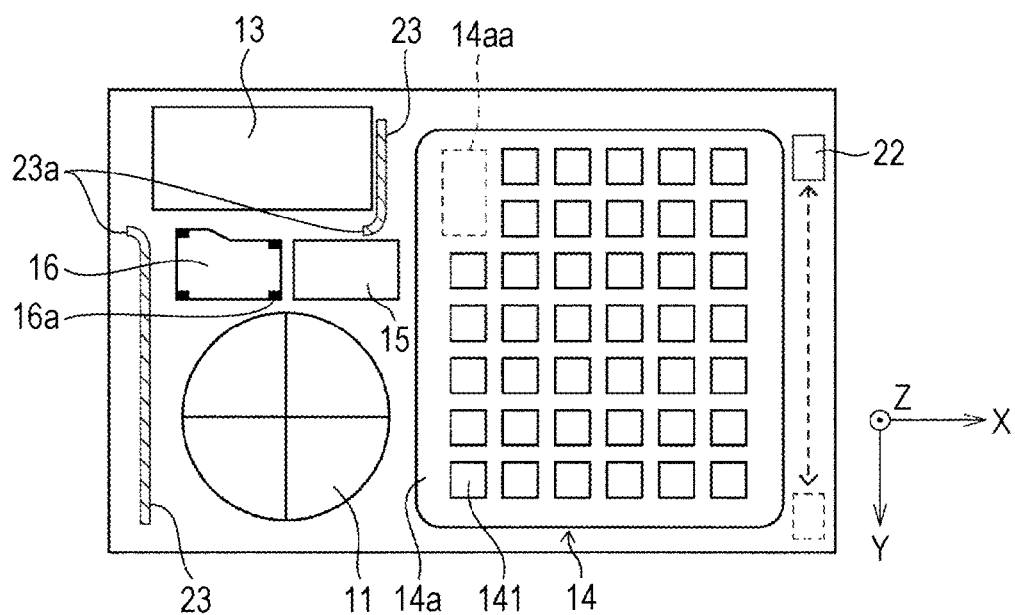
FIG. 27B is a schematic plan view for illustrating the another example.
Figure 28A:
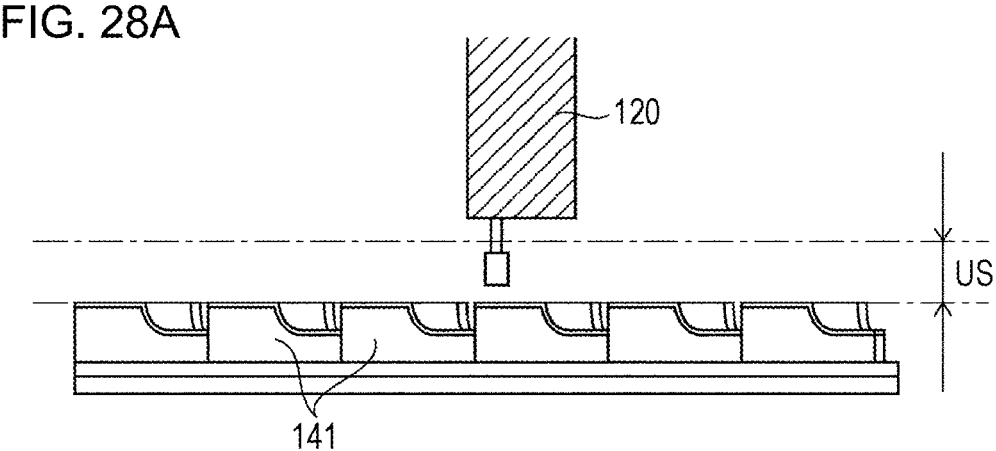
FIG. 28A and FIG. 28B are views for illustrating an upper space.
Figure 28B:
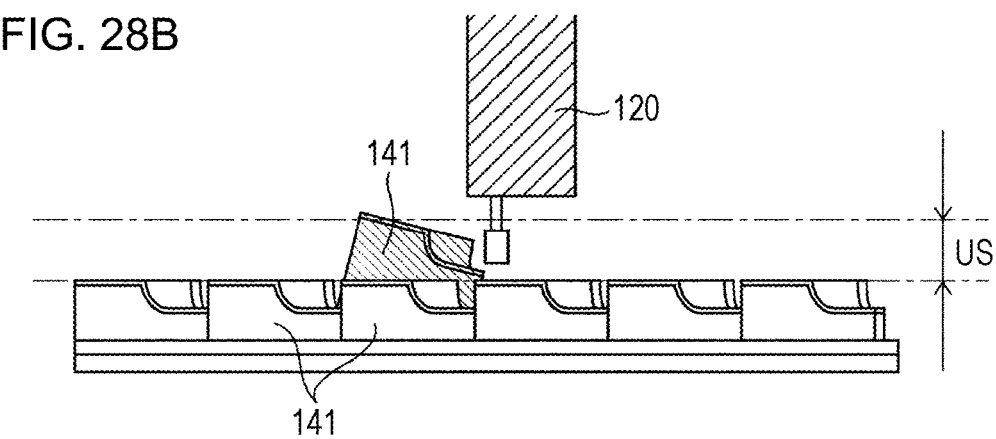

First, the obstacle detecting mechanism 22 is described with reference to FIG. 26 to FIGS. 28A and 28B. FIG. 27A is a perspective view for illustrating another example of the drug sorting device 1, and FIG. 27B is a schematic plan view for illustrating the another example. FIG. 28A and FIG. 28B are views for illustrating an upper space US.

As illustrated in FIG. 27A and FIG. 27B, the drug sorting device 1 according to this embodiment includes the obstacle detecting mechanism 22 and reflective mirrors 23.

The obstacle detecting mechanism 22 is configured to detect that some kind of obstacle is placed in the drug sorting area 2. Specifically, the obstacle detecting mechanism 22 functions as an object detection unit configured to detect an obstacle (object) that is present in the upper space US (see FIGS. 28A and 28B) above the sorting cups 141 placed (correctly placed) in the second accommodating portion 14 in a defined state. As illustrated in FIG. 27A, the obstacle detecting mechanism 22 is provided at one end of the drug sorting device 1 (pedestal 19).

The obstacle detecting mechanism 22 includes a light source (for example, a laser light source) configured to emit light through the upper space US and a sensor configured to receive the light emitted from the light source. When an obstacle is placed in the upper space US, the sensor cannot receive the light emitted by the light source, to thereby detect that an obstacle has been placed in this upper space US.

The reflective mirrors 23 are each provided at a position (other end) opposed to the obstacle detecting mechanism 22, and are configured to reflect the light emitted by the obstacle detecting mechanism 22 toward the obstacle detecting mechanism 22 side. When there is no obstacle in the upper space US, the sensor of the obstacle detecting mechanism 22 receives the light emitted from the light source of the obstacle detecting mechanism 22 and reflected by each reflective mirror 23. Meanwhile, when an obstacle is present in the upper space US, the sensor cannot receive the light emitted from the light source and reflected by each reflective mirror 23. At this time, the obstacle detecting mechanism 22 detects an obstacle present in the upper space US. That is, the target object presence/absence determination unit 72 determines that no obstacle is present in the upper space US when the obstacle detecting mechanism 22 receives the light, and that the obstacle is not present when the obstacle detecting mechanism 22 does not receive the light.

The obstacle detecting mechanism 22 moves in the horizontal direction under control of the drive control unit 71 (or the conveyance control unit 61, the sorting control unit 62, or the packaging control unit 74). As illustrated in FIG. 27B, in this embodiment, the obstacle detecting mechanism 22 moves in a y-axis direction (on a straight line connecting the drug take-out side and the rear side in the drug sorting device 1). Therefore, each reflective mirror 23 is provided so as to extend in the y-axis direction at the other end.

In this manner, the obstacle detecting mechanism 22 is made movable in a predetermined direction, to thereby be able to detect an obstacle present in the upper space US in the entire second accommodating portion 14 without providing a plurality of obstacle detecting mechanisms or providing one obstacle detecting mechanism extending in the predetermined direction. That is, a mechanism for detecting an obstacle can be provided at low cost.

The drug sorting device 1 includes the image pick-up unit 13. Therefore, the reflective mirrors 23 are provided on the inside of the casing (wall surface) of the drug sorting device 1 opposed to the obstacle detecting mechanism 22 and on the image pick-up unit 13 opposed to the obstacle detecting mechanism 22. As illustrated in FIG. 27B, an end portion 23*a* of each of the reflective mirrors 23 has a curved shape. When the end portion 23*a* is thus formed into a curved shape, it is possible to avoid misdetection of an obstacle that may occur when the end portion 23*a* has a non-curved shape.

As illustrated in FIG. 28A, the upper space US is, for example, a space between the bottom portion (lowermost plane opposed to the pedestal 19) of the drug conveying unit 120 and an uppermost plane of the sorting cup 141 exhibited when the sorting cup 141 is correctly placed on the pedestal 19.

The sorting cup 141 is attachably and detachably arranged in the second accommodating portion 14. Therefore, as illustrated in FIG. 28B, there is a case in which each sorting cup 141 may not be placed correctly and may be placed diagonally with respect to the pedestal 19. A state illustrated in FIG. 28A is a state in which all the sorting cups 141 are correctly placed. That is, a state in which each sorting cup 141 is placed so that its uppermost plane is substantially horizontal is the state in which the sorting cups 141 are correctly placed.

When a given sorting cup 141 is not correctly placed and is placed diagonally with respect to the pedestal 19, the obstacle detecting mechanism 22 detects, as an obstacle, a part of the given sorting cup 141 protruding from the uppermost plane (upper plane) of the sorting cup 141 exhibited when the sorting cup 141 is correctly placed on the pedestal 19. At this time, the obstacle detecting mechanism 22 is not receiving the emitted light, and hence the target object presence/absence determination unit 72 determines that an obstacle is present in the upper space DA. In this case, the display control unit 67 informs the user that this obstacle is to be removed (for example, the sorting cup 141 is to be correctly placed). Meanwhile, the drive control unit 71 (or the conveyance control unit 61, the sorting control unit 62, or the packaging control unit 74) stops the drug conveying unit 120 in a moving state.

In this manner, the obstacle detecting mechanism 22 and the target object presence/absence determination unit 72 can prevent the drug conveying unit 120 or the obstacle (for example, the sorting cup 141) from being damaged when a tip of the drug conveying unit 120 collides against the obstacle during its movement due to the presence of the obstacle in the upper space US.

In addition, for example, when drugs are piled up to adversely protrude from the uppermost plane of the standby tray 15 or the sorting cup 141, the obstacle detecting mechanism 22 detects, as obstacles, the drugs protruding from this uppermost plane. That is, the obstacle detecting mechanism 22 also functions as a mechanism for detecting drugs that protrude from the upper plane of the drugs accommodated in the standby tray 15 or the sorting cup 141. In this case, the display control unit 67 informs the user that the standby tray 15 or the sorting cup 141 is full of drugs. This can prevent drugs from adversely protruding out of the standby tray 15 or the sorting cup 141.

It is not required to provide the reflective mirrors 23. In this case, the obstacle detecting mechanism 22 detects an obstacle present in the upper space US when the obstacle detecting mechanism 22 receives the light emitted by the own mechanism (that is, when the obstacle detecting mechanism 22 receives light obtained by reflecting the emitted light by an obstacle). That is, the target object presence/absence determination unit 72 determines that an obstacle is present in the upper space US.

<Positioning Operation of Drug Conveying Unit>

Next, a positioning operation of the drug conveying unit 120 performed at the time of the activation of the drug sorting device 1 is described with reference to FIG. 26 and FIGS. 29A to 29D. FIG. 29A to FIG. 29D are views for illustrating the positioning operation of the drug conveying unit 120.

Figure 29A:
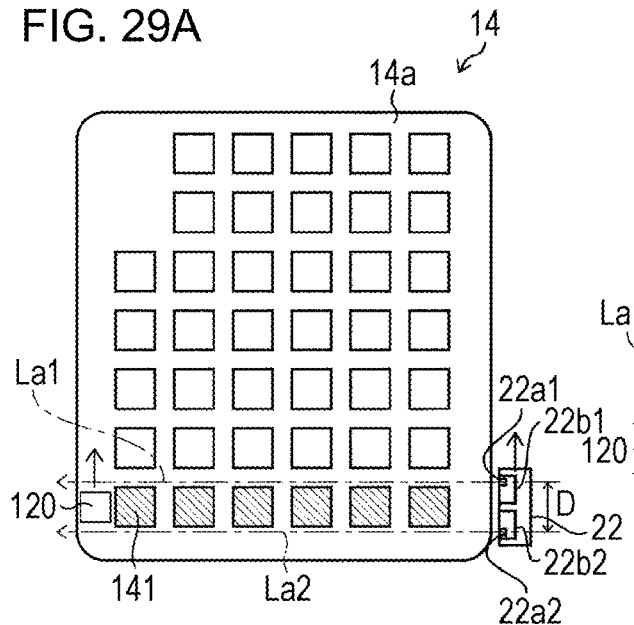
FIG. 29A, FIG. 29B, FIG. 29C, and FIG. 29D are views for illustrating a positioning operation of a drug conveying unit.

In this embodiment, the obstacle detecting mechanism 22 includes two obstacle detection units. One obstacle detection unit includes a light source 22a1 and a sensor 22b1, and the other obstacle detection unit includes a light source 22a2 and a sensor 22b2. As illustrated in FIG. 29A, the two obstacle detection units are arranged apart from each other by a distance (distance D1) larger than a width of the drug conveying unit 120 so as to prevent the drug conveying unit 120 from being irradiated with light La1 and light La2 emitted from the two obstacle detection units. In an actual case, the member present in the upper space US is the suction mechanism 122a. Therefore, it suffices that the above-mentioned distance D1 is at least a distance larger than a width of the suction mechanism 122a.

In addition, the drive control unit 71 moves the obstacle detecting mechanism 22 in conjunction with the movement of the drug conveying unit 120. In this embodiment, the obstacle detecting mechanism 22 is movable in the y-axis direction. Therefore, the obstacle detecting mechanism 22 moves in conjunction with the movement of the drug conveying unit 120 in the y-axis direction. Thus, it is possible to prevent the drug conveying unit 120 from being irradiated with the light La1 and the light La2 emitted from the obstacle detecting mechanism 22.

The drug sorting device 1 performs, at the time of its activation, a positioning operation of the drug conveying unit 120 with respect to the second accommodating portion 14 (specifically, sorting cup base 14a). Through this positioning operation, the control unit 60b (in particular, sorting control unit 62 and packaging control unit 74) can accurately identify the positions of the plurality of sorting cups 141 accommodated in the second accommodating portion 14.

In order to perform the positioning operation, it is required to move the drug conveying unit 120 in the extending directions (x-axis direction and y-axis direction) of sides that form an area in which the sorting cups 141 are placed. In this case, one end of the second accommodating portion 14 on the drug take-out side (for example, left end when viewed from the front side of the drug sorting device 1) is set as an initial position for starting the positioning operation.

In this embodiment, as illustrated in FIG. 29A, the drive control unit 71 first moves the drug conveying unit 120 to the initial position, and then starts the positioning operation. At this time, the drive control unit 71 turns on the obstacle detecting mechanism 22, to thereby emit the light La1 from the light source 22a1 and the light La2 from the light source 22a2. When there is no obstacle in the upper space US, the lights La1 and La2 are reflected by each reflective mirror 23 and received by the sensors of the obstacle detecting mechanism 22.

Next, as illustrated in FIG. 29A, the drive control unit 71 moves the drug conveying unit 120 and the obstacle detecting mechanism 22, for example, in the y-axis direction to an extent exceeding the distance D1. In this embodiment, this movement brings the drug conveying unit 120 to a position corresponding to a second row of sorting cups 141 in the y-axis direction. That is, the drug conveying unit 120 is located at a position that enables the movement over the sorting cups 141 in the second row along the x-axis direction. A moving distance in the y-axis direction is not limited thereto, and it suffices that the distance is long enough to enable the light La2 emitted from the light source 22a2 to detect the protrusion of each sorting cup 141 in a first row (long enough to enable the light La2 to pass over the sorting cups 141 in the first row). The sorting cups 141 in the first row refers to the sorting cups 141 shaded in FIGS. 29A to 29D.

In this case, it is conceivable that the drive control unit 71 moves the drug conveying unit 120 in the y-axis direction after moving the drug conveying unit 120 over the sorting cups 141 in the first row from the initial position. However, when the drug conveying unit 120 is located at the initial position, as illustrated in FIG. 29A, both the light La1 emitted from the light source 22a1 and the light La2 emitted from the light source 22a2 have not passed over the sorting cups 141 in the first row. For that reason, even when any one of the sorting cups 141 in the first row protrudes, the light La1 and the light La2 are not blocked by the protruding sorting cup 141, and hence the obstacle detecting mechanism 22 cannot detect this sorting cup 141. Therefore, when the drug conveying unit 120 is moved over the sorting cup 141 in the first row from the initial position, in a case where any one of the sorting cups 141 in the first row protrudes, the drug conveying unit 120 adversely collides with the protruding sorting cup 141.

As illustrated in FIG. 29A, the drug conveying unit 120 and the obstacle detecting mechanism 22 are moved in the y-axis direction by a predetermined distance from the initial position, to thereby enable the target object presence/absence determination unit 72 to examine whether or not each sorting cup 141 in the first row protrudes through use of the light La2 emitted from the light source 22a2 without moving the drug conveying unit 120 over the sorting cups 141 in the first row.

Figure 29B:
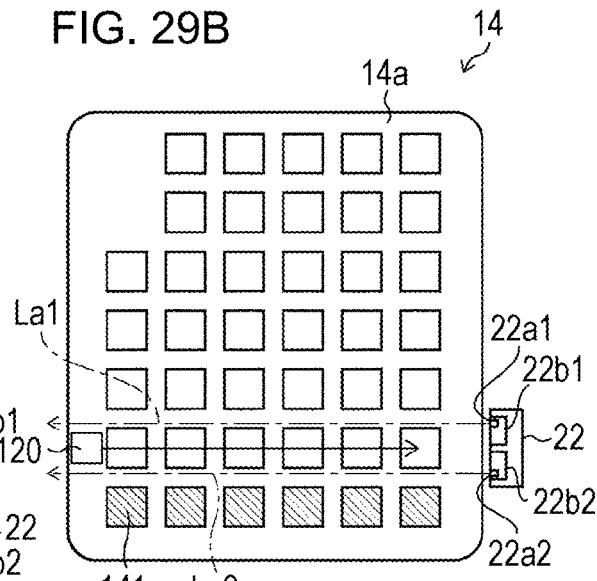

Subsequently, as illustrated in FIG. 29B, the drive control unit 71 moves the drug conveying unit 120 to the other end (for example, right end when viewed from the front side of the drug sorting device 1) of the second accommodating portion 14 along the x-axis direction over the sorting cups 141. In this embodiment, the drug conveying unit 120 is moved over sorting cups 141 in the second row along the x-axis direction to the sorting cup 141 arranged on the other end side. In regard to the sorting cups 141 in the second row, while the drug conveying unit 120 and the obstacle detecting mechanism 22 are being moved in the y-axis direction from the initial position, it is examined whether or not the protrusion has occurred through use of the light La1 emitted from the light source 22a1. Therefore, when it is detected that any one of the sorting cups 141 in the second row protrudes, the movement of the drug conveying unit 120 is stopped, and hence the drug conveying unit 120 can be prevented from colliding with the protruding sorting cup 141.

Figure 29C:
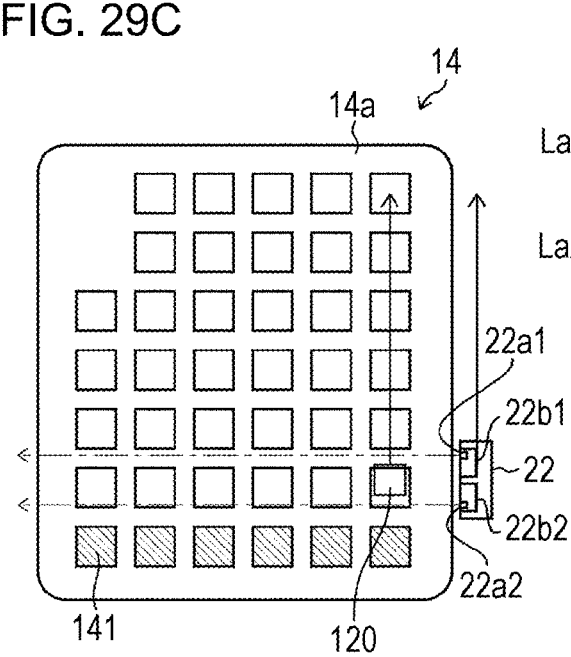
Figure 29D:
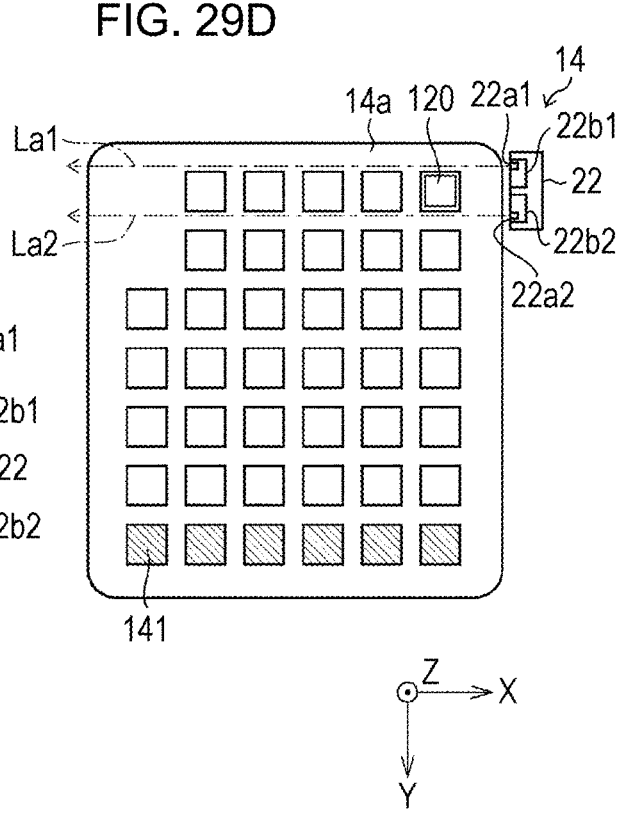

After that, as illustrated in FIG. 29C and FIG. 29D, the drive control unit 71 moves the drug conveying unit 120 and the obstacle detecting mechanism 22 over the sorting cups 141 arranged on the other end side along the y-axis direction, to thereby bring the positioning operation to an end.

As illustrated in FIG. 29A, the drive control unit 71 stops the drug conveying unit 120 and the obstacle detecting mechanism 22 even when the protrusion of any one of the sorting cups 141 in the first row is detected while the drug conveying unit 120 and the obstacle detecting mechanism 22 are being moved along the y-axis direction. In addition, as illustrated in FIG. 29C, the drive control unit 71 stops the drug conveying unit 120 and the obstacle detecting mechanism 22 even when the protrusion of any one of the sorting cups 141 in the third to seventh rows is detected while the drug conveying unit 120 and the obstacle detecting mechanism 22 are being moved along the y-axis direction.

In this manner, in the positioning operation, the drug conveying unit 120 is moved through an area subjected to the passage of the light La1 or the light La2 emitted from the light source 22a1 or the light source 22a2 of the obstacle detecting mechanism 22 being moved in conjunction with the drug conveying unit 120 over the second accommodating portion 14. Through this movement, the drug sorting device 1 can determine whether or not an obstacle is present in the area in which the drug conveying unit 120 is scheduled to be moved before the drug conveying unit 120 is moved. Therefore, it is possible to prevent the drug conveying unit 120 from colliding with the protruding sorting cup 141.

The movement example illustrated in FIGS. 29A to 29D is merely an example. For example, when the initial position is set so that the light La2 passes over the sorting cups 141 in the first row, the drug conveying unit 120 may be moved over the sorting cups 141 in the first row along the x-axis direction and then moved over the sorting cups 141 arranged on the other end side along the y-axis direction.

<Examination of Filter Clogging>

The drug sorting device 1 examines, at the time of its activation, clogging of a filter (not shown) provided to the suction mechanism 122a due to dust or other such foreign matter. This filter is used for collecting the dust or other such foreign matter sucked up from the suction pad 122c.

Figure 31:
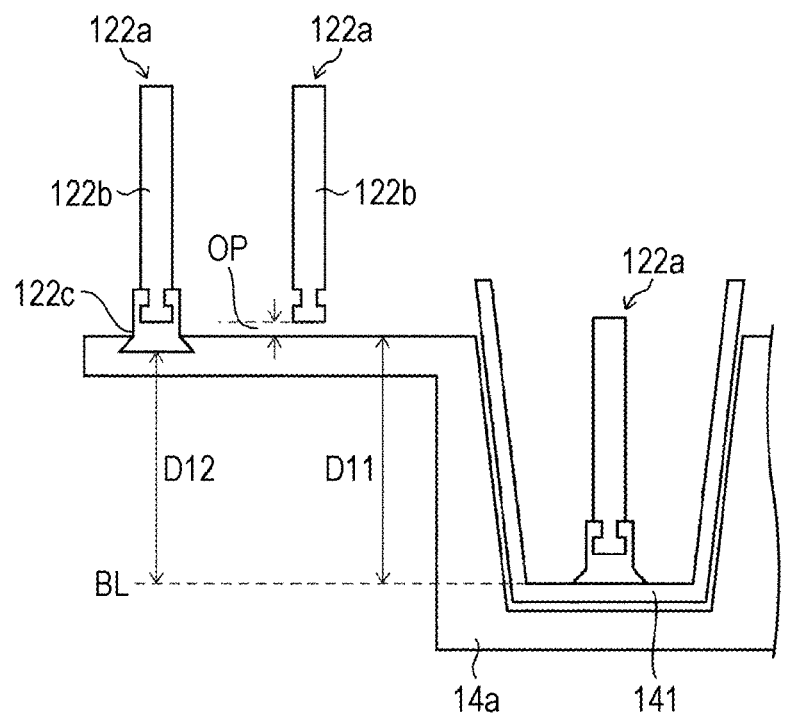
FIG. 31 is a view for illustrating determination of presence or absence of a suction pad.

The suction mechanism 122a includes a flow rate sensor (not shown) configured to detect the flow rate of air flowing through the air pipe 122b (see FIGS. 23A and 23B and FIG. 31). In this case, the conveyance control unit 61 (or sorting control unit 62 or packaging control unit 74) can determine that a drug has been sucked by the suction pad 122c based on a change in flow rate detected by the flow rate sensor.

The flow rate determination unit 73 determines whether or not the flow rate of air in the air pipe 122b exhibited when no drug is being sucked is equal to or lower than a first predetermined value (predetermined flow rate). When the flow rate determination unit 73 determines that the flow rate is equal to or lower than the first predetermined value, the flow rate determination unit 73 determines that the filter is clogged. In this case, the display control unit 67 informs the user that the filter is required to be cleaned or replaced due to the clogged filter. In addition, the control unit 60b stops the operation of the drug sorting device 1 at the time of the activation.

When it is determined that the flow rate is equal to or lower than the first predetermined value, the display control unit 67 may determine that there is an abnormality in the suction pad 122c and inform the user of the abnormality. In addition, this processing may be performed before the start of the drug sorting processing.

In addition, the predetermined value to be used for the determination by the flow rate determination unit 73 may be set in two steps of the first predetermined value and a second predetermined value. The first predetermined value is set as an index for determining that the filter is clogged to such an extent that cleaning is required. The second predetermined value is set as an index for determining that the filter is not clogged to such an extent that cleaning is required but the filter is clogged to such an extent that cleaning is to be required in the near future. Therefore, the second predetermined value is set higher than the first predetermined value.

In this case, the flow rate determination unit 73 determines whether or not the flow rate of air in the air pipe 122b exhibited when no drug is being sucked is equal to or lower than the second predetermined value. When the display control unit 67 determines that the flow rate is equal to or lower than the second predetermined value, the display control unit 67 informs the user that the cleaning of the filter is likely to be required in the near future. The control unit 60b temporarily stops the operation (or drug sorting processing) at the time of the activation in the drug sorting device 1, but restarts this operation when the operation input unit 66 receives the user input indicating the restart.

<Examination of Presence or Absence of Sorting Cup Base>

The drug sorting device 1 examines, at the time of its activation, whether or not the sorting cup base 14a is installed on the pedestal 19. This processing may be performed before the start of the drug sorting processing. As illustrated in FIG. 27A and FIG. 27B, the sorting cup base 14a is the accommodating portion configured to accommodate a plurality of sorting cups 141 in an aligned state.

Figure 30A:
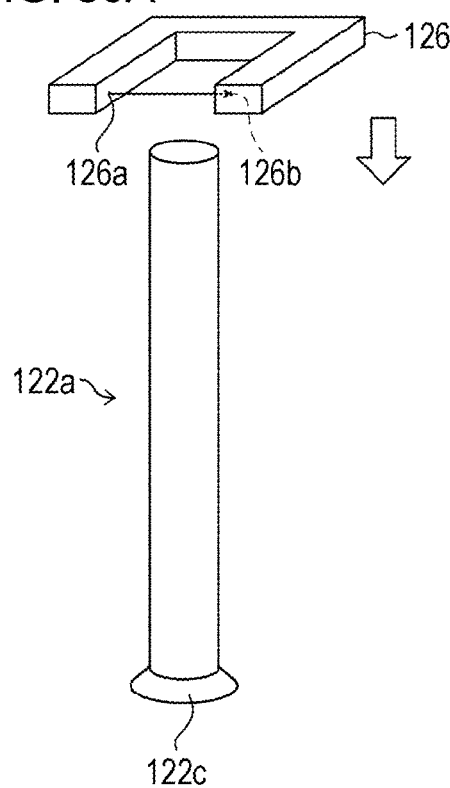
FIG. 30A and FIG. 30B are views for illustrating target object detection using a push-in detection unit.
Figure 30B:
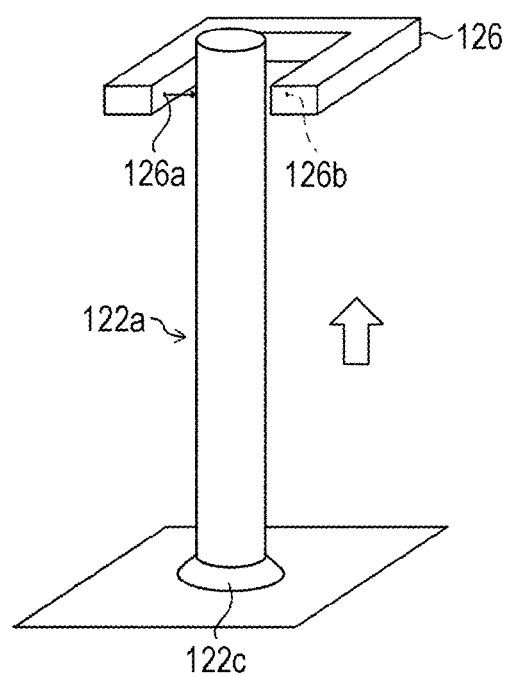

FIG. 30A and FIG. 30B are views for illustrating target object detection processing using a push-in detection unit 126. The drug conveying unit 120 includes the push-in detection unit 126 as illustrated in FIG. 30A and FIG. 30B. The push-in detection unit 126 is configured to detect that the suction mechanism 122a has been pushed in a direction reverse to an extending direction of the suction mechanism 122a from the drug conveying unit 120 toward the pedestal 19. In this embodiment, the push-in detection unit 126 has a substantially C shape, and a light source 126a and a sensor 126b are provided inside the push-in detection unit 126 so as to face each other. The push-in detection unit 126 is provided above the suction mechanism 122a so as to allow the suction mechanism 122a to pass through the inside of the push-in detection unit 126.

As illustrated in FIG. 30A, the push-in detection unit 126 is moved in conjunction with an extending action of the suction mechanism 122a. As illustrated in FIG. 30B, when the suction pad 122c is brought into contact with an object (for example, the sorting cup base 14a), the suction mechanism 122a is pushed up by a force of a spring (not shown) provided to the drug conveying unit 120. As a result, the sensor 126b becomes unable to receive the light emitted from the light source 126a. The target object presence/absence determination unit 72 determines that the tip end portion of the suction mechanism 122a has been brought into contact with the object when the sensor 126b has become unable to receive the light. That is, when the sensor 126b has become unable to receive the light, the target object presence/absence determination unit 72 determines that the tip end portion has been brought into contact with a target object supposed to be present, that is, that the target object is present.

As illustrated in FIG. 27A and FIG. 27B, the sorting cup base 14a has an area in which no sorting cup 141 is accommodated. This area is used to determine presence or absence of the sorting cup base 14a. This area is hereinafter referred to as "presence/absence determination area 14aa."

The drive control unit 71 lowers the suction mechanism 122a in the presence/absence determination area 14aa. It suffices that a lowering distance at this time is set to such an extent that the push-in detection unit 126 can detect contact with the presence/absence determination area 14aa when the sorting cup base 14a is installed and that the suction mechanism 122a is not brought into contact with the pedestal 19 when the sorting cup base 14a is not installed.

When the suction mechanism 122a is pushed up as a result of lowering the suction mechanism 122a and the sensor 126b has become unable to receive the light, the target object presence/absence determination unit 72 determines that the sorting cup base 14a is present. Meanwhile, when the suction mechanism 122a is not pushed up even by lowering the suction mechanism 122a by an amount corresponding to the above-mentioned lowering distance and the sensor 126b keeps receiving the light, the target object presence/absence determination unit 72 determines that no sorting cup base 14a is present. In this case, the display control unit 67 informs the user to install the sorting cup base 14a on the pedestal 19.

<Examination of Presence or Absence of Abnormal Suction>

The drug sorting device 1 examines, at the time of its activation, whether or not the suction can be normally detected when the suction mechanism 122a sucks a drug. This processing may be performed before the start of the drug sorting processing.

The flow rate determination unit 73 determines whether or not the flow rate of air in the air pipe 122b exhibited when no drug is being sucked is equal to or lower than a third predetermined value. It suffices that the third predetermined value is set to, for example, a flow rate exhibited when a drug is sucked, which is identified in advance through, for example, an experiment.

The drive control unit 71 lowers the suction mechanism 122a to bring the suction mechanism 122a into contact with the sorting cup base 14a in, for example, the presence/absence determination area 14aa. In this state, when the flow rate determination unit 73 determines that the flow rate is equal to or lower than the third predetermined value, the flow rate determination unit 73 determines that a drug can be sucked normally (that is, the control unit 60b can normally detect the suction of a drug). Meanwhile, when the flow rate determination unit 73 determines that the flow rate fails to become equal to or lower than the third predetermined value, the flow rate determination unit 73 determines that a drug cannot be normally sucked. In this case, the display control unit 67 informs the user that the suction mechanism 122a has become unable to normally suck a drug. When the flow rate fails to become equal to or lower than the third predetermined value, it is considered that there has occurred an abnormality, for example, damage to the air pipe 122b or the suction pad 122c. It is possible to inform the user to identify and repair a damaged spot.

<Examination of Presence or Absence of Standby Tray>

The drug sorting device 1 examines, at the time of its activation, whether or not the standby tray 15 is installed on the pedestal 19. This processing may be performed before the start of the drug sorting processing.

The image pick-up control unit 63 causes the second camera 121 provided to the drug conveying unit 120 to pick up an image of an area in which the standby tray 15 is installed, from above this area. The target object presence/absence determination unit 72 determines whether or not the standby tray 15 is included in this image by analyzing the image picked up by the image pick-up control unit 63. When this image includes the standby tray 15, the target object presence/absence determination unit 72 determines that the standby tray 15 is installed on the pedestal 19. Meanwhile, when this image does not include the standby tray 15, the target object presence/absence determination unit 72 determines that the standby tray 15 is not installed on the pedestal 19. In this case, the display control unit 67 informs the user to install the standby tray 15.

<Examination of Presence or Absence of Collection Tray>

The drug sorting device 1 examines, at the time of its activation, whether or not the collection tray 16 is installed on the pedestal 19. This processing may be performed before the start of the drug sorting processing.

As illustrated in FIG. 27A and FIG. 27B, protruding portions 16a each protruding inward are provided at four corners of the collection tray 16. The target object presence/absence determination unit 72 brings the suction mechanism 122a into contact with any one of the protruding portions 16a provided at the four corners, to thereby determine whether or not the collection tray 16 is installed.

This processing is performed by the same method as in the above-mentioned examination of the presence or absence of the sorting cup base 14a. Specifically, the drive control unit 71 lowers the suction mechanism 122a from above the area in which the collection tray 16 is installed. It suffices that a lowering distance at this time is set to such an extent that the push-in detection unit 126 can detect contact with the protruding portion 16a when the collection tray 16 is installed and that the suction mechanism 122a is not brought into contact with the pedestal 19 when the collection tray 16 is not installed.

When the suction mechanism 122a is pushed up as a result of lowering the suction mechanism 122a and the sensor 126b has become unable to receive the light, the target object presence/absence determination unit 72 determines that the collection tray 16 is present. Meanwhile, when the suction mechanism 122a is not pushed up even by lowering the suction mechanism 122a by an amount corresponding to the above-mentioned lowering distance and the sensor 126b keeps receiving the light, the target object presence/absence determination unit 72 determines that no collection tray 16 is present. In this case, the display control unit 67 informs the user to install the collection tray 16.

<Examination of Presence or Absence of Suction Pad>

The drug sorting device 1 examines, at the time of its activation, whether or not the suction pad 122c is attached to the suction mechanism 122a. This processing may be performed before the start of the drug sorting processing. FIG. 31 is a view for illustrating determination of presence or absence of the suction pad 122c.

The determination of the presence or absence of the suction pad 122c is performed based on whether or not the flow rate of air in the air pipe 122b exhibited when no drug is being sucked is, for example, equal to or lower than the third predetermined value. Specifically, for example, in the presence/absence determination area 14aa, the drive control unit 71 lowers the suction mechanism 122a to bring the suction mechanism 122a into contact with the sorting cup base 14a. In this state, when the flow rate determination unit 73 determines that the flow rate is equal to or lower than the third predetermined value, the flow rate determination unit 73 determines that the suction pad 122c is attached to the suction mechanism 122a. Meanwhile, when the flow rate determination unit 73 determines that the flow rate fails to become equal to or lower than the third predetermined value, the flow rate determination unit 73 determines that the suction pad 122c is not attached to the suction mechanism 122a. In this case, the display control unit 67 informs the user to attach the suction pad 122c to the suction mechanism 122a. Thus, it is possible to prevent the user from forgetting to attach the suction pad 122c.

In this case, a distance from the end portion (initial position of the suction mechanism 122a) of the drug conveying unit 120 on the side opposed to the pedestal 19 to the bottom portion of the sorting cup 141 correctly placed on the sorting cup base 14a is constant. Therefore, when this processing is performed in the presence/absence determination area 14aa, the lowering distance of the suction mechanism 122a (stop position of the suction mechanism 122a) is determined with a position of this bottom portion being set as a starting point, to thereby be able to determine this lowering distance with precision (for example, on the order of millimeter).

Specifically, as illustrated in FIG. 31, a distance D11 from a reference line BL that defines the above-mentioned position of the bottom portion to a surface of the sorting cup base 14a is constant. Therefore, a distance D12 obtained by subtracting a value obtained in consideration of the thickness of the suction pad 122c (for example, a value being half the thickness) from the distance D11 is also a constant value. In view of this, a position apart from the reference line BL by the distance D12 may be determined as the stop position of the suction mechanism 122a. That is, a distance from the initial position of the suction mechanism 122a to this stop position may be determined as the lowering distance.

Thus, the lowering distance (stop position) can be set to such an extent that the suction pad 122c is brought into contact with the surface of the sorting cup base 14a in a case where the suction pad 122c is attached and that the tip end portion of the suction mechanism 122a is not brought into contact with this surface in a case where the suction pad 122c is not attached.

That is, when the suction mechanism 122a is lowered by the lowering distance, as illustrated in FIG. 31, the flow rate becomes equal to or lower than the third predetermined value due to the contact of the suction pad 122c with the surface of the sorting cup base 14a in the case where the suction pad 122c is attached. Meanwhile, in the case where the suction pad 122c is not attached, there occurs a gap OP between the tip end portion of the suction mechanism 122a and the surface of the sorting cup base 14a, and hence the flow rate does not become equal to or lower than the third predetermined value. Therefore, the target object presence/absence determination unit 72 can accurately determine the presence or absence of the suction pad 122c.

<Examination of Stain on Drug Loading Stage and Remaining Drugs>

Figure 32:
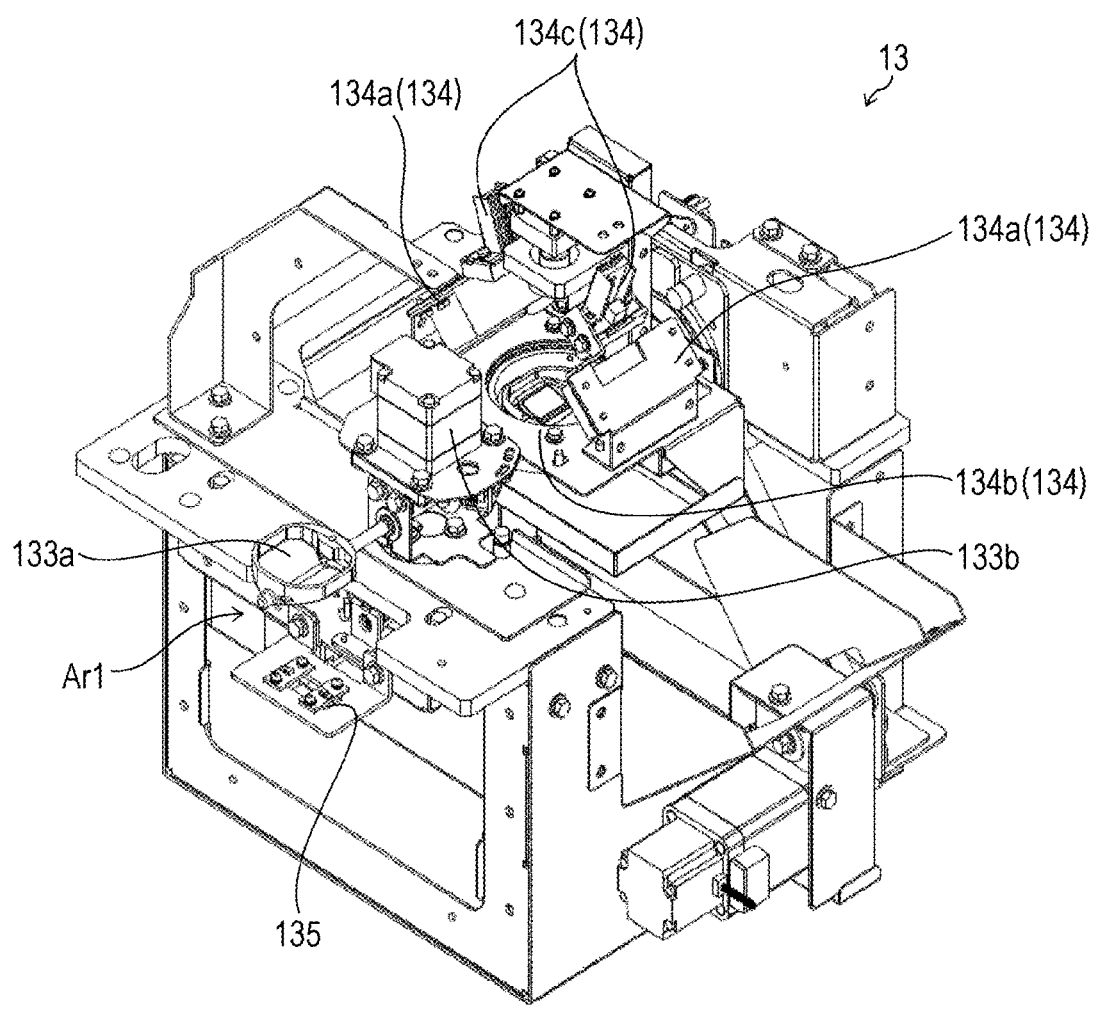
FIG. 32 is a perspective view for illustrating an example of arrangement positions of an illumination device and a backlight.

The drug sorting device 1 examines, at the time of its activation, presence or absence of the stain and the remaining drugs of the drug loading stage 133a. This processing may be performed before the start of the drug sorting processing. FIG. 32 is a perspective view for illustrating an example of arrangement positions of the illumination device 134 and a backlight 135.

In the image pick-up unit 13, the first irradiation unit 134a (visible light irradiation unit; bar illumination), the second irradiation unit 134b (visible light irradiation unit; ring illumination), and the ultraviolet light irradiation unit 134c are arranged as illustrated in FIG. 32. Meanwhile, as illustrated in FIG. 32, the receiving area Ar1 is provided with the backlight 135 configured to irradiate the drug loading stage 133a located in the receiving area Ar1 from below. When the suction mechanism 122a sucks a drug placed on the drug loading stage 133a located in the receiving area Ar1 (that is, when the suction position is determined above the drug loading stage 133a), the backlight 135 is caused to emit light. Thus, the suction position can be accurately determined.

The image pick-up control unit 63 picks up an image of the drug loading stage 133a located in the receiving area Ar1. When the image pick-up control unit 63 detects an area having a relatively low brightness as a result of analyzing the picked-up image, the image pick-up control unit 63 determines that the drug loading stage 133a has a stain. In this case, the display control unit 67 informs the user to clean the drug loading stage 133a due to a stain on the drug loading stage 133a. As a method for detecting this area having a relatively low brightness, for example, dynamic threshold processing or another such known method is used.

The image pick-up control unit 63 also analyzes the picked-up image to determine whether or not a drug is present on the drug loading stage 133a. The image pick-up control unit 63 determines that a drug is placed on the drug loading stage 133a when, for example, a matching degree with the estimated size and shape of a drug, which are identified in advance, is equal to or higher than the predetermined value. In this case, the drive control unit 71 controls the conveying/sorting unit 12 to convey the drug placed on the drug loading stage 133a to the first accommodating portion 11. Therefore, it is possible to prevent the drug sorting processing from being adversely started with the drug being placed on the drug loading stage 133a. In addition, the drug is accommodated into the first accommodating portion 11, to thereby be able to set this drug as an object to be sorted as well, and it is not required to inform that a drug is placed on the drug loading stage 133a.

After the presence or absence of a stain and remaining drugs on one drug loading stage 133a is examined, the presence or absence of a stain and remaining drugs on the other drug loading stage 133a is examined.

Operation Example

An operation example at the time of the activation in the drug sorting device 1 (or before the start of the drug sorting processing) is described. The drive control unit 71 moves the drug conveying unit 120 to the initial position at which the positioning operation is to be started, and then performs the positioning operation. When the positioning operation is completed, the drive control unit 71 moves the drug conveying unit 120 to the first accommodating portion 11.

The drive control unit 71 executes an air discharging processing by the suction mechanism 122*a* above the first accommodating portion 11. Thus, when a drug adheres to the suction pad 122*c*, it is possible to prevent the drug sorting processing from being adversely started with the drug adhering thereto. In addition, the drug adhering to the suction pad 122*c* is accommodated into the first accommodating portion 11, to thereby be able to set this drug as an object to be sorted as well, and it is not required to inform that a drug is adhering to the suction pad 122*c*.

Subsequently, the drive control unit 71 moves the drug conveying unit 120 to the presence/absence determination area 14*aa*. At this position, the processing steps of examining the presence or absence of the sorting cup base 14*a*, examining the presence or absence of the suction pad 122*c*, examining the presence or absence of the abnormal suction, and examining the filter clogging are performed.

Subsequently, the drive control unit 71 moves the drug conveying unit 120 to the standby tray 15. Thus, the processing step of examining the presence or absence of the standby tray 15 is performed. Subsequently, the drive control unit 71 moves the drug conveying unit 120 to the collection tray 16. Thus, the processing step of examining the presence or absence of the collection tray 16 is performed. Finally, the drive control unit 71 moves the drug conveying unit 120 to the receiving area Ar1. Thus, the processing step of examining the presence or absence of a stain and remaining drugs on the drug loading stage 133*a* is performed.

The drug sorting device 1 can perform the drug sorting processing safely and reliably by performing the above-mentioned processing at the time of its activation (or before the start of the drug sorting processing).

Seventeenth Embodiment

Figure 33A:
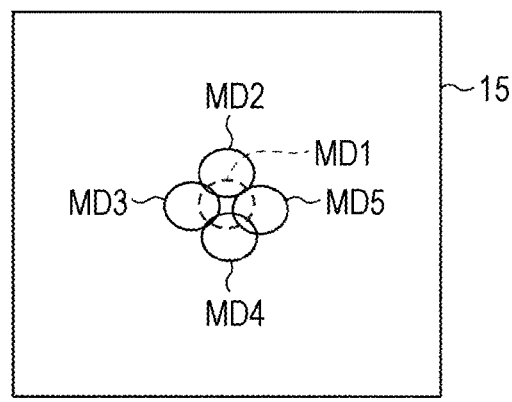
FIGS. 33A and 33B are diagrams for illustrating an example of arranging drugs onto a standby tray.
Figure 33B:
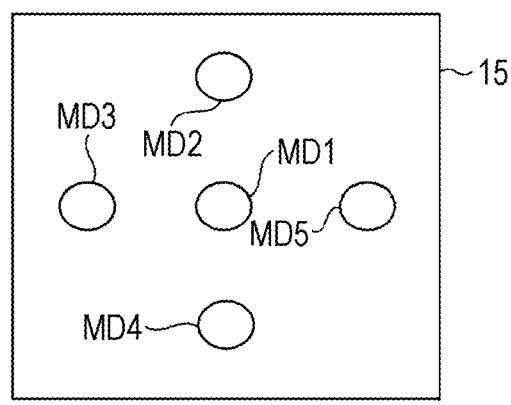

In this embodiment, a method of arranging drugs in the standby tray 15 is described with reference to FIGS. 33A and 33B. FIGS. 33A and 33B are diagrams for illustrating examples of arranging drugs into the standby tray 15. In FIGS. 33A and 33B, drugs MD1 to MD5 are assumed to be arranged in the standby tray 15 in the stated order.

It is also possible to examine an accommodation status of drugs in the standby tray 15 by picking up an image of the inside of the standby tray 15. However, in an actual case, it is difficult to grasp this accommodation status by analyzing the picked-up image. Therefore, as described above, the obstacle detecting mechanism 22 detects the presence of a drug that protrudes from the upper plane of the standby tray 15 (state of being full of drugs).

Meanwhile, it is also possible to make it difficult for a drug to protrude from the upper plane of the standby tray 15 depending on the method of arranging drugs in the standby tray 15. As illustrated in FIG. 33A, the drugs MD1 to MD5 are arranged at different positions, to thereby be able to make it difficult for drugs to be piled up in the standby tray 15. However, in this case as well, the drugs overlap each other. In view of this, as illustrated in FIG. 33B, the drugs MD1 to MD5 are arranged without an overlap between each of the drugs MD1 to MD5 and at least the previously arranged drug, and hence it is possible to make it more difficult for the drugs to be piled up in the standby tray 15. Specifically, at a position separated from a placed drug by a predetermined distance (for example, about 2 mm), the next drug is placed. The arrangement position in the standby tray 15 is determined by the control unit 60*b*.

Eighteenth Embodiment

In this embodiment, a method of switching a suction method depending on the shape of a drug and a sorting method are described. The shape or size of a drug may be a shape (for example, shape having a cross section being substantially circular, substantially elliptic, or substantially rectangular) or size of a general tablet or capsule, and there are also such shapes or sizes as follows, for example:

(1) a semi-tablet shape (shape having one arc and two corner parts), (2) a shape different from shapes of general tablets and capsules (for example, shape of a drug having a division line deeper than that of a general drug) (hereinafter referred to as "different shape"), and (3) a drug having a smaller size than sizes of general tablets and capsules (hereinafter referred to as "small drug"; the small drug is a drug equal to or smaller than a predetermined number in terms of pixels of its image, that is, such a drug that the number of pixels included in an area of the image of the drug in an image is equal to or smaller than a predetermined number of pixels).

When the drug is to be sucked, the control unit 60*b* performs an initial setting operation for lowering the suction mechanism 122*a* while performing suction. With such control, depending on the drug, the drug can be sucked before the suction mechanism 122*a* is brought into contact with the drug, and hence the drug sorting processing can be efficiently performed. However, when the suction mechanism 122*a* is lowered, while performing the suction, toward a drug having such a shape or size of any one of the above-mentioned items (1) to (3), the drug may be disturbed by a flow of air due to the suction before the drug has been sucked to the suction mechanism 122*a*, and hence the drug may fail to be sucked. In addition, the drug may be moved due to the above-mentioned flow of air, and the suction of the drug may fail at an appropriate position.

Therefore, when the sorting control unit 62 sorts the drugs having the above-mentioned shape or size, the initial setting operation is switched to a special setting operation of lowering the suction mechanism 122*a*, bringing the suction pad 122*c* into contact with the drug (pressing the suction pad 122*c* against the drug), and then starting the suction. The contact with the drug can be determined based on a change in flow rate.

In regard to a drug having a different shape, information indicating that the shape of this drug is a different shape is registered in the drug database in association with the drug data on this drug. When the discriminating unit 64 discriminates the type of the drug based on the image picked up by the first camera 131, the discriminating unit 64 refers to the drug database to determine whether or not this drug is designated as a drug having a different shape. When the drug is determined as a drug having a different shape, the sorting control unit 62 switches a suction operation from the initial setting operation to the special setting operation.

In addition, the discriminating unit 64 identifies the shape and the size of the drug placed in the arrangement area Ar2 based on the image picked up by the first camera 131. As a result, when the discriminating unit 64 determines that the drug is a drug having a semi-tablet shape or a small drug, the sorting control unit 62 switches the suction operation from the initial setting operation to the special setting operation. When the number of pixels included in the area of the image of the drug in the picked-up image is equal to or smaller than a predetermined number of pixels, it is determined that the drug is a small drug.

In this manner, in regard to a drug having such a special shape or size of any one of the above-mentioned items (1) to (3), the suction operation is switched to the special setting operation, to thereby be able to avoid such a situation that the drug cannot be sucked or the drug is adversely sucked at an improper position.

In addition, when the discriminating unit 64 determines that the drug is a drug having a semi-tablet shape, the sorting control unit 62 may sort drugs having a semi-tablet shape into the same sorting cup 141.

Nineteenth Embodiment

In this embodiment, processing performed when a plurality of drugs are placed on the drug loading stage 133*a* is described.

When the discriminating unit 64 is to discriminate the type of the drug, the discriminating unit 64 analyzes the image picked up by the first camera 131. When it is determined through this image analysis that a plurality of drugs are present on the drug loading stage 133*a*, processing for discriminating the type of the drug is interrupted, and the image pick-up control unit 63 moves the drug loading stage 133*a* from the arrangement area Ar2 to the receiving area Ar1. The conveyance control unit 61 moves the drug conveying unit 120 to a position above the receiving area Ar1, and then takes out one of the plurality of drugs mounted on the drug loading stage 133*a* based on the image picked up by the second camera 121, to thereby convey the one of the plurality of drugs to the first accommodating portion 11. The conveyance control unit 61 repeatedly perform this processing until all the plurality of drugs placed on the drug loading stage 133*a* have been conveyed to the first accommodating portion 11. Then, when the conveyance control unit 61 determines that no drug is present on the drug loading stage 133*a*, the conveyance control unit 61 again takes out one drug from the first accommodating portion 11, and places the one drug on the drug loading stage 133*a*. Thus, the processing for discriminating the type of the drug, which has been temporarily interrupted, is restarted.

In this manner, when a plurality of drugs are placed on the drug loading stage 133*a*, the drug sorting device 1 returns those drugs to the first accommodating portion 11, to thereby be able to reliably perform the processing for discriminating the types of the drugs one by one.

Twentieth Embodiment

Figure 34A:
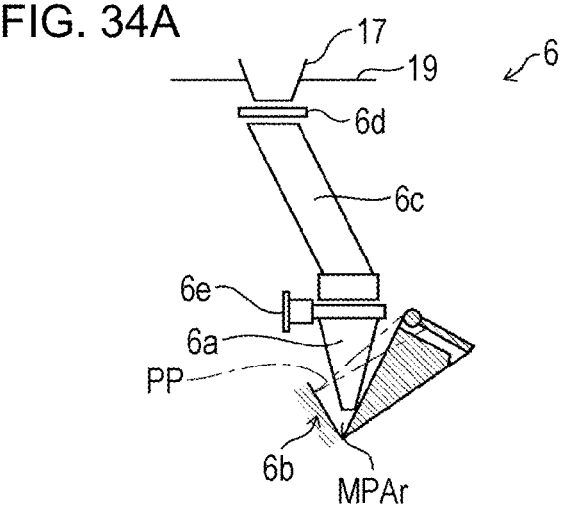
Figure 34B:
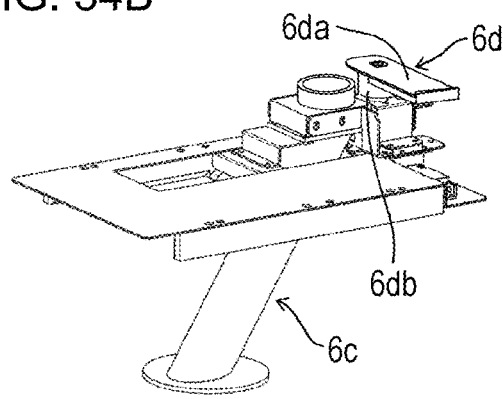
Figure 34C:
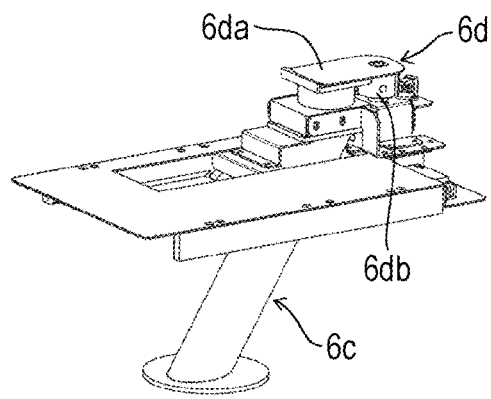
Figure 34D:
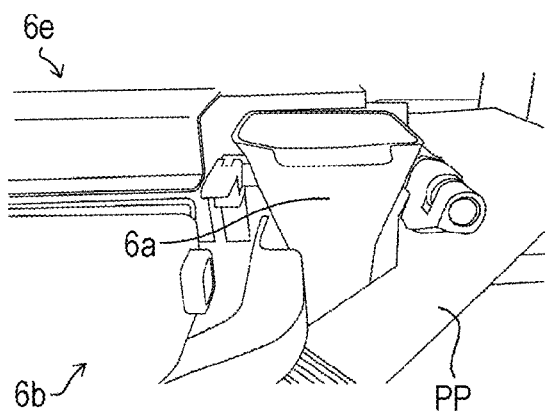
Figure 34E:
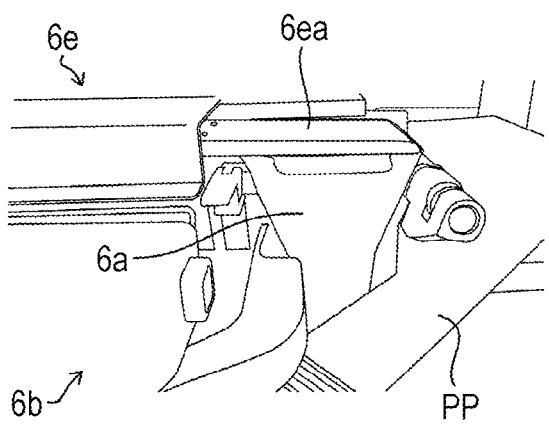

In this embodiment, a configuration of the packaging mechanism 6 (packaging unit) for packaging drugs stored in the second accommodating portion 14 is described with reference to FIGS. 34A to 34E. FIGS. 34A to 34E are views for illustrating a configuration example of the packaging mechanism 6. FIG. 34A is a view for schematically illustrating a partial configuration example of the packaging mechanism 6. FIG. 34B and FIG. 34C are views for illustrating an opening and closing operation in an upper shutter mechanism 6*d*, and FIG. 34D and FIG. 34E are views for illustrating an opening and closing operation in a lower shutter mechanism 6*e*.

As illustrated in FIG. 34A, the packaging mechanism 6 includes the package hopper 6*a*, the heater roller 6*b*, a movement passage 6*c*, the upper shutter mechanism 6*d*, and the lower shutter mechanism 6*e*. The heater roller 6*b*, the upper shutter mechanism 6*d*, and the lower shutter mechanism 6*e* are controlled by the packaging control unit 74.

The package hopper 6*a* is configured to receive drugs that have passed (dropped) through the movement passage 6*c* and guide the drugs to packaging paper sheets PP set in the heater roller 6*b*. Specifically, the package hopper 6*a* guides drugs that have passed through the movement passage 6*c* to a pre-packaging drug placement area MPAr in which the drugs are to be placed before the drugs are packaged by the heater roller 6*b*. In FIG. 34A, the packaging paper sheets PP are indicated by the one-dot chain lines. The package hopper 6*a* has a shape tapered toward the heater roller 6*b* side in order to place the drugs near the bottom portion of the heater roller 6*b* in the pre-packaging drug placement area MPAr.

The heater roller 6*b* is configured to package the drugs into the packaging paper sheets PP in units of packages. Specifically, the heater roller 6*b* thermally fuses the packaging paper sheets PP to package the drugs into the packaging paper sheets PP. The drugs corresponding to one package are placed in the packaging paper sheets PP in the pre-packaging drug placement area MPAr, to thereby be able to package drugs into the packaging paper sheets PP for every drugs corresponding to one package.

When the packaging mechanism 6 is to package drugs taken out from the sorting cup 141 subjected to the sorting by the same type, the packaging mechanism 6 may package all the drugs stored in one sorting cup 141 as one package. When the drugs stored in the sorting cup 141 have a large quantity, the drugs may be divided and packaged into a plurality of packages by a predetermined quantity. When the drugs are to be divided and packaged into a plurality of packages, their drug name may be printed on the packaging paper sheet PP by a printing mechanism (not shown) provided in the packaging mechanism 6. In this case, the packaging control unit 74 reads out the drug data from the RFID of the sorting cup 141, which is a source of taking out the drugs, to thereby print the drug name of those drugs on the packaging paper sheet PP into which those drugs are to be packaged. This allows the user to view which type of drugs are packaged in each package. In addition, when the drugs are to be divided and packaged into a plurality of packages, the packaging mechanism 6 may print, for example, "1/2" and "2/2" on the packages so that the user can examine a total number of packages of target drugs that have been packaged. The packaging mechanism 6 may also print, on the packaging paper sheet PP, a date or date/time at which the sorting processing is executed or information including a ward in which the sorting processing is executed.

The movement passage 6*c* is provided between the package hopper 6*a* and the drug feeding port 17 into which the drugs (drugs to be packaged) sorted by the conveying/sorting unit 12 is to be fed, and is configured to guide the drugs fed from the drug feeding port 17 to the package hopper 6*a*. In other words, the movement passage 6*c* connects the drug feeding port 17 and the pre-packaging drug placement area MPAr to each other, and is configured to guide the drugs fed into the drug feeding port 17 to the pre-packaging drug placement area MPAr.

The upper shutter mechanism 6*d* functions as a drug drop prevention unit, which is connected to the drug feeding port 17, and which is configured to prevent a drug that has been fed into the drug feeding port 17 but is not an object to be packaged from dropping into the packaging mechanism 6.

As illustrated in FIG. 34B, the upper shutter mechanism 6*d* includes an upper shutter 6*da* and an upper shutter drive unit 6*db*.

The upper shutter 6*da* is a shutter which is openable and closable, and which functions as a bottom portion of the drug feeding port 17. The upper shutter drive unit 6*db* controls an opening and closing operation of the upper shutter 6*da* by driving the upper shutter 6*da*. FIG. 34B is an illustration of a state in which the upper shutter 6*da* is open, and FIG. 34C is an illustration of a state in which the upper shutter 6*da* is closed.

The upper shutter 6*da* is normally in a closed state, and is opened when the drugs to be packaged are fed into the drug feeding port 17. Specifically, the packaging control unit 74 controls the conveying/sorting unit 12 to take out the drugs to be packaged from the corresponding sorting cup 141 and convey the drugs to the drug feeding port 17. The packaging control unit 74 opens the closed upper shutter 6*da* by controlling the upper shutter mechanism 6*d* after the drugs are fed into the drug feeding port 17. Thus, the drugs fed into the drug feeding port 17 are guided to the package hopper 6*a* through the movement passage 6*c*. The packaging control unit 74 closes the open upper shutter 6*da* after a predetermined time period (time period sufficient for the fed drugs to drop into the movement passage 6*c*) has elapsed.

In this manner, the upper shutter mechanism 6*d* is provided, to thereby be able to prevent a drug (drug that is not an object to be packaged) that has accidentally dropped into the drug feeding port 17 during the operation of the drug sorting device 1 from being adversely packaged by the packaging mechanism 6.

Meanwhile, under control of the packaging control unit 74, the second camera 121 (drug image pick-up unit) picks up an image of the drugs fed into the drug feeding port 17 before the upper shutter 6*da* is opened. The packaging control unit 74 stores the image picked up by the second camera 121 in the storage unit 80 as evidence of the packaging. This allows the user to view whether or not the drugs are correctly packaged through use of the image of the drugs picked up immediately before the drugs are packaged by the packaging mechanism 6.

The lower shutter mechanism 6*e* functions as a drug holding unit configured to temporarily hold the drugs fed from the drug feeding port 17 until all the drugs to be included in one package created by the packaging mechanism 6 have been fed from the drug feeding port 17. In other words, the lower shutter mechanism 6*e* prevents the drugs from being introduced into the pre-packaging drug placement area MPAr until all the drugs to be included in one package have been fed from the drug feeding port 17. Therefore, it suffices that the lower shutter mechanism 6*e* (specifically, lower shutter 6*ea* described later) is provided between the drug feeding port 17 and the pre-packaging drug placement area MPAr. In this embodiment, the lower shutter mechanism 6*e* is provided between the package hopper 6*a* and the movement passage 6*c*, but this disclosure is not limited thereto, and the lower shutter mechanism 6*e* may be provided, for example, inside the package hopper 6*a* or the movement passage 6*c*.

As illustrated in FIG. 34E, the lower shutter mechanism 6*e* also includes the lower shutter 6*ea* (shutter) which is openable and closable. In addition, the lower shutter mechanism 6*e* includes a lower shutter drive unit (not shown). The lower shutter drive unit controls an opening and closing operation of the lower shutter 6*ea* by driving the lower shutter 6*ea*. FIG. 34D is an illustration of a state in which the lower shutter 6*ea* is open, and FIG. 34E is an illustration of a state in which the lower shutter 6*ea* is closed.

The lower shutter 6*ea* is normally in a closed state, and is opened when the drugs corresponding to one package are held on the lower shutter 6*ea*. Specifically, the packaging control unit 74 opens the lower shutter 6*ea* after a predetermined time period has elapsed since the last drug among the plurality of drugs to be included in one package is fed into the drug feeding port 17 and the upper shutter 6*da* is opened. Thus, the drugs corresponding to one package are collectively guided to the package hopper 6*a* (that is, pre-packaging drug placement area MPAr). However, when the number of drugs to be included in one package is one, the last drug refers to this drug.

In this case, the storage unit 80 stores information indicating a maximum number of drugs that can be accommodated in one package for each type of drug (or, for example, size or shape of the drug). Specifically, for each type of drug, information indicating a maximum accommodation number of drugs that can be accommodated in one package having a standard bag length (for example, 80 mm) is stored. The packaging control unit 74 reads out the number of drugs stored in the sorting cup 141 from the RFID of this sorting cup 141, and compares this number with the maximum capacity, to thereby determine the bag length of one package and the quantity to be packaged in one package.

For example, when the packaging control unit 74 determines that the above-mentioned number is smaller than the maximum accommodation number, the packaging control unit 74 feeds all the drugs stored in the sorting cup 141 into the drug feeding port 17, and at the same time, shortens the bag length of one package for packaging the drugs stored in the sorting cup 141. For example, in a case of a drug having a maximum accommodation number of 8 tablets defined when the standard bag length is 80 mm, when the number of drugs to be packaged into one package is 7, the bag length is changed to 70 mm. The bag length may be changed stepwise, and in this case, can be changed among, for example, 70 mm, 76 mm, 80 mm (standard bag length), 90 mm, and 110 mm.

When the packaging control unit 74 determines that the above-mentioned number is the same as the maximum accommodation number, all the drugs stored in the sorting cup 141 are fed into the drug feeding port 17, and at the same time, maintains the standard bag length as the bag length of one package for packaging the drugs stored in the sorting cup 141.

When the packaging control unit 74 determines that the above-mentioned number of bags is larger than the maximum number of bags, the packaging control unit 74 sets the bag length of one package to a bag length (for example, 110 mm) longer than the standard bag length, and calculates the quantity of drugs that can be packaged in one package having this bag length based on the type of the drugs. Then, the calculated quantity of drugs may be fed from the sorting cup 141 into the drug feeding port 17. The same processing may be performed when the user desires to package as many drugs as possible into one package (when such a setting is enabled) according to the user's request.

In this manner, the packaging control unit 74 determines the quantity to be packaged in one package, and hence it is possible to identify which drug in one package is being fed into the drug feeding port 17 based on this quantity. The packaging control unit 74 may also identify which drug in one package is being fed into the drug feeding port 17 based on the prescription data.

The packaging control unit 74 also executes an operation of feeding the packaging paper sheets PP for one package at a timing when the drugs corresponding to one package have been placed in the pre-packaging drug placement area MPAr, and after this feeding operation is completed, the heater roller 6b thermally fuses those packaging paper sheets PP for one package. Thus, it is possible to package drugs into the packaging paper sheets PP for every drugs corresponding to one package.

It suffices that the above-mentioned predetermined time period is set to a time period sufficient for opening the upper shutter 6da and causing the drug to reach the lower shutter 6ea through the movement passage 6c. However, the packaging control unit 74 opens the lower shutter 6ea while the operation of feeding the packaging paper sheets PP is stopped.

In addition, the packaging control unit 74 closes the open lower shutter 6ea after a predetermined time period (time period sufficient for the drugs placed on the lower shutter 6ea to drop into the package hopper 6a) has elapsed.

In this manner, the lower shutter mechanism 6e is provided, to thereby be able to match a timing of placing the drugs corresponding to one package into the pre-packaging drug placement area MPAr and a timing of the operation of feeding the packaging paper sheets PP with each other. Therefore, the drug sorting device 1 can perform the packaging into the packaging paper sheets PP for every drugs corresponding to one package by the heater roller 6b.

In addition, the drugs are temporarily held by the lower shutter mechanism 6e, to thereby be able to drop the drugs corresponding to one package into the pre-packaging drug placement area MPAr at a time. Therefore, it is possible to avoid such a phenomenon that, while the drugs are dropped one by one, a drug is adversely caught between the packaging paper sheets PP that have not been thermally fused yet at a position before the pre-packaging drug placement area MPAr and fails to reach the pre-packaging drug placement area MPAr.

When the above-mentioned phenomenon occurs, the positions of the two packaging paper sheets PP that have not been thermally fused yet may be adversely misaligned. When the packaging paper sheets PP are thermally fused by the heater roller 6b under this state, the packaging becomes defective, and it is required to package the drugs again. The above-mentioned phenomenon can be avoided by providing the lower shutter mechanism 6e, and hence it is possible to prevent the packaging from becoming defective. Therefore, the drug sorting device 1 can efficiently package the drugs.

In other embodiments, the packaging mechanism 6 may have a configuration different from that described in this embodiment. As described above, for example, the package hopper 6a may be configured to temporarily hold the drugs fed from the drug feeding port 17. In addition, the movement passage 6c may be configured to move the drugs held by the package hopper 6a to the pre-packaging drug placement area MPAr.

Twenty-First Embodiment

In this embodiment, pre-processing for the packaging processing is described. It is also conceivable that a drug that is not an object to be packaged remains on the upper shutter 6da and the lower shutter 6ea illustrated in FIGS. 34A to 34E, for example, the drug used in the previous packaging processing remains as it is. In order to avoid packaging such a drug, the packaging control unit 74 opens the upper shutter 6da and the lower shutter 6ea at the start of the packaging processing. When a drug that is not an object to be packaged remains on the upper shutter 6da and the lower shutter 6ea, the drug can be dropped into the pre-packaging drug arrangement area MPAr through this operation. Then, the packaging control unit 74 packages the drug placed in the pre-packaging drug placement area MPAr through use of the packaging paper sheets PP, to thereby be able to dispense the packaged drug to the outside of the drug sorting device 1 before the drugs sorted into the second accommodating portion 14 are packaged.

In general, a packaging device is required to perform unloaded feeding on the packaging paper sheets PP corresponding to several packages without packaging drugs at the start of the packaging processing due to restrictions of the device. In the packaging mechanism 6, the drug left on the upper shutter 6da and the lower shutter 6ea can be packaged into those packaging paper sheets PP subjected to unloaded feeding (empty package). Therefore, in the packaging mechanism 6, a blank shot generated due to the restrictions of the device can be effectively used as a collected package for the above-mentioned drug.

The characters of "collected package" may also be printed on the packaging paper sheet PP by the printing mechanism so as to become distinguishable from other packages. In addition, the packaging mechanism 6 may be provided with an automatic line drawing device (not shown) using a pen, to thereby draw a colored line on the corresponding package as a marking that can be identified as a collected package.

Twenty-Second Embodiment

Figure 35:
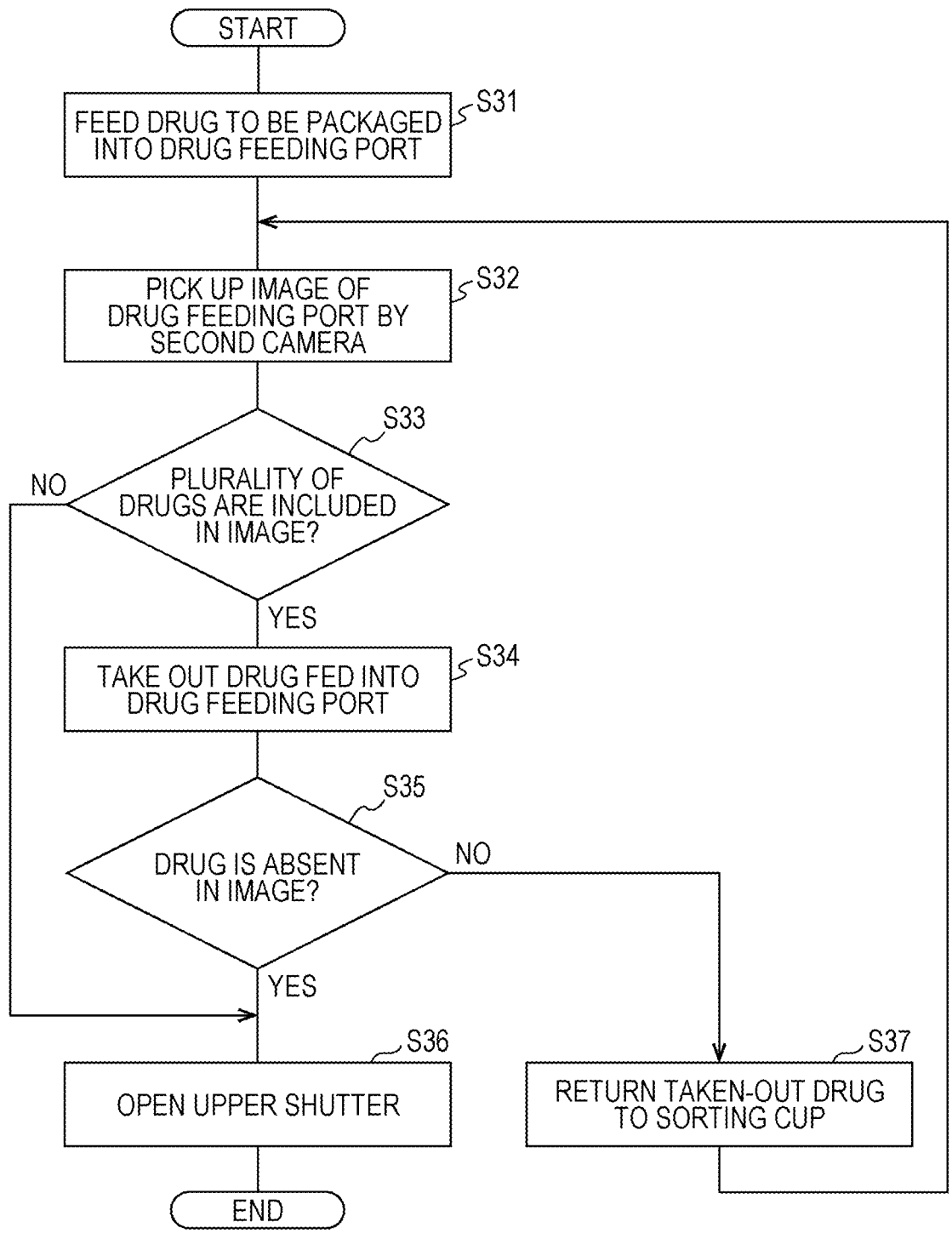
FIG. 35 is a flow chart for illustrating a processing example for dropping drugs one by one from a drug feeding port during the packaging processing.

In this embodiment, processing for dropping drugs one by one from the drug feeding port 17 at the time of the packaging processing is described with reference to FIG. 26 and FIG. 35. FIG. 35 is a flow chart for illustrating an example of this processing.

<Configuration of Drug Sorting Device>

As illustrated in FIG. 26, the packaging control unit 74 includes a number determination unit 741, a drug movement determination unit 742, and a to-be-packaged drug conveyance control unit 743.

The number determination unit 741 is configured to determine the number of drugs fed into the drug feeding port 17 based on the image of the inside of the drug feeding port 17 picked up by the second camera 121 (feeding image pick-up unit). Specifically, in a case where the number determination unit 741 has determined that the image picked up by the second camera 121 includes a plurality of drugs, the number determination unit 741 determines that the number of drugs fed into the drug feeding port 17 is one when no drug is included in an image picked up again by the second camera 121 under a state in which the drug fed into the drug feeding port 17 has been taken out.

The drug movement determination unit 742 is configured to determine to move the drug from the drug feeding port 17 to the packaging mechanism 6 when the number determination unit 741 determines that the number of drugs fed into the drug feeding port 17 is one. When the drug movement determination unit 742 determines this movement, the drug movement determination unit 742 drives the upper shutter drive unit 6db to open the upper shutter 6da. Thus, the drug can be moved to the packaging mechanism 6 only when the number of drugs fed into the drug feeding port 17 is one. That is, the drugs can be dropped one by one from the drug feeding port 17.

The to-be-packaged drug conveyance control unit 743 controls the conveying/sorting unit 12 to convey the drug stored in the second accommodating portion 14 to the drug feeding port 17. In the case where it is determined that the image picked up by the second camera 121 includes a plurality of drugs, when a drug is included in the image picked up again by the second camera 121 under the state in which the drug fed into the drug feeding port 17 has been taken out, the to-be-packaged drug conveyance control unit 743 returns the drugs fed into the drug feeding port 17 to the second accommodating portion 14.

In this case, the to-be-packaged drug conveyance control unit 743 returns one of the plurality of drugs fed into the drug feeding port 17 to the sorting cup 141 from which this drug has been taken out. Specifically, the to-be-packaged drug conveyance control unit 743 returns the drug, which has been taken out from the drug feeding port 17 in order to again pick up the image of the drug feeding port 17, to the sorting cup 141 from which this drug has been taken out. The to-be-packaged drug conveyance control unit 743 repeats a drug returning operation until the number of drugs fed into the drug feeding port 17 becomes one. Thus, even when a plurality of drugs are fed into the drug feeding port 17, the number of drugs present in the drug feeding port 17 can be set to one before the drug is dropped from the drug feeding port 17 to the packaging mechanism 6.

<Processing of Drug Sorting Device>

As illustrated in FIG. 35, the to-be-packaged drug conveyance control unit 743 feeds drugs to be packaged into the drug feeding port 17 (Step S31). The packaging control unit 74 controls the second camera 121 to pick up an image of the inside of the drug feeding port 17 after the drug has been fed (Step S32). The number determination unit 741 analyzes the image picked up by the second camera 121, to thereby determine whether or not a plurality of drugs are included in this image (Step S33).

When the number determination unit 741 determines that the above-mentioned image does not include a plurality of drugs (NO in Step S33), the drug movement determination unit 742 determines to move the drug from the drug feeding port 17 to the packaging mechanism 6. That is, in this case, the drug movement determination unit 742 controls the upper shutter mechanism 6d to open the upper shutter 6da (Step S36).

Meanwhile, when the number determination unit 741 determines that the above-mentioned image includes a plurality of drugs (YES in Step S33), the drug movement determination unit 742 keeps the upper shutter 6da closed. In this case, the packaging control unit 74 takes out the drug fed into the drug feeding port 17 (Step S34), and then controls the second camera 121 under this state to again pick up the image of the inside of the drug feeding port 17. Then, the number determination unit 741 analyzes the image picked up again by the second camera 121, to thereby determine whether or not this image includes a drug (Step S35).

When the number determination unit 741 determines that no drug is included in the above-mentioned image (YES in Step S35), the drug movement determination unit 742 determines to move the drug from the drug feeding port 17 to the packaging mechanism 6. That is, the drug movement determination unit 742 controls the upper shutter mechanism 6d to open the upper shutter 6da on the assumption that the number of drugs fed into the drug feeding port 17 is one (Step S36).

Meanwhile, when the number determination unit 741 determines that a drug is included in the above-mentioned image (NO in Step S35), the drug movement determination unit 742 keeps the upper shutter 6da closed on the assumption that there are a plurality of drugs fed into the drug feeding port 17. In this case, the to-be-packaged drug conveyance control unit 743 returns this drug taken out in Step S34 to the sorting cup 141 from which the drug was taken out (Step S37). After that, the procedure returns to the processing of Step S32.

In Step S34, the conveying/sorting unit 12 takes out one drug fed into the drug feeding port 17. Therefore, when there are a plurality of drugs fed into the drug feeding port 17, at least one drug remains in the drug feeding port 17 even after the drug is taken out in Step S34. Meanwhile, when the number of drugs fed into the drug feeding port 17 is one, no drug is present in the drug feeding port 17 after the drug is taken out in Step S34.

Even when it is determined in Step S33 that the image picked up includes a plurality of drugs, it may be determined in Step S35 that the image picked up (image obtained after one drug has been taken out) includes no drug. This is because, depending on the type (shape of, for example, the inscription) of the drug, it may adversely be determined that there are two drugs as a result of the image processing even when the result of the image pick-up indicates one drug. In this case, the number of drugs fed into the drug feeding port 17 is one, and hence the drug movement determination unit 742 opens the upper shutter 6da to guide this drug to the packaging mechanism 6.

Meanwhile, when the picked-up image (image obtained after one drug has been taken out) includes a drug in Step S35, it is certain that a plurality of drugs have been fed into the drug feeding port 17. Therefore, the taken-out drug is returned to the sorting cup 141, to thereby be able to reduce the drugs fed into the drug feeding port 17. Then, even when three or more drugs have been fed into the drug feeding port 17, while the number of drugs in the drug feeding port 17 is kept as one, the drug can be guided to the packaging mechanism 6 through the repetition of the above-mentioned processing.

In this manner, the drug sorting device 1 can prevent a plurality of drugs from being simultaneously dispensed from the drug feeding port 17 to the packaging mechanism 6. In addition, even when it is erroneously determined that there are two drugs in the image processing irrespective of the number of drugs fed into the drug feeding port 17 actually being one due to accuracy of image processing, it is possible to finally determine that there is one drug and dispense this one drug to the packaging mechanism 6. That is, in the case of the erroneous determination, the drug is not returned from the drug feeding port 17 to the sorting cup 141, or the user is not informed that a plurality of drugs are present in the drug feeding port 17.

Twenty-Third Embodiment

Figure 36:
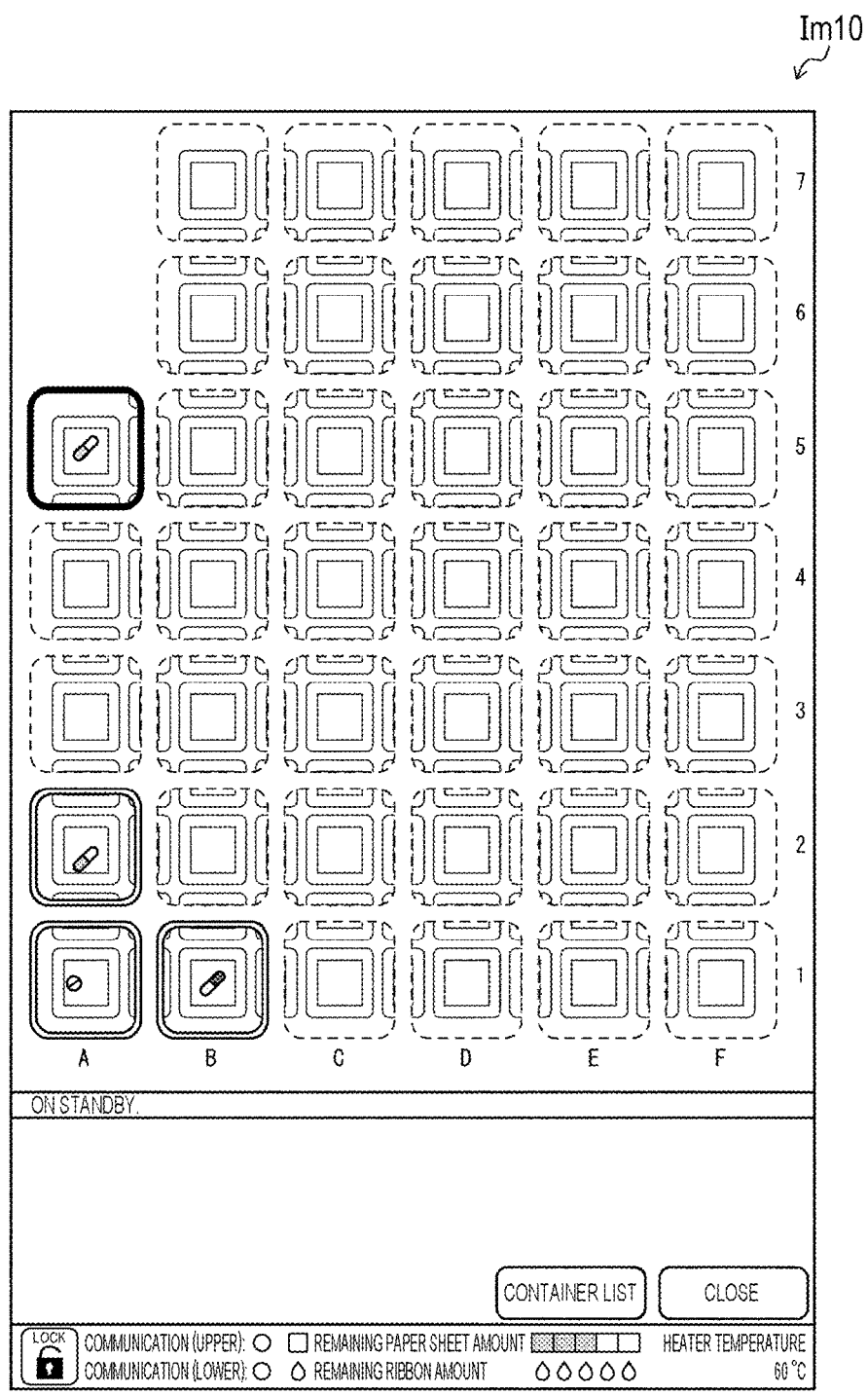
FIG. 36 is a diagram for illustrating an example of a remaining drug checking image.

In this embodiment, remaining drug checking processing for the sorting cup 141 is described with reference to FIG. 26 and FIG. 36. FIG. 36 is a diagram for illustrating an example of the remaining drug checking image Im10.

As illustrated in FIG. 26, the sorting control unit 62 includes a storage determination unit 621 and an information storage control unit 622.

The storage determination unit 621 is configured to determine whether or not a drug is stored in the sorting cup 141 based on the image of the inside of the sorting cup 141 picked up by the second camera 121 (container image pick-up unit). An image to be analyzed by the storage determination unit 621 is an image of the inside of an unused sorting cup 141 picked up by the second camera 121 before the conveying/sorting unit 12 sorts a drug. That is, when the unused sorting cup 141 is determined as the sorting position of the drug, the storage determination unit 621 determines whether or not a drug is stored in the sorting cup 141.

When the storage determination unit 621 determines that a drug is stored in the sorting cup 141, the information storage control unit 622 stores storage information indicating that a drug is stored in this sorting cup 141 in association with container identification information for identifying this sorting cup 141. Specifically, the information storage control unit 622 stores the storage information into the RFID tag provided on the sorting cup 141 determined to be storing a drug by the storage determination unit 621. Thus, the storage information and the container identification information are stored into the RFID tag in association with each other. However, the storage unit 80 may store the storage information and the container identification information in association with each other.

In this manner, when a drug is stored in the unused sorting cup 141, the drug sorting device 1 stores the storage information and the container identification information in association with each other, to thereby be able to identify that this sorting cup 141 is not in an unused state. Therefore, the drug sorting device 1 can avoid sorting the drug into the sorting cup 141. The drug sorting device 1 can also identify a position at which this sorting cup 141 is placed even when the position at which this sorting cup 141 is placed is changed in the second accommodating portion 14.

When the storage determination unit 621 determines that a drug is stored in the sorting cup 141, the sorting control unit 62 interrupts the drug sorting processing into this sorting cup 141. Then, the sorting control unit 62 conveys the drug being sucked by the conveying/sorting unit 12 to the first accommodating portion 11. In this case, the sorting control unit 62 may determine another unused sorting cup 141 as the sorting position to sort this drug into this sorting cup 141.

As illustrated in FIG. 26, the packaging control unit 74 also includes a storage determination unit 744 and an information storage control unit 745. The storage determination unit 744 and the information storage control unit 745 have the same functions as the storage determination unit 621 and the information storage control unit 622, respectively. However, an image to be analyzed by the storage determination unit 744 is the image of the inside of the sorting cup 141 picked up by the second camera 121 after the conveying/sorting unit 12 has dispensed all the drugs stored in the sorting cup 141 to the packaging mechanism 6.

In addition, the display control unit 67 displays the remaining drug checking image Im10 illustrated in FIG. 36. The remaining drug checking image Im10 is an image for displaying a storage status indicating whether or not the drugs sorted by the sorting control unit 62 are stored together with the sorting status of the drugs into the second accommodating portion 14.

As illustrated in FIG. 36, in this embodiment, in the remaining drug checking image Im10, the image of each sorting cup 141 is displayed, and at the same time, the above-mentioned storage status is displayed by displaying a border of the image of each sorting cup 141 in different colors. For example, the display control unit 67 (1) sets a blue border for the image of the unused sorting cup 141, and (2) sets a green border for the image of the sorting cup 141 in which the drug sorted by the sorting control 62 is stored. The display control unit 67 also (3) sets, when a drug is stored in the unused sorting cup 141, a red border for the image of this sorting cup 141 (that is, "a remaining drug is present" is indicated for this sorting cup 141). In FIG. 36, the border in the above-mentioned case (1) is indicated by the dotted line, the border in the above-mentioned case (2) is indicated by the double line, and the border in the above-mentioned case (3) is indicated by the thick line.

In the sorting cup 141 in which the drug sorted by the sorting control unit 62 is stored, the drug data on this drug is stored in the RFID tag. Therefore, the display control unit 67 can identify the sorting cup 141 having the drug data stored in the RFID tag as the sorting cup 141 in which the drug sorted by the sorting control unit 62 is stored.

Meanwhile, in the unused sorting cup 141 in which a drug is stored, the storage information is stored in the RFID tag. Therefore, the display control unit 67 can identify the sorting cup 141 having the storage information stored in the RFID tag as the unused sorting cup 141 in which a drug is stored.

The display control unit 67 can also identify the sorting cup 141 having no drug data and no storage information stored in the RFID tag as the unused sorting cup 141 in which no drug is stored (into which the drug can be sorted).

In this manner, when the storage determination unit 621 determines that a drug is stored in the unused sorting cup 141, the display control unit 67 (informing control unit) informs that the drug is stored therein. This allows the user to view the unused sorting cup 141 in which a drug is stored.

In regard to the unused sorting cup 141 in which a drug is stored, no drug is to be sorted (this unused sorting cup 141 is not to be determined as the sorting position of the drug) until the user performs a clearing operation. That is, the sorting control unit 62 recognizes this sorting cup 141 as a sorting target for the drug only after it is detected that the user has taken out this sorting cup 141 and the operation input unit 66 receives the user input indicating that the visual checking of the sorting cup 141 has been completed.

When the user input for examining remaining drugs is received, the control unit 60b causes the second camera 121 to pick up the image of the inside of each sorting cup 141. In this case, the control unit 60b may examine the remaining drugs in each sorting cup 141 based on whether or not a drug is included in the image of each sorting cup 141 and whether or not the drug data is stored in the RFID tag of each sorting cup 141.

In this case, for example, the display control unit 67 displays the border of the image in green when a drug is included in the image and the drug data is stored in the RFID tag. In the same manner, the display control unit 67 displays the border of the image in blue when no drug is included in the image and no drug data is stored in the RFID tag. The display control unit 67 also displays the border of the image in red when a drug is included in the image and no drug data is stored in the RFID tag.

In addition, the display control unit 67 displays, in a remaining drug checking image, the sorting status of the drugs into the second accommodating portion 14 together with the status of taking out drugs from each sorting cup 141 by the packaging control unit 74. For example, when a drug is stored in the sorting cup 141 after all the drugs have been taken out by the packaging control unit 74, the display control unit 67 sets the border of the image of the sorting cup 141 to have a color (for example, red) different from that of the other sorting cups 141. That is, the display control unit 67 displays the indication that "a remaining drug is present" for this sorting cup 141. The display control unit 67 can identify the sorting cup 141 having the storage information stored in the RFID tag as the sorting cup 141 indicating that "a remaining drug is present."

Twenty-Fourth Embodiment

In this embodiment, a function of assisting the user in cleaning the drug loading stage 133a is described.

When the user input for examining a state of the drug loading stage 133a is received, the drive control unit 71 moves the drug conveying unit 120 to a position above the receiving area Ar1. After that, the image pick-up control unit 63 causes the backlight 135 to emit light, and at the same time, picks up an image of one of the drug loading stages 133a by the second camera 121. When the image pick-up of one of the drug loading stages 133a is completed, the image pick-up control unit 63 moves the other drug loading stage 133a to this other receiving area Ar1, and then picks up an image of the drug loading stage 133a. The display control unit 67 displays the images of the two drug loading stages 133a. Thus, the user can examine the state (stain condition) of the drug loading stage 133a.

In the case of cleaning the drug loading stage 133a, the user selects the drug loading stage 133a to be cleaned from the two drug loading stages 133a. When the user input for selecting the drug loading stage 133a to be cleaned is received, the control unit 60b locates this drug loading stage 133a in the receiving area Ar1. After that, the control unit 60b releases a lock of an opening/closing shutter. This allows the user to easily take out and clean the drug loading stage 133a selected as a cleaning target.

It is also possible for the user to manually swivel the drug loading stages 133a in order to move the drug loading stage 133a to be cleaned to the receiving area Ar1. However, in this case, there is a possibility that the drug loading stage 133a may be damaged depending on a position for grasping the drug loading stage 133a or a tilt of the drug loading stage 133a during the swivel. As described above, it is possible to prevent the drug loading stage 133a from being damaged by automatically moving the drug loading stage 133a to be cleaned to the receiving area Ar1 (by performing the movement under control of the control unit 60b).

Twenty-Fifth Embodiment

In this embodiment, processing for similar drugs is described with reference to FIG. 26 and FIGS. 37A and 37B. FIG. 37A is a diagram for illustrating an example of a similar drug display image Im11, and FIG. 37B is a diagram for illustrating an example of a similar drug selection image Im12.

The discriminating unit 64 discriminates the type of the drug based on the image picked up by the first camera 131. At this time, when the discriminating unit 64 determines that the drug included in the image is similar to the image of the drug registered in the drug database, the discriminating unit 64 identifies the drug being the discrimination target and the drug registered in the drug database as similar drugs. The similarity is determined based on whether or not the feature of the drug extracted from the image for determining the type of the drug is similar to the feature of the drug registered in the drug database. A determination criterion for the similarity may be set in advance through, for example, an experiment.

When the discriminating unit 64 is to discriminate the type of the drug, the discriminating unit 64 compares the feature of the drug extracted from the image with the features of all the drugs registered in the drug database (including features of the drugs registered in a similar drug list described later). As a result, when the discriminating unit 64 discriminates that the drug is a drug (estimated drug) that is not registered in the drug database, the discriminating unit 64 determines whether or not a drug having a feature similar to the feature of the estimated drug is present among the drugs registered in the drug database.

When the discriminating unit 64 determines that drugs having similar features are present, the discriminating unit 64 identifies, as similar drugs, the feature of the estimated drug being the discrimination target for the type and the drug having a similar feature, which is registered in the drug database. Then, the discriminating unit 64 registers the drug data on the estimated drug in the drug database, and registers pieces of drug data on the two drugs identified as the similar drugs in the similar drug list in association with each other as the similar drugs. The similar drug list is a list indicating which drugs are similar to each other among the drugs registered in the drug database.

When the operation input unit 66 receives the user input indicating that a piece of drug data on any one of the drugs identified as the similar drugs is to be adopted as drug data for the similar drugs, the discriminating unit 64 identifies the adopted (designated) piece of drug data as the drug data for the similar drugs. In this case, when the discriminating unit 64 is to discriminate the type of the drug, in regard to the similar drugs, only the designated piece of drug data is subjected to the comparison with the drug data on the drug being the discrimination target for the type. In other words, when the drug data for the similar drugs is not designated, all the pieces of drug data on the drugs identified as the similar drugs are subjected to the comparison with the drug data on the drug being the discrimination target for the type.

When the operation input unit 66 receives the user input indicating that a piece of drug data on any one of the drugs identified as the similar drugs is to be deleted, the discriminating unit 64 deletes this piece of drug data from the drug database. As a result, a drug for which no similar drug is no longer present in the drug database is excluded from the similar drug list.

In addition, the sorting control unit 62 stores the drugs registered in the similar drug list into the same sorting cup 141. In the image for displaying the sorting status of the drug into the second accommodating portion 14, the display control unit 67 displays, for the sorting cup 141 in which similar drugs are stored, information indicating that the similar drugs are stored therein. For example, the display control unit 67 displays "similar drugs" for this sorting cup 141 in this image. However, when one piece of drug data is designated as the drug data for the similar drugs, the display control unit 67 displays the drug name indicated by the designated piece of drug data instead of displaying the "similar drugs."

As described above, the estimated drug similar to the drug registered in the drug database is stored in the same sorting cup 141 as that of the registered drug, to thereby allow the user to visually inspect the estimated drug together with the registered drug.

There is also a case in which even drugs having the same type may be determined to have different features due to, for example, a change in distributor (or manufacturer) or a date of sale (new or old). For example, when there is a change in distributor, the YJ code becomes different even when the inscribed information acquired from the image is the same. Therefore, when the YJ code after the change in distributor is not registered in the drug database for such a drug, there is a possibility of failing to be stored into the same sorting cup 141 as that of the drug having the YJ code before the change in distributor. The estimated drug similar to the drug registered in the drug database is stored into the same sorting cup 141 as that of the registered drug, to thereby be able to avoid storing the drugs having substantially the same type into different sorting cups 141. It is also possible to sort such drugs more safely by prompting the user to perform the visual inspection.

Specific Example

For example, it is assumed that pieces of drug data on three types of drugs having inscriptions (features) of "10," "8," and "XYZ" are registered in the drug database stored in the storage unit 80. It is also assumed that the drug data on the drug being the discrimination target for the type has the inscription (feature) of "B" or "13." It is also assumed that the discriminating unit 64 determines whether or not the inscriptions are similar to each other as a result of analyzing the images, and that the inscriptions of "8" and "B" or the inscriptions "B" and "13" are similar to each other. The drugs having the inscriptions of "10," "8," "XYZ," "B," and "13" are referred to as a "10" drug, an "8" drug, an "XYZ" drug, a "B" drug, and a "13" drug, respectively.

When the discriminating unit 64 is to discriminate the type of the "B" drug, the discriminating unit 64 compares the inscription of "B" with each of the inscriptions of "10," "8," and "XYZ" of the drugs registered in the drug database, and as a result, determines that the inscription of "B" is similar to the inscription of "8." The discriminating unit 64 registers the drug data on the "B" drug in the drug database, and simultaneously registers the "8" drug and the "B" drug in the similar drug list.

Meanwhile, the sorting control unit 62 stores the "8" drug and the "B" drug into the same sorting cup 141. The display control unit 67 displays the "similar drugs" for this sorting cup 141 in the image for displaying the sorting status.

After that, when the discriminating unit 64 is to discriminate the type of the "13" drug, the discriminating unit 64 compares the inscription of "13" with each of the inscriptions of "10," "8," "XYZ," and "B" of the drugs registered in the drug database, and as a result, determines that the inscription of "13" is similar to the inscription of "B." The discriminating unit 64 registers the drug data on the "13" drug in the drug database, and simultaneously registers the "B" drug and the "13" drug in the similar drug list.

In this case, two combinations of (1) the "8" drug and the "B" drug and (2) the "B" drug and the "13" drug are registered in the similar drug list, and the "B" drug is common in those combinations (1) and (2). Therefore, the sorting control unit 62 stores the "8" drug, the "B" drug, and the "13" drug into the same sorting cup 141. When the drug data on the "B" drug has been deleted from the drug database, it is not determined that the "8" drug and the "13" drug are similar to each other, and hence the above-mentioned combinations (1) and (2) are both removed from the similar drug list.

Display Example

Next, the similar drug display image Im11 and the similar drug selection image Im12 are described with reference to FIGS. 37A and 37B.

The similar drug display image Im11 is an image for displaying data relating to the drugs registered in the similar drug list. In the example of FIG. 37A, a YJ code, a drug name, and an image picked up by the first camera 131 are displayed in the similar drug display image Im11 for every drugs registered as similar drugs.

The similar drug selection image Im12 is an image for selecting which one of pieces of drug data on the similar drugs registered in the similar drug list is to be adopted as the drug data for the similar drugs. In the example of FIG. 37B, in the similar drug selection image Im12, the images, drug names, and pieces of inscribed information of drugs forming the similar drugs selected in the similar drug display image Im11 are displayed together with adopt buttons Bo11 and Bo12 and a cancel button Bo2.

The adopt buttons Bo11 and Bo12 are operation buttons displayed for every drug forming the similar drug and used for determining the drug data on the drug to be adopted as the drug data for the similar drugs. For example, when the user touches the adopt button Bo11 indicated as "Adopt similar drug 1," the drug data on the "similar drug 1" is adopted as the drug data for the similar drugs. The release button Bo2 is used for canceling the above-mentioned adoption.

Twenty-Sixth Embodiment

In this embodiment, processing for approving registration in the drug database is described. Drug data is registered in the drug database after being subjected to the visual inspection by the user and approval by the user. Specifically, the drug sorting device 1 prompts the user to perform the visual inspection when the drug data temporarily registered in the drug database is to be used for the first time. After the visual inspection of the temporarily registered drug data, the user performs the user input indicating that it is to be approved to fully register the above-mentioned drug data in the drug database. When the drug sorting device 1 receives this user input, the drug sorting device 1 fully register the above-mentioned drug data in the drug database.

Drug data may be registered in the drug database by a third party (for example, distributor or manufacturer of the drug sorting device 1) other than the user authorized to perform the visual inspection. Therefore, the safety of the drug sorting device 1 can be improved by registering (fully registering) the drug data in the drug database after the approval of the user.

For example, the third party asks a delivery destination of the drug sorting device 1 (for example, hospital) about the types of drugs being used at the delivery destination to create the drug database, but drugs for which the third party has no information cannot be registered in the drug database. Therefore, the third party asks the delivery destination to provide data and images relating to those unregistered drugs, and also registers the unregistered drugs in the drug database. Even in such a case, the unregistered drug data is fully registered in the drug database after the registration is approved by the user at the time of use for the first time.

Twenty-Seventh Embodiment

Figure 38B:
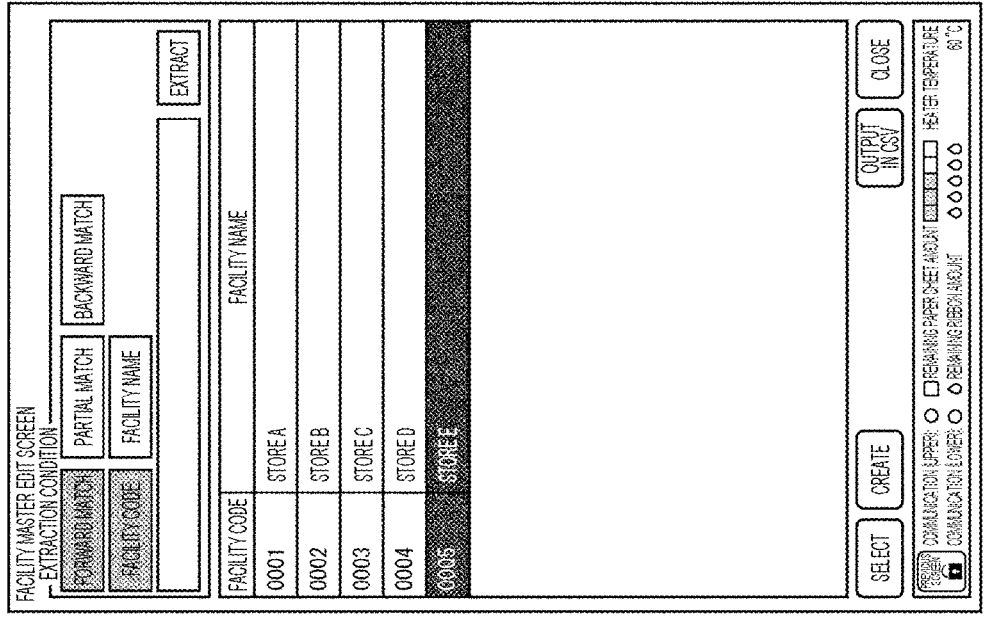
FIG. 38B is a diagram for illustrating an example of a return source registration image.
Figure 38A:
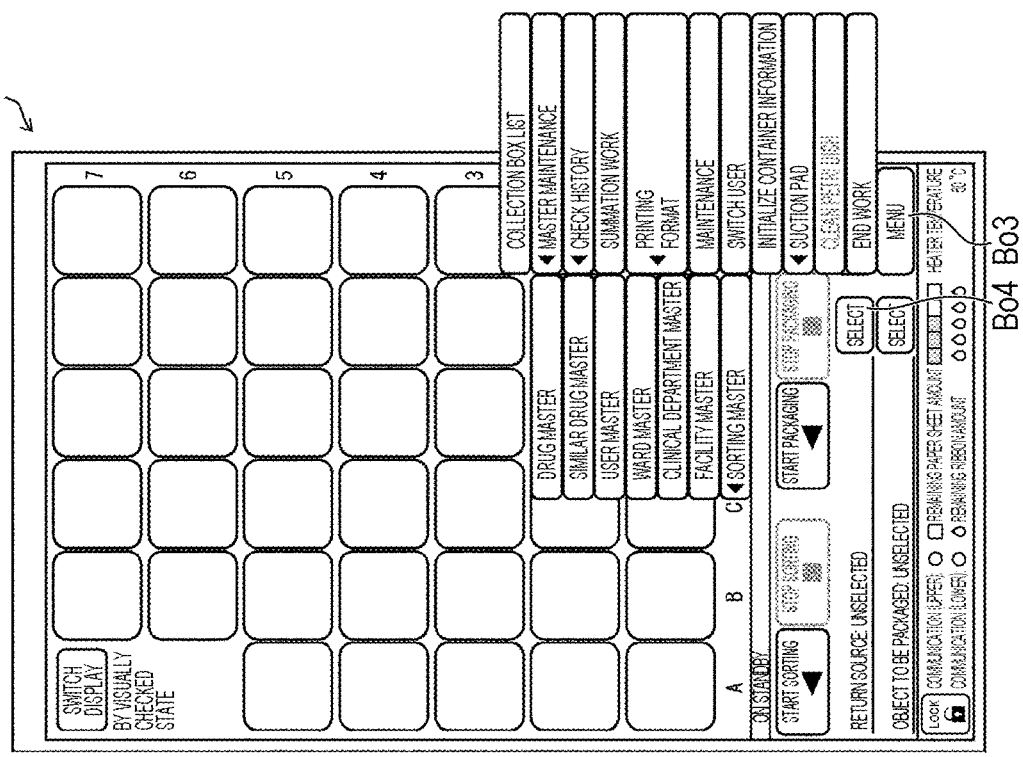
FIG. 38A is a diagram for illustrating an example of a sorting image displayed before a return source is selected.
Figure 39B:
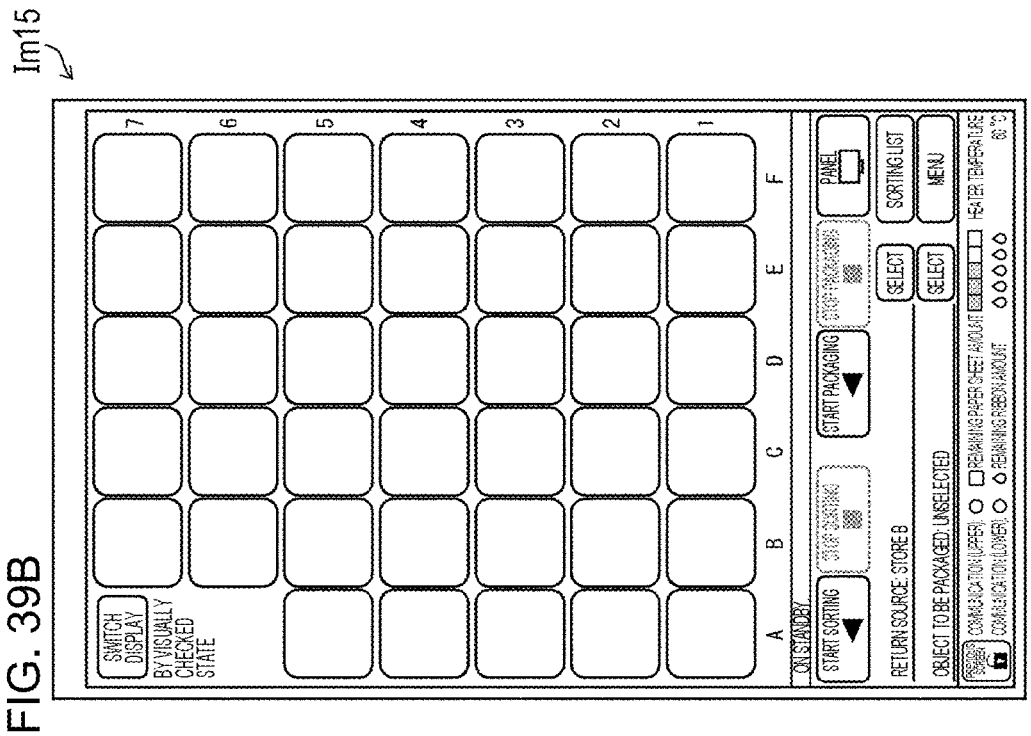
FIG. 39B is a diagram for illustrating an example of the sorting image displayed after the return source selection.
Figure 39A:
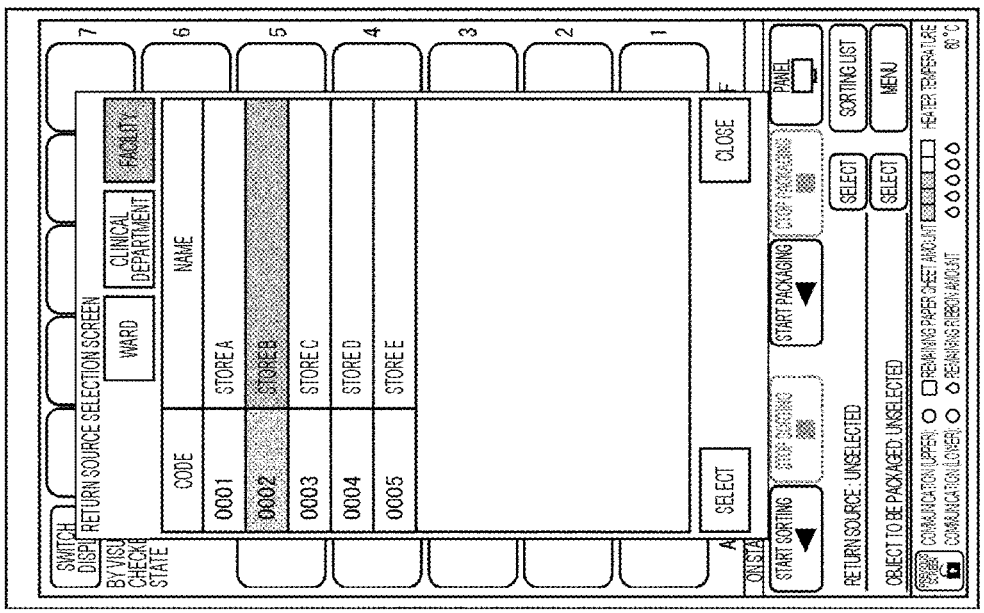
FIG. 39A is a diagram for illustrating an example of a return source selection image.
Figure 40A:
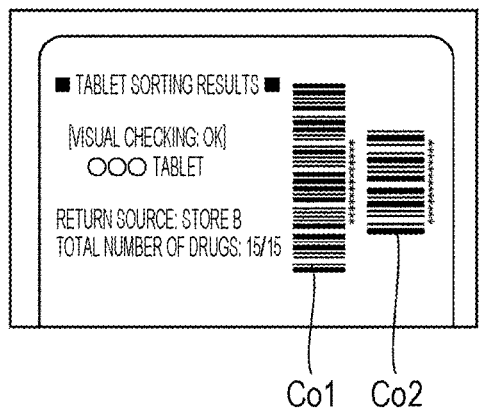
FIG. 40A is a diagram for illustrating an example of printing on a packaging paper sheet.
Figure 40B:
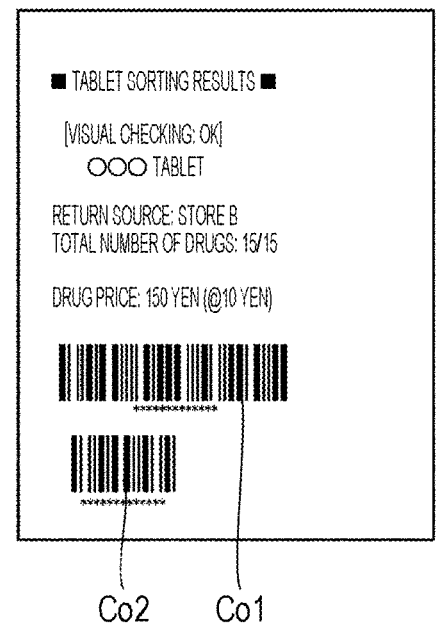
FIG. 40B is a diagram for illustrating an example of printing on a journal.

In this embodiment, the sorting processing performed when a return source is selected is described. FIG. 38A is a diagram for illustrating an example of a sorting image Im15 displayed before the return source is selected, and FIG. 38B is a diagram for illustrating an example of a return source registration image Im16 (facility master edit screen). FIG. 39A is a diagram for illustrating an example of a return source selection image Im17, and FIG. 39B is a diagram for illustrating an example of the sorting image Im15 displayed after the return source selection. FIG. 40A is a diagram for illustrating an example of printing on a packaging paper sheet, and FIG. 40B is a diagram for illustrating an example of printing on a journal.

The "return source" displayed in the sorting image Im15 illustrated in FIG. 38A is a place in which the drug had been stored before having been fed into the drug sorting device 1, for example, a ward, a clinical department, or a facility (for example, medical institution). This embodiment is described by taking an exemplary case in which the return source refers to each store when a dispensing pharmacy is expanding its chain stores.

For example, in the case in which a dispensing pharmacy is expanding its chain stores, when the drug sorting device 1 is introduced into one of the stores and drugs returned to the own store and other stores are collectively sorted and packaged by this drug sorting device 1, it is required to return each of the sorted drugs to its source store. Drugs handled at one store and drugs handled at another store may differ from each other, and hence it is required to return the sorted drugs to the source stores without fail. Hitherto, the sorted drugs have been accommodated into, for example, a basket provided to each store, to thereby prevent the sorted drugs from being accommodated into a basket other than the basket at a target store.

However, due to the manual management, there has been a fear in that the sorted drugs may be inadvertently accommodated into a basket other than the basket at the target store. There has also been no way to mechanically examine when the sorted drugs have been accommodated into a basket other than the basket at the target store.

In view of this, when any one of the stores registered as the return source is selected based on the user input, the drug sorting device 1 according to this embodiment stores information indicating the selected return source.

Specifically, the drug sorting device 1 registers each store by inputting, as the return source, the store name and an ID (facility code) indicating the store name. As illustrated in FIG. 38A, the drug sorting device 1 displays each menu when the user input for a "menu" button Bo3 of the sorting image Im15 is received. When the drug sorting device 1 receives the user input for a "facility master," the drug sorting device 1 displays the return source registration image Im16 illustrated in FIG. 38B. The drug sorting device 1 acquires the store name and the facility code in the return source registration image Im16.

After that, the drug sorting device 1 receives the user input for a "select source selection" button Bo4 of the sorting image Im15 at the start of the drug sorting, to thereby display the return source selection image Im17 illustrated in FIG. 39A. When the store being the return source is selected from among a plurality of stores (registered stores) displayed in the return source selection image Im17, the drug sorting device 1 stores information indicating the selected store, and as indicated in the sorting image Im15 illustrated in FIG. 39B, simultaneously displays the selected store name (Store B in this example). After that, the sorting processing is started based on the user input.

Then, at the time of packaging performed by the packaging mechanism 6, the drug sorting device 1 prints, based on the above-mentioned stored information, the information indicating the store being the return source on the packaging paper sheet or the journal together with the information indicating the packaged drugs. Those pieces of information are printed as, for example, characters and a format readable by an information reader installed in each store (for example, a bar code readable by a bar code reader). In the examples of FIG. 40A and FIG. 40B, a GS1 code Co1 indicating the type of the drugs and a store bar code Co2 indicating the store name are printed.

Thus, at the store being the return source, the filling of drugs can be performed by this store after the visual checking and mechanical checking using the information reader. Therefore, even when the drug sorting device 1 is introduced into one of a plurality of stores and the drugs returned to the own store and the other stores are collectively sorted and packaged by this drug sorting device 1, it is possible to return the drugs to the source stores without fail.

[Example of Implementation by Software]

The control blocks of the drug sorting devices 1 and 1A (in particular, the control units 60a and 60b) may be implemented by a logic circuit (hardware) formed on an integrated circuit (IC chip) or the like, or may be implemented by software.

In the latter case, the drug sorting devices 1 and 1A include a computer configured to execute instructions issued from a program being software for implementing each function. For example, this computer includes one or more processors, and also includes a computer-readable recording medium configured to store the above-mentioned program. On the above-mentioned computer, the above-mentioned processor reads the above-mentioned program from the recording medium and executes the program, to thereby achieve an object of this disclosure. As the above-mentioned processor, for example, a central processing unit (CPU) can be used. As the above-mentioned recording medium, it is possible to use a "non-transitory tangible medium," for example, a tape, a disk, a card, a semiconductor memory, or a programmable logic circuit as well as a read only memory (ROM). In addition, a random access memory (RAM) for loading the above-mentioned program may be further provided. Further, the above-mentioned program may be supplied to the above-mentioned computer via any transmission medium (for example, a communication network or broadcast waves) that is capable of transmitting the program. One aspect of this disclosure may be achieved by the above-mentioned program in the form of a data signal embedded in a carrier wave, which is embodied by electronic transmission.

The same applies to the control blocks of the data management device 500 (in particular, the control unit 502) and the control blocks of the packaging machine 700 (in particular, the control unit 706).

[Supplementary Note]

This disclosure is not limited to each embodiment described above, and various changes may be made thereto within the appended claims. An embodiment obtained by combining as appropriate technical means disclosed in different embodiments is also included in the technical scope of this disclosure.

The invention claimed is:

1. A drug sorting device, comprising:
   a first accommodating portion configured to accommodate a plurality of types of drugs;
   a second accommodating portion configured to accommodate drugs of the plurality of types of drugs in a state of being sorted by type;
   a sensor configured to capture an image of a drug of the plurality of types of drugs conveyed from the first accommodating portion;
   a processor configured to determine whether drug data corresponding to the captured image is present in previously stored drug data relating to each of the plurality of types of drugs; and a sorting unit configured to:
- direct the drug into a first area of the second accommodating portion in response to a determination that the captured image includes drug data present in the previously stored drug data; and
- direct the drug into a second area of the second accommodating portion, different from the first area, in response to a determination that the captured image is free of drug data in the previously stored drug data;

wherein the sorting unit is configured to sort each drug determined to be free of drug data in the previously stored drug data to a corresponding position in the second area based on at least one of a color or a shape of the drug and information attached to the drug in the captured image.

2. The drug sorting device according to claim 1, further comprising a register configured to register, in regard to the drug determined to be free of drug data in the previously stored drug data, drug data on the drug relating to the captured image, based on input from a user, in association with the captured image.

3. The drug sorting device according to claim 2, wherein the processor is further configured to:
- extract at least identification information indicated on the drug included in the captured image, the identification information being usable for identifying the drug; and
- instruct a display to display the captured image and the identification information, wherein the register is configured to register the captured image in response to an orientation of the identification information indicated on the drug included in the captured image matching a predetermined orientation in which the extracted identification information is displayed on the display.

4. The drug sorting device according to claim 3, wherein the processor is configured to instruct the display to display, in response to a determination that the drug is a capsule, a plurality of images captured from a plurality of positions around the capsule.

* * * * *